US010301620B2

(12) United States Patent
Vadolas

(10) Patent No.: US 10,301,620 B2
(45) Date of Patent: May 28, 2019

(54) METHOD OF TREATMENT

(75) Inventor: Jim Vadolas, Carnegie (AU)

(73) Assignee: MURDOCH CHILDRENS RESEARCH INSTITUTE, Parkville (AU)

(*) Notice: Subject to any disclaimer, the term of this patent is extended or adjusted under 35 U.S.C. 154(b) by 0 days.

(21) Appl. No.: 13/996,984

(22) PCT Filed: Dec. 20, 2011

(86) PCT No.: PCT/AU2011/001653
§ 371 (c)(1),
(2), (4) Date: Oct. 7, 2013

(87) PCT Pub. No.: WO2012/083363
PCT Pub. Date: Jun. 28, 2012

(65) Prior Publication Data
US 2014/0031412 A1    Jan. 30, 2014

(30) Foreign Application Priority Data
Dec. 22, 2010 (AU) ............................ 2010905599

(51) Int. Cl.
*C12N 15/11* (2006.01)
*C12N 15/113* (2010.01)
*A61K 48/00* (2006.01)

(52) U.S. Cl.
CPC .......... *C12N 15/113* (2013.01); *A61K 48/005* (2013.01); *C12N 2310/14* (2013.01); *C12N 2310/531* (2013.01); *C12N 2740/16043* (2013.01); *C12N 2830/008* (2013.01); *C12N 2830/46* (2013.01)

(58) Field of Classification Search
CPC ............... C12N 15/86; C12N 2310/14; C12N 2740/16045; A61K 48/00; C07K 14/805; C12P 21/00
See application file for complete search history.

(56) References Cited

U.S. PATENT DOCUMENTS

| | | | |
|---|---|---|---|
| 7,332,310 B2 * | 2/2008 | Nakagawa et al. | 435/115 |
| 7,374,927 B2 * | 5/2008 | Palma | C12Q 1/6883 435/287.2 |
| 2005/0246794 A1 * | 11/2005 | Khvorova | A61K 31/713 800/286 |
| 2007/0039072 A1 * | 2/2007 | Khvorova et al. | 800/286 |
| 2008/0009060 A1 * | 1/2008 | Foulkes | A61K 31/7068 435/375 |
| 2009/0156534 A1 * | 6/2009 | Lisowski et al. | 514/44 |

FOREIGN PATENT DOCUMENTS

| | | | |
|---|---|---|---|
| CN | 1778917 | 5/2006 | |
| CN | 100567490 | 12/2009 | |
| WO | WO 2005054518 A2 * | 6/2005 | C07H 21/04 |
| WO | WO 2012/083363 A1 | 6/2012 | |

OTHER PUBLICATIONS

Myers et al, Fine Structure Genetic Analysis of a beta-globin promoter, 1986, Science, vol. 232, 4750: 613-618.*
Voon et al, siRNA-mediated reduction of alpha-globin results in phenotypic improvements in beta-thalassemic cells, 2008, Haematologica, 93, 8: 1238-1242 and "Design and Methods" attachment, pp. 1-2.*
Zeng et al, CN 1778917, May 2006, machine translation attached, pp. 1-16.*
Advani et al., "Oxidative Red Blood Cell Membrane Injury in the Pathophysiology of Severe Mouse β-Thalassemia," Blood 79:1064-1067 (1992).
Al-Hasani et al., "Complementation of α-thalassaemia in α-globin knockout mice with a 191 kb transgene containing the human α-globin locus," Transgenic Res 13:235-243 (2004).
Amer et al., "Flow cytometric measurement of reactive oxygen species production by normal and thalassaemic red blood cells," Eur J Haematol 70:84-90 (2003).
Andersson et al. "K562—A Human Erythroleukemic Cell Line," Int. J. Cancer 23:143-147 (1979).
Bandyopadhyay and Temin, "Expression of Complete Chicken Thymidine Kinase Gene Inserted in a Retrovirus Vector," Mol Cell Biol 4(4):749-754 (1984).
Beauchemin et al., "Molecular Basis of Cell and Developmental Biology: Differential Regulatory and Compensatory Respnses in Hematopoiesis/Erythropoeisis in αand β-Globin Hemizygous Mice," J. Biol. Chem. 279:19471-19480 (2004).
Berns, K. et al, "A Large-Scale RNAi Screen in Human Cells Identifies New Components of the p53 Pathway", Nature, 2004, vol. 428, No. 6981, pp. 431-437.
Breakefield et al., "Gene Transfer into the Nervous System," Mol. Neurobiol. 1: 339-371 (1987).
Buchschacher and Panganiban, "Human Immunodeficiency Virus Vectors for Inducible Expression of Foreign Genes," J Virol 66(5):2731-2739 (1982).
Cavazzana-Calvo et al., "Transfusion independence and HMGA2 activation after gene therapy of human β-thalassaemia," Nature 457:318-322 (2010).
Fessas, "Inclusions of Hemoglobin in Erythroblasts and Erythrocytes of Thalassemia," Blood 27:21-32 (1963).
Fink et al., "Gene Transfer to Neurons Using Herpes Simples Virus-Based Vectors," Ann Rev Neurosci 19:265-287 (1996).
Fink et al., In Vivo Expression of β-Galactosidase in HippoCampal Neurons by HSV-Mediated Gene Transfer, Hum Gene Ther 3:11-19 (1992).
Freese et al., "Commentary" HSV-1 Vector Mediated Neuronal Gene Delivery, Biochemical Pharmacology 40(10):2189-2199 (1990).
Gorziglia and Kapikian, "Expression of the OSU Rotavirus Outer Capsid Protein VP4 by an Adenovirus Recombinant," J Virol 66(7):4407-4412 (1992).

(Continued)

*Primary Examiner* — Ekaterina Poliakova-Georgantas

(57) ABSTRACT

The present disclosure teaches the treatment of a blood pathology, such as a blood pathology associated with impaired hemoglobin synthesis including the treatment of β-thalassemia or a related hemoglobinopathy. An RNA molecule such as a short interfering RNA or a hairpin RNA which targets an mRNA species encoding α-globin is administered to a subject to reduce the amount of α-globin produced to non-zero levels and ameliorate the effects of an α- and β-globin chain imbalance.

17 Claims, 8 Drawing Sheets

Specification includes a Sequence Listing.

(56) References Cited

OTHER PUBLICATIONS

Hannon, "A conserved biological response to double-stranded RNA, known variously as RNA interference (RNAi) or post-transcriptional gene silencing, mediates resistance to both endogenous parasitic and exogenous pathogenic nucleic acids, and regulates the expression of protein-coding genes. RNAi has been cultivated as a means to manipulate gene expression experimentally and to probe gene function on a whole-genome scale," Nature 418:244-251 (2002).

Helseth et al., "Rapid Complementation Assays Measuring Replicative Potential of Human Immunodeficiency Virus Type 1 Envelope Glycoprotein Mutants," (1990) J Virol 64(5):2416-2420.

International Search Report in corresponding International Application No. PCT/AU2011/001653, dated Mar. 16, 2012.

Johnson et al., "Cytotoxicity of a Replication-Defective Mutant of Herpes Simplex Virus Type 1," J Virol 66(5):2952-2965 (1992).

Kanavakis et al., "A rare example that coinheritance of a severe form of h-thalassemia and a-thalassemia interact in a "synergistic" manner to balance the phenotype of classic thalassemic syndromes," Blood Cells Mol Dis 32:319-324 (2004).

Kong et al., "Loss of α-hemoglobin-stabilizing protein impairs erythropoiesis and exacerbates β-thalassemia," J. Clin. Invest 114:1457-1466 (2004).

Lozzio and Lozzio, "Human Chronic Myelogenous Leukemia Cell-Line with Positive Philadelphia Chromosome," Blood 45:321-334 (1975).

Madzak et al., "Efficient in Vivo Encapsidation of a Shuttle Vector into Pseudo-Simian Virus 40 Virions Using a Shuttle Virus as Helper," J. Gen Virol 73:1533-1536 (1992).

Martin et al., Ein Neuer Zugang Zu 2'-O-Alkylriboneucleosiden und Eigenschaften deren OligonucleotideHelv. Chim. Acta, 78:486-504 (1995) with English Abstract.

Miller et al., "Specific Globin mRNAs in Human Erythroleukemia (K562) Cells," Blood 63: 195-200 (1984).

Miller et al., "Generation of Helper-Free Amphotropic Retroviruses That Transduce a Dominant-Acting, Methotrexate-Resistant Dihydrofolate Reductase Gene,"Mol Cell Biol 5(3):431-437 (1985).

Miller et al., "Design of Retrovirus Vectors for Transfer and Expression of the Human ,βGlobin Gene," J Virol 62(11):4337-4345 (1988).

Moss, "Genetically engineered poxviruses for recombinant gene expression, vaccination, and safety," Proc. Natl. Acad. Sci. USA 93:11341-11348 (1996).

Naldini et al., "In Vivo Gene Delivery and Stable Transduction of Nondividing Cells by a Lentiviral Vector," Science 272:263-267 (1996).

Nielsen et al, "Sequence-Selective Recognition of DNA by Strand Displacement with a Thymine-Substituted Polyamide," Science 254:1497-1500 (1992).

Weir et al., "An Insertion Vector for the Analysis of Gene Expression During Herpes Simplex Virus Infection," Gene 89:271-274 (1990).

Olivieri, "The β-Thalassemias," New Engl J Med 341(2):99-109 (1999).

Paszty et al., "Lethal α-Thalassaemia Created by Gene Trageting in Mice and its Genetic Rescue,"Nature Genetics 11:33-39 (1995).

Patzel, "In Silico Selection of Active siRNA," Drug Discov Today 12(3/4):139-148 (2007).

Petropoulos et al., "Using Avian Retroviral Vectors for Gene Transfer," J Virol 66(6):3391-3397 (1992).

Ponnazhagan et al., "Suppression of Human α-Globin Gene Expression Mediated by the Recombinant Adeno-Associated Virus 2-based Antisense Vectors," J Exp Med 179:733-738 (1994).

Quantin et al., "Adenovirus as an Expression Vector in Muscle Cells in Vivo," Proc Natl Acad Sci USA 89:2581-2584 (1992).

Rosenfeld et al., "In Vivo Transfer of the Human Cystic Fibrosis Transmembrane Conductance Regulator Gene to the Airway Epithelium," Cell 68: 143-155 (1992).

Rubinson et al., "A Lentivirus-Based System to Functionally Silence Genes in Primary Mammalian Cells, Stem Cells and Transgenic Mice by RNA Interference," Nat. Gene 33:401-406 (2003).

Russell and Hirata, "Human Gene Targeting by Viral Vectors," Nat Genetics 18:325-330 (1998).

Rutherford et al., "Embryonic Erythroid Differentiation in the Human Leukemic Cell Line K562," Proc Natl Acad Sci USA 78(1):348-352 (1981).

Samakoglu, S. et al, "A Genetic Strategy to Treat Sickle Cell Anemia by Coregulating Globin Transgene Expression and RNA Interference," Nature Biotechnology, 2006, vol. 24, No. 1, pp. 89-94.

Sarakul, O. et al., "Inhibition of α-globin expression by RNAi", Biochemical and Biophysical Research Communications, 369:935-938 (2008).

Scher et al., "DNA Ligase and Dnase Activities in Mouse Erythroleukemia Cells during Dimethyl Sulfoxide-induced Differentiation," Cancer Res 42:1300-1306 (1982).

Schiedner et al., "Genomic DNA Ttransfer with a High-Capacity Adnovirus Vector in Improved in Vivo Gene Expression and Decreased Toxicity," Nature 18: 180-183 (1998).

Schrier and Mohandas, "Globin-chain Specificity of Oxidation-induced Changes in Red Blood Cell Membrane Properties," Blood 79:1586-1592 (1992).

Schrier, "Pathophysiology of Thalassemia," Hematol 123-126 (2002).

Schrier et al., "Cellular and Membrane Properties of Alpha and Beta Thalassemic Erythrocytes are Different: Implication for Differences in Clinical Manifestations," Blood 74:2194-2202 (1989).

Schrier, "Thalassemia: Pathophysiology of Red Cell Changes," Annu Rev. Med. 45:211-18 (1994).

Schrier et al., "The Role of Oxidant Injury in the Pathophysiology of Human Thalassemias," Redox Rep 8(5): 241-245 (2003).

Scott et al., "Effect of Excess α-Hemoglobin Chains on Cellular and Membrane Oxidation in Model β-Thalassemic Erythrocytes," J. Clin. Invest. 91:1706-1712 (1993).

Shen et al., Multi-ribozyme Targeting of Human α-Globin Gene Expression, Blood Cells, Mol. Dis. 25(24) Dec. 31:361-373 (1999).

Shimada et al., "Targeted and Highly Efficient Gene Transfer into CD4+ Cells by a Recombinant Human Immunodeficiency Virus Retroviral Vector," J. Clin Invest 88:1043-1047 (1991).

Sorge et al., "Amphotropic Retrovirus Vector System for Human Cell Gene Transfer," Mol. Cell. Biol. 4(9):1730-1737 (1984).

Stratford-Perricaudet et al., "Evaluation of the Transfer and Expression in Mice of an Enzyme-Encoding Gene Using a Human Adenovirus Vector," Human Gene Therapy 1:241-256 (1990).

Thein et al., "Thalassaemia Intermedia: A new Molecular Basis," Br J. Haematol 56:33-337 (1984).

Thein, "Genetic Modifiers of β-Thalassemia," The Hematology Journal 90(5):649-660 (2005).

Thein, "Pathophysiology of β Thalassemia—A Guide to Molecular Therapies," Hematology, pp. 31-37 (2005).

Vadolas et al., "Transgene copy number-dependent rescue of murine h-globin knockout mice carrying a 183 kb human h-globin BAC genomic fragment," Biochimica et Biophysica Acta 1728:150-162 (2005).

Voon et al., "siRNA-Mediated Reduction of α-globin results in Phenotypic Improvements in β-Thalassemic Cells," Haematologica 93(8):1238-1242 (2008).

Wannasuphaphol et al., "Rescued Mice with Hb E Transgene—Developed Red Cell Changes Similar to Human β-Thalassemia/HbE Disease," Ann. N.Y. Acad. Sci. 1054:407-416 (2005).

Wilkinson et al., "Constitutive and enhanced expression from the CMV major IE promoter in a defective adenovirus vector," Nucleic Acids Res 20(9):2233-2239.

Xie, S-Y, et al., "Restoration of the balanced α/β-globin gene expression in β654 thalassemia mice using combined RNAi and antisense RNA approach", Human Molecular Genetics. 16(21): 2616-2625.

Yang et al., "A Mouse Model for $\beta^0$-Thalassemia," Proc. Natl. Acad. Sci. 92:11608-11612 (1995).

* cited by examiner

Figure 2B

```
A   H   K       L   R   V   D   P   V   N       F   K   L   L       S   H   C   L   L   V   T   L   A       A   H   L   P       A   E   F   T   P   A
```
Exon 2                                                                                                                                              Exon 3 cgcgcacaag cuucggguqg acccggucaa cuucaagcuc cuaagccacu gccugcuggu gcccuggcc gaccougqcc gccaccucc ccgccgaguu cacccougcg
gccguguuc gaagcccacc ugggccaguu gaauucgag gauucgguga cggacgacca cugggaccgg cggugggagg ggcggcucaa gugggacgc

```
V   H   A   S   L   D   K       F   L   A       S   V   S   T   V   L   T       S   K   Y       R
```
                                        Patent α2                                       Patent α3
                                                        Hs siα3      exact
                                                            Mm_siα3
Exon 3 gugcacgccu cccuggacaa guuccuggcu ucugugagca ccgugcugac cuccaaauac cguuaagcug gagccucggu agccguuccu ccugccgcu
cacgugccgga gggaccuguu caaggaccga agacacucgu ggcacgacug gaguuuaug gcaauucgac cucgagcca ucggcaagga ggacggcga
                                                                                                Poly A signalPoly   A      site gggccuccca acgggcccuc cuccccuccu ugcaccggcc cuuccugguc uuugaauaaa gucugagugg gcggc
cccggagggu ugcccgggag gaggggagga acgugggccgg gaaccaccag aaacuuauuu cagacucacc cgccg

Figure 2C

METHOD OF TREATMENT

FILING DATA

This application is a U.S. national phase application of International PCT patent application No. PCT/AU2011/001653, filed on Dec. 20, 2011, which is associated with and claims priority from Australian Provisional Patent Application No. 2010905599, filed on 22 Dec. 2010, entitled "A method of treatment", the entire contents of which, are incorporated herein by reference.

STATEMENT REGARDING SEQUENCE LISTING

The Sequence Listing associated with this application is provided in text format in lieu of a paper copy, and is hereby incorporated by reference into the specification. The name of the text file containing the Sequence Listing is DAVI_022_00US_ST25.txt. The text file is about 279 KB, was created on Sep. 9, 2013, and is being submitted electronically via EFS-Web.

FIELD

The present disclosure teaches the treatment of a blood pathology, such as a blood pathology associated with impaired hemoglobin synthesis including the treatment of β-thalassemia or a related hemoglobinopathy.

BACKGROUND

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

Thalassemia is an inherited autosomal recessive blood disorder caused by the faulty synthesis of hemoglobin. This arises by one or more genetic defects affecting synthesis of the α- or β-globin chains which make up hemoglobin.

The World Health Organization (WHO) has conservatively estimated that approximately 7 percent of the world's population are carriers of various types of hemoglobinopathies, with an estimated 300,000 severely affected patients born worldwide each year. Although thalassemia is most common in Mediterranean, Middle Eastern, African and Asian populations (Olivieri (1999) *N Engl J Med* 341:99-109; Thein (2005) *Hematology:* 31-37), the ever rising rates of population migration mean this condition is encountered with increasing frequency in many parts of the world, including Northern Europe, North America and Australia. Thalassemia is fatal if left untreated and patients are dependent on a regular blood transfusion every 3-4 weeks for the rest of their lives.

There are over 200 β-globin gene mutations (Olivieri (1999) supra) which impair β-globin synthesis, resulting in imbalanced globin chain synthesis and β-thalassemia. In these situations, the excess, unbound α-globin chains precipitate in erythroid progenitor cells resulting in premature cell death, ineffective erythropoiesis and severe anemia. The key role of globin imbalance in contributing to thalassemia severity is most clearly illustrated in individuals who inherit an abnormal number of functional α-globin genes along with β-globin mutations. Individuals who co-inherit α-thalassemia with homozygous β-thalassemia have an improved phenotype and suffer less severe anemia than if either set of mutations was inherited alone (Camaschella et al. (1995) *Am J Hematol* 48:82-87; Cao et al (1991) *Am J Pediatr Hematol Oncol.* 13:179-188; Kanavakis et al. (2004) *Blood Cells Mol Dis* 32:319-324; Schrier (2002) *Curr Opin Hematol* 9:123-126; Thein (2005) *Haematologica* 90:649-660). The degree of correction is closely related to the degree to which globin chain balance has been restored (Thein et al (1984) *Br J Haematol.* 56:333-337). One mutated copy of α-globin generally has minimal impact but two or three mutated α-globin genes can improve β-thalassemic phenotypes significantly (Camaschella et al. (1995) supra; Cao et al. (1991) supra; Kanavakis et al. (2004) supra; Schrier (2002) supra; Thein (2005) supra). Therefore, alterations in α-globin chain synthesis can have considerable effects on β-thalassemic phenotypes and can even confer transfusion independence. Given that excess production of α-globin leads to widespread detrimental effects in β-thalassemia, reduction of α-globin synthesis would likely improve the β-thalassemic phenotype, raising the possibility of reducing α-globin expression as a therapy for β-thalassemia. The difficulty, however, is to specifically target α-globin gene expression.

Expression and synthesis of the α-globin and β-globin chains of hemoglobin is balanced during normal erythropoiesis and any disruptions in the α:β-globin synthesis ratios results in thalassemia (Olivieri (1999) supra; Thein (2005) supra). β-Thalassemia arises when α-globin is synthesized at levels exceeding the binding capacity of available β-globin chains, usually due to mutations affecting the β-globin locus which reduce β-globin expression (Schrier (1994) *Annu Rev Med* 45:211-218). Conversely, α-thalassemia occurs due to mutations which result in decreased α-globin expression, leading to an excess of β-globin chains (Schrier (1994) supra). Reduced expression of either of the globin chains leads to decreased formation of functional hemoglobin tetramers, yet this plays a relatively minor role in contributing to the severely anemic phenotype characteristic of the thalassemias. Instead, it is the damage caused at the cellular level by excess, improperly paired globin chains, which leads to premature cell death and accounts for the majority of the pathology (Schrier (1994) supra). Excess α-globin results in the formulation of large, insoluble aggregates which can be visualized by light microscopy in an estimated one third of β-thalassemic red blood cells (RBCs) [Fessas (1963) *Blood* 21:21-32], and occurs even in the earliest erythroid precursor cells (Schrier (1994) supra). These α-globin aggregates cause mechanical damage to membrane structures and trigger premature apoptosis in erythroid progenitor cells, leading to ineffective erythropoiesis (Thein (2005) supra; Kanavakis et al. (2004) supra). Furthermore, the excess α-globin is heavily oxidized (Advani et al. (1992) *Blood* 79:1064-1067) and each globin chain also carries a heme bound iron which can induce generation of reactive oxygen species (ROS) [Schrier et al. (2003) *Redox Rep.* 8:241-245]. It is believed that the increased ROS oxidizes adjacent membrane proteins, leading to severe membrane abnormalities and unstable cell membranes and this results ultimately in hemolysis and ungreatly exacerbating the anemic phenotype in β-thalassemia (Advani et al. (1992) supra).

RNAi is a highly conserved, naturally occurring mechanism of gene suppression found in plant, yeast and mammalian cells, which can be mediated by naturally occurring or synthetic short interfering RNAs (siRNA) [Hannon (2002) *Nature* 418:244-251]. In mammalian cells, RNAi can be induced using dsRNA of 19-21 bp with characteristic two nucleotide 3' overhangs and 5' phosphate groups. These are incorporated into an RNA induced silencing complex (RISC) and used as a template for cleavage of endogenous mRNA. Since targeting is dependent mainly on Watson-Crick base-pairing, it is theoretically possible to utilize this pathway to reduce expression of any gene in a sequence-specific manner.

Sarakul et al. (2008) *Biochemical and Biophysical Research Communication* 369:935-938 disclosed the use of siRNA at a specific region of Exon2 of the α-globin gene locus. However, other target sites within the gene were ineffective in reducing expression. Chinese Patent Application No. 100567490 (CN 100567490) also used siRNA to target specific sites with variable effectiveness. These sites were defined as α2 and α3 (referred to herein as "CNα2" and "CNα3", respectively). CNα3 targets codons 127 to 133 which is SEQ ID NO:3 in Sarakul et al. (2008) supra. The latter authors stated that only one sequence (SEQ ID NO:1, targeting codons 41 to 47 in Exon2) had any effect. Hence, there is clearly inconsistency between the data by Sarakul et al. (2008) supra and CN100567490. This highlights the difficulty in designing effective siRNA molecules. The present disclosure included siRNA encoding SEQ ID NO:1, (targeting codons 41 to 47 in Exon2) as a control (referred to as Hs-siα5) and found that this siRNA was the least effective in reducing alpha-globin expression compared to all other siRNA tested. Also demonstrating that siRNA targeting other regions not anticipated by Sarakul et al. (2008) supra and CN100567490 are potentially more effective in reducing α-globin.

In order to assess the feasibility of RNAi-mediated therapy, a mouse model has been developed. The most well characterized is the heterozygous β-globin knockout (β-KO) model (Yang et al. (1995) *Proc Natl Acad Sci USA* 92:11608-11612), which displays distinct hematological abnormalities consistent with β-thalassemia (wide variations of red cell distribution width (RDWs), significant reductions in hemoglobin (Hb) and hematocrit (HCT) levels) [Yang et al. (1995) supra; Beauchemin et al. (2004) *J Biol chem.* 279:19471-19480; Vadolas et al. (2005) *Biochim Biophys Acta* 1728:150-162). In order to assess the effects of reduced α-globin expression in β-thalassemic mice, heterozygous α-globin knockout mice (α-KO) were crossed with thalassemic β-KO mice (Beauchemin et al. (2004) supra; Al-Hasani et al. (2004) *Transgenic Res* 13:235-243; Paszty et al. (1995) *Nat Genet* 11:33-39). The resultant double heterozygous (DH) α-KO/β-KO progeny expressed reduced, but balanced, levels of both α-globin and β-globin and displayed a normal range of RDWs with Hb and HCT almost completely restored to wild type (WT) levels. Furthermore, the reduced drive for extramedullary erythropoiesis combined with reduced clearance of damaged RBC, resulted in a marked reduction in spleen size indistinguishable from those found in WT mice.

Whilst intuitively there are benefits of reducing α-globin expression in the context of β-thalassemia, there have been no reported substantial reductions of α-globin using methods which are conducive to therapy in humans. An siRNA approach was investigated to mediate reductions in α-globin expression in mice. One highly effective siRNA sequence (siα4), located in the 3' untranslated region, was demonstrated to reduce α-globin expression in hemoglobinized murine erythroleukemic (MEL) cells by approximately 65% at both the RNA and the protein levels (Voon et al. (2008) *Haematologica* 93:1238-1242). The efficacy of siα4 was further confirmed by testing this sequence in primary cultures of erythropoietic progenitor cells There is a need to use gene silencing technology to greater effect to treat β-thalassemia and related conditions arising from an excess amount of α-globin in humans.

SUMMARY

The present disclosure teaches a method for treating β-thalassemia or a related hemoglobinopathy associated with an excess of α-globin in humans. Related conditions include HbE disease and sickle cell disease (SCD). The method enabled herein targets the α-globin genetic locus to reduce its expression thereby reducing levels of the α-globin chain. Reference to the human α-globin genetic locus includes HBA1 (SEQ ID NO:41) and HBA2 (SEQ ID NO:573). This in turn corrects or at least improves or reduces the α:β-globin ratio imbalance which leads to an amelioration of the symptoms or underlying cause of β-thalassemia. In an embodiment, the agent is an RNA such as a single or double (duplex) short, interfering RNA (siRNA) oligonucleotide or a hairpin form thereof or a chemically modified or synthetic or mimetic form thereof which targets a mRNA species transcribed from the α-globin genetic locus at a site selected from the 5' untranslated region (5'-UTR), Exon1, Exon3 and the 3'-UTR or a boundary region between. The oligonucleotide may be synthetically derived or produced by expression of a DNA sequence in an expression vector such as a Lentiviral vector. Generally, down-regulation of the α-globin genetic locus is mediated via RNAi. In an embodiment, the ratios of α-globin and β-globin are improved to near normal levels. In an embodiment, the RNAi approach is used in conjunction with gene therapy to restore normal or near normal β-globin levels.

The present specification is instructional on a gene silencing approach to reduce expression of the α-globin genetic locus to non-zero expression levels which means expression of the α-globin genetic locus or levels of α-globin protein is from about 30% to 95% of the levels in a cell from a non-β-thalassemic subject ("normal control"). Examples of RNA molecules are those which target or comprise a nucleotide sequence of α-globin mRNA selected from SEQ ID NOs:25 and 26 (sense and anti-sense Hs-siα1), 27 and 28 (sense and antisense Hs-siα2), 29 and 30 (sense and antisense Hs-siα3), 31 and 32 (sense and antisense Hs-siα4). However, any site within the 5'-UTR, Exon1, Exon3 or the 3'-UTR or boundary regions inbetween and which results in a reduction in α-globin levels may be targeted.

Examples of mimetics include peptide-oligonucleotide chimeras referred to as a peptide oligonucleotide. Examples of other modified forms include branched oligonucleotides, hairpin oligonucleotides and synthetic oligonucleotide comprising chemically modified bases or bonds between bases. Hairpin RNA species are particularly useful in the practice of the present method.

In an embodiment, the agent is an siRNA oligonucleotide comprising a molecule of from about 15 to about 50 bp in length of HBA1 and/or HBA2 mRNA. Exemplary oligonucleotides target a region on α-globin mRNA selected from SEQ ID NO:42 to SEQ ID NO:572 and SEQ ID NO:574 to SEQ ID NO:1179. Whilst the 15mer oligonucleotides are exemplary target sequences, the present disclosure teaches oligonucleotides from 15 to 50 nucleotides in length which target or comprise a sequence comprising a sequence set forth in one of the 15mers. Particular examples of targets include SEQ ID NO:25, 26, 27, 28, 29, 30, 31 and 32. The RNAi-mediated silencing may also employ RNA species comprising a nucleotide sequence selected from SEQ ID NO:25, 26, 27, 27, 28, 29, 30, 31 and 32.

The method contemplated herein does not extend to the specific target site Hs-siα5 disclosed by Sarakul et al (2008) supra and CN 100567490 and sites α2 and α3 also disclosed by the Chinese patent application. The Hs-siα5 is used herein as a control.

Enabled herein is a method for treating a human subject with β-thalassemia or a related hemoglobinopathy, the method comprising administering to the subject an amount of an agent effective to reduce expression of the α-globin genetic locus thereby reducing levels of α-globin and ameliorating the effects of an α- and β-globin chain imbalance. Reducing expression of the α-globin genetic sequence includes targeting α-globin mRNA. The method may be practices alone or in combination within gene therapy to introduce a functional β-globin-encoding nucleic acid molecule.

Further taught herein is the use of an agent which reduces expression of the α-globin genetic locus in the manufacture of a medicament in the treatment of β-thalassemia or a related hemoglobinopathy in a subject.

The present disclosure provides a method for treating a human subject with β-thalassemia or a related hemoglobinopathy, the method comprising administering to the subject an effective amount of a RNA which targets an mRNA species encoding α-globin at a site selected from the 5'-UTR, Exon1, Exon3 and 3'-UTR or a boundary region inbetween to thereby reduce the amount of α-globin produced to non-zero levels and ameliorate the effects of an α- and β-globin chain imbalance.

The agents may be oligonucleotides such as an RNA species or may be a cellular or viral vector capable of producing a DNA-derived or RNA-derived RNA species.

In an embodiment, an agent is provided comprising a RNA which targets an mRNA species encoding α-globin at a site selected from the 5'-UTR, Exon1, Exon3 and the 3'-UTR and a boundary region inbetween to reduce the amount of α-globin produced for use in ameliorating the symptoms of β-thalassemia or a related hemoglobinopathy in a subject.

In an embodiment, the RNA is an siRNA or a chemically modified or mimetic thereof. This includes a hairpin RNA species. Examples of RNA molecules comprise or target a sequence selected from SEQ ID NO:25, 26, 27, 28, 29, 30, 31 and 32. Other examples, are agents which target SEQ ID NO:42 to 572 or SEQ ID NO:574 to 1179 with the exception of CNα2, CNα3 and Hs-siα5.

Systems for the treatment of β-thalassemia or a related hemoglobinopathy arising from an imbalance of α-globin and β-globin chains are also contemplated herein. One such system taught herein the use of a combination of β-globin gene therapy and RNAi-mediated reduction in α-globin. In an example of this system, a Lentiviral (LV) vector is used to deliver a β-globin-encoding nucleic acid molecule and RNAi sequences to specifically target α-globin mRNA at a site selected from its 5'-UTR, Exon1, Exon3 and 3'-UTR or a boundary region inbetween. The system aims to normalize α:β-globin ratios. Conveniently, the RNAi-encoding sequences are inserted in a 5'-UTR or 3'-UTR or intron in the β-globin-encoding sequence.

In an embodiment, the instant disclosure teaches a RNA which targets a mRNA species encoding α-globin at a site selected from the 5'-UTR, Exon1, Exon3 and the 3'-UTR and a boundary inbetween to reduce the amount of α-globin produced in the manufacture of a medicament in the treatment of β-thalassemia or a related hemoglobinopathy in a subject.

Another aspect enabled herein is directed to a vector comprising a nucleic acid molecule encoding human β-globin operably linked to a promoter and one or more second nucleic acid molecules inserted in the 5'-UTR and/or 3'-UTR region and/or an intron of the β-globin-encoding nucleic acid molecule which second nucleic acid molecule encodes an RNA which targets an mRNA species encoding α-globin at a site selected from the 5' untranslated region (5'-UTR), Exon1, Exon3 and the 3'-UTR or a boundary region inbetween. In an embodiment, the vector provides therapeutic levels of β-globin while reducing α-globin levels.

A summary of sequence identifiers used throughout the subject specification is provided in Table 1. Abbreviations referred to herein are defined in Table 2.

TABLE 1

Summary of sequence identifiers

| SEQUENCE ID NO: | DESCRIPTION |
| --- | --- |
| 1 | si-α1 sense |
| 2 | si-α1 antisense |
| 3 | si-α2 sense |
| 4 | si-α2 antisense |
| 5 | si-α3 sense |
| 6 | si-α3 antisense |
| 7 | si-α4 sense |
| 8 | si-α4 antisense |
| 9 | pshα1 oligo |
| 10 | pshα1 oligo FWD |
| 11 | pshα1 oligo |
| 12 | pshα1 oligo REV |
| 13 | pshα2 oligo |
| 14 | pshα2 oligo FWD |
| 15 | pshα2 oligo |
| 16 | pshα2 oligo REV |
| 17 | pshα3 oligo |
| 18 | pshα3 oligo FWD |
| 19 | pshα3 oligo |
| 20 | pshα3 oligo REV |
| 21 | pshα4 oligo |
| 22 | pshα4 oligo FWD |
| 23 | pshα4 oligo |
| 24 | pshα4 oligo REV |
| 25 | Hs_si-α1 sense |
| 26 | Hs_si-α1 antisense |
| 27 | Hs_si-α2 sense |
| 28 | Hs_siα2 antisense |
| 29 | Hs_si-α3 sense |
| 30 | Hs_si-α3 antisense |
| 31 | Hs_si-α4 sense |
| 32 | Hs_si-α4-antisense |
| 33 | Hs_si-α5 sense |
| 34 | Hs_si-α5 antisense |
| 35 | Stealth si-α1 sense |
| 36 | Stealth si-α1 antisense |
| 37 | Stealth si-α2 sense |
| 38 | Stealth si-α2 antisense |
| 39 | Stealth si-α3 sense |
| 40 | Stealth si-α3 antisense |
| 41 | Nucleotide sequence of hemoglobin α1 (HBA1) mRNA after U to T conversion |
| 42 to 572 | 15mer sense oligonucleotides which represent targets on HBA1 mRNA[1] |
| 573 | Nucleotide sequence of hemoglobin α1 (HBA2) mRNA |
| 574-1179 | 15mer sense oligonucleotides which represent targets on HBA2 mRNA[2] |
| 1180 | Complement of SEQ ID NO: 41 in same direction after T to U conversion - HBA1 |

[1]Target sequences based on HBA1 (NM_000558.3).
[2]Target sequences based on HBA2 (NM_000517.4).

Insofar as the target is mRNA, T nucleotides are U nucleotides. Both RNA and DNA sequences are encompassed herein.

TABLE 2

Abbreviations

| Abbreviation | Definition |
|---|---|
| α-KO | α-Globin knock-out genotype |
| β-KO | β-globin knock-out genotype |
| CNα2 | Target site disclosed in Chinese Patent Application No. 100567490 |
| CNα3 | Target site disclosed in Chinese Patent Application No. 100567490 |
| DCFH | 2,7-Dichlorfluorescein |
| DH | Double heterozygous |
| FBE | Full blood examination |
| FCS | Fetal calf serum |
| Hb | Hemoglobin |
| HBA | Hemoglobin α-globin. Includes HBA1 and HBA2. |
| HCT | Hematocrit |
| LTR | Long term repeat |
| LV | Lentiviral vector |
| LVβ | Leniviral vector comprising nucleic acid encoding β-globin |
| MEL cells | Murine erythroleukemic cells |
| Retic | Reticulocyte |
| RBC | Red blood cell |
| RDW | Red cell distribution width |
| RISC | RNA induced silencing complex |
| ROS | Reactive oxygen species |
| RRE | Rev-responsive element |
| SA | Splicing acceptor |
| SD | Splicing donor |
| SIN | Self inactivating |
| shRNA | Short hairpin RNA |
| siRNA | Short, interfering RNA |
| siα1, siα2 | siRNA's targeting the 5' end region of the human α-globin gene |
| siα3, siα4 | siRNA's targeting the 3' end region of the human α-globin gene |
| siα5 | siRNA targeting Exon2 of the human α-globin gene |
| WT | Wild-type |

BRIEF DESCRIPTION OF THE FIGURES

FIGS. 2B/C provides a schematic representation of the nucleotide sequence of mRNA (coding and non-coding) of HBA1 (SEQ ID NO: 41) showing location of various human and murine target siRNAs. Patentα2 and Patentα3 refer to the sequences disclosed in CN 100567490.

DETAILED DESCRIPTION

Figure 1:
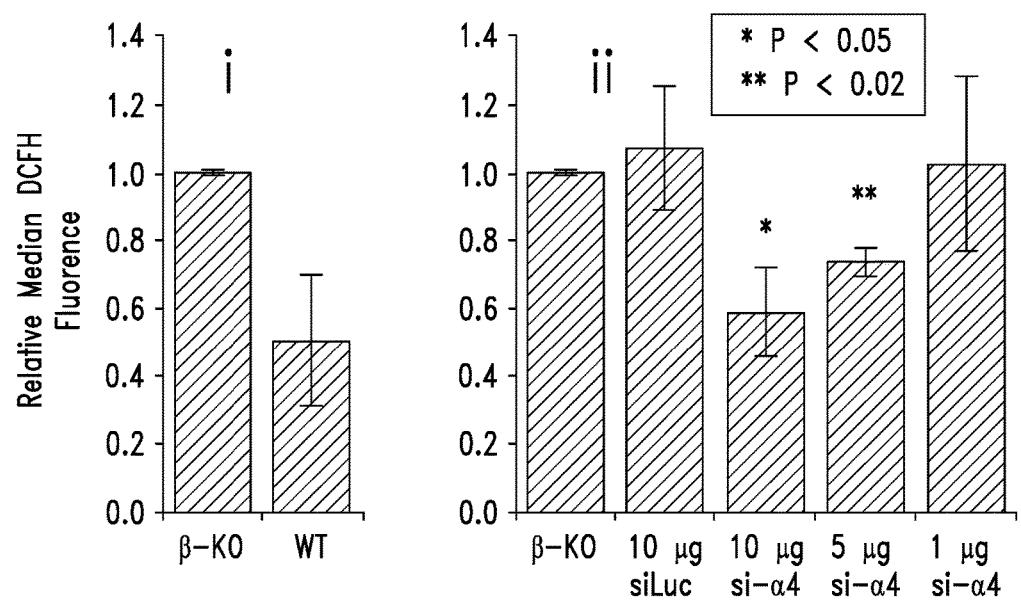
FIG. 1 is a graphical representations showing the restoration of globin balance in primary erythropoietic cells from heterozygous β-KO mice. (A) Relative α:β-globin RNA ratios in cultured primary erythroid progenitor cells from (i) WT (wild type) and heterozygous β-KO (knock out) and (ii) heterozygous β-KO cells treated with 10 μg, 5 μg or 1 μg of siα4 or an siLuc (luciferase) irrelevant control. (B) Relative levels of ROS (reactive oxygen species) in cultured primary erythroid progenitor cells from (i) WT and heterozygous β-KO and (ii) heterozygous β-KO cells treated with 10 μg, 5 μg or 1 μg of siα4 or an siLuc irrelevant control. All values shown represent the mean average of at least three independent experiments ±standard deviation.

Throughout this specification, unless the context requires otherwise, the word "comprise", or variations such as "comprises" or "comprising", will be understood to imply the inclusion of a stated element or integer or method step or group of elements or integers or method steps but not the exclusion of any other element or integer or group of elements or integers or method steps.

As used in the subject specification, the singular forms "a", "an" and "the" include plural aspects unless the context clearly dictates otherwise. Thus, for example, reference to "medicament" includes a single medicament, as well as two or more medicaments; reference to "an agent" includes a single agent, as well as two or more agents; reference to "the disclosure" includes a single or multiple aspects taught herein. Aspects taught and enabled herein in the context of the treatment of a blood pathology such as β-thalassemia are encompassed by the term "invention". All such aspects are enabled within the width of the present invention.

β-Thalassemia is an inherited hemoglobinopathy caused by defective synthesis of the β-globin chain of hemoglobin. This leads to an imbalance of α- and β-globin chains. Excess α-globin precipitates in erythroid progenitor cells resulting in cell death, ineffective erythropoiesis and severe anemia. In accordance with the teachings of the present disclosure, a system is developed to specifically target expression of the α-globin genetic locus to reduce levels of α-globin. A reduction in the levels of α-globin in β-thalassemia patients helps reduce the imbalance of α- and β-globin chains thereby ameliorating the symptoms of β-thalassemia in subjects. By targeting expression of the α-globin genetic locus includes specifically targeting mRNA species encoding α-globin. Generally, the α-globin mRNA is targeted at a site selected from the 5'-UTR, Exon1, Exon3, the 3'-UTR and a boundary region inbetween. The α-globin expression may be targeted alone or in combination with gene therapy to elevate β-globin levels. Reference to α-globin includes hemoglobin α-globin 1 (HBA1; SEQ ID NO:41) and hemoglobin α-globin 2 (HBA2; SEQ ID NO:573).

Accordingly, an aspect enabled herein is a method comprising the step of administering an agent to a human subject having or suspected of having β-thalassemia or a related hemoglobinopathy wherein the agent is provided in an amount which reduces to non-zero levels the expression of the α-globin genetic locus thereby reducing levels of α-globin and ameliorating the effects of an α- and β-globin chain imbalance.

Taught herein is a method for treating a human subject with β-thalassemia or a related hemoglobinopathy, the method comprising administering to the subject an amount of an agent effective to reduce expression of the α-globin genetic locus thereby reducing levels of α-globin and ameliorating the effects of an α- and β-globin chain imbalance.

The present disclosure is instructional on a therapeutic system for treating β-thalassemia or a related hemoglobinopathy in a human subject, the system comprising reducing expression of genetic material encoding the α-globin chain of hemoglobin to thereby reduce levels of α-globin. Such a system facilitates correction, improvement or reduction in the ratio of α- and β-globin chains. Reduced levels of free α-globin chains leads to a reduction in its precipitation in erythroid progenitor cells. Reference to "β-thalassemia" includes blood pathology conditions such as a blood pathology associated with impaired haemoglobin synthesis. Such conditions include those resulting in an α:β-globin imbalance, and which result in an excess of α-globin. Related hemoglobinopathies include HbE and sickle cell disease.

Further taught herein is a method of treating a blood pathology associated with an excess of α-globin in a subject, the method comprising administering to the subject an effective amount of an agent which reduces the level of expression of the α-globin genetic locus, the level being from between less than the level of expression determined prior to intervention to a level above zero, thereby reducing α-globin production and normalizing α- and β-globin levels.

Taught herein is a method for treating a human subject with β-thalassemia or a related hemoglobinopathy, the method comprising administering to the subject an effective amount of a RNA which targets an mRNA species encoding α-globin at a site selected from the 5'-UTR, Exon1, Exon3, the 3'-UTR and a boundary region inbetween to thereby reduce the amount of α-globin produced to non-zero levels and ameliorate the effects of an α- and β-globin chain imbalance.

The agent may target any part of the α-globin genetic locus, including exons, introns, 5'-UTR, 3'-UTR and boundary regions of mRNA transcribed from the locus. In an embodiment, the agent targets a region selected from the 5'-UTR, Exon1, Exon3, 3'-UTR and any intronic region on an mRNA species encoding α-globin. The agent does not target the exact Hs-siα5 site as disclosed by Sarakul et al, (2008) supra and in CN 100567490 or the sites referred to in CN 100567490 as α2 and α3 (CNα2 and CNα3, respectively). The agent may target any site either side of Hs-siα5, CNα2 and CNα3 which results in reduced expression of the α-globin locus. This extends to from one nucleotide to up to 50 nucleotides 5' or 3' of Hs-siα5, CNα2 and/or CNα3. Hence, Exon2 of the α-globin mRNA may also be targeted but not at Hs-siα5.

The agent taught herein induces a level of gene silencing of the α-globin genetic locus. An example of such a type of agent is an agent which induces RNAi-mediated gene silencing. The agent may, for example, be a nucleic acid molecule or a component of RNA induced silencing complex (RISC). In an embodiment, the agent is an oligonucleotide in single or double stranded form such as a single or double stranded (duplex) short, interfering RNA (siRNA) molecule or hairpin RNA which comprises a strand having some nucleotide identity to a nucleotide sequence within an mRNA encoded by the α-globin genetic locus such as SEQ ID NO:25, 26, 27, 28, 29, 30, 31 or 32.

In an embodiment, the agent is an siRNA of from about 15 to 50 bp in length such as 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 bp in length or a hairpin form thereof. The agent may extend to larger or smaller nucleic acid molecules.

The RNA may correspond to any region within the α-globin genetic locus or mRNA encoded thereby such as the 5'-UTR portion and exon therein and/or the 3'-UTR portion. Furthermore, the siRNA may correspond to any region within the α-globin genetic locus or more particularly mRNA encoded thereby such as the 5'-UTR portion and/or the 3'-UTR portion. Generally, the RNA targets or comprises a nucleotide sequence selected from the 5'-UTR, Exon1, Exon3, 3'-UTR or a boundary region inbetween such as SEQ ID NO:25 through 32.

In an embodiment, the agent is an siRNA comprising at least 15 bp which targets or comprises a sequence on the α-globin mRNA nucleotide sequence selected from the list consisting of SEQ ID NO:42 to SEQ ID NO:572 and SEQ ID NO:574 to SEQ ID NO:1179, inclusive. It is a proviso herein that the agent does not target the exact sequence corresponding to Hs-siα5 (Sarakul et al. (2008) supra; CN 100567490) (for the α2 and α3 sequences of CN 100567490 (CNα2 and CNα3, respectively). In an embodiment, the siRNA comprises or targets a nucleotide sequence selected from SEQ ID NO:25, 26, 27, 28, 29, 30, 31 and 32.

Taught herein is an agent comprising a short interfering RNA (siRNA) agent or a chemically modified or mimetic form thereof which targets an mRNA species encoding α-globin at a site selected from the 5'-UTR, Exon1, Exon3, the 3'-UTR and a boundary inbetween to reduce the amount of α-globin produced for use in ameliorating the symptoms of β-thalassemia or a related hemoglobinopathy in a subject.

Enabled herein is a method for treating a human subject with β-thalassemia or a related hemoglobinopathy, the method comprising administering to the subject an amount of an siRNA targeting or comprising a nucleotide sequence selected from SEQ ID NO:42 to SEQ ID NO:572 (HBA1) and SEQ ID NO:574 to SEQ ID NO:1179 (HBA2) effective to down-regulate expression of the α-globin genetic locus for a time and under conditions sufficient to reduce levels of α-globin. Excluded from this embodiment is Hs-siα5, CNα2 and CNα3.

As taught herein, the expression "reducing expression of the α-globin genetic locus" means that levels of mRNA encoding α-globin or levels of α-globin translated from the mRNA is reduced to a level of about 30% to about 95% of the level in a cell from a subject who does not have β-thalassemia. It also includes reducing the level of α-globin produced to 30%-95% of the level in a cell from a subject without β-thalassemia. This is regarded as a "normal cell" or a "normal control" or "statistically determined normal levels". By "30% to 95%" means 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94 or 95%.

Hence, it is not the aim of the instant method to totally eliminate expression of α-globin. Rather, the intention is to reduce expression to non-zero levels. This means to a level of from 30% to 95% relative to a normal control. In an embodiment, the level of expression of the α-globin genetic locus is reduced from less than the level prior to intervention to above zero levels, thereby reducing α-globin production and normalizing α- and β-globin levels. In another embodiment, the expression of the α-globin genetic locus is reduced to a level at which equi-amounts of α-globin and β-globin are produced. In yet another embodiment, the RNAi agents are expressed in a 5'-UTR, 3'-UTR or intronic region of a β-globin nucleic acid molecule used in gene therapy to elevate β-globin levels.

The present disclosure teaches agents, such as oligonucleotides and similar species for use in reducing expression of a genetic locus or mRNA encoding human α-globin. This is accomplished by providing oligonucleotides which target or comprise at least a portion of a nucleotide sequence corresponding to α-globin mRNA. By "target" includes a sequence which is complementary to the mRNA sequence to facilitate complementary nucleotide pair binding. Hence, the oligonucleotide encompasses RNA encoding all or a portion of α-globin including pre-mRNA. In an embodiment, the agent herein induces gene silencing mechanisms such as RNAi-medicated gene silencing. The term "gene silencing" does not necessarily mean inducing zero expression but a level of expression from greater than zero expression to a level less than the level prior to intervention.

Agents taught herein include sense oligomeric compounds, sense oligonucleotides, alternate splicers, primers, probes, and other oligomeric compounds which comprise a nucleotide sequence having identity to at least a portion of mRNA encoding α-globin or complementary thereto. As such, these compounds may be introduced in the form of single-stranded, double-stranded, circular or hairpin oligomeric compounds and may contain structural elements such as internal or terminal bulges or loops as well as branches. Once introduced to a cell, the agents of the present invention may elicit the action of one or more enzymes or structural proteins or complexes to effect modification of the α-globin mRNA or α-globin genetic locus. An example of such a complex is RISC.

When in oligomeric form, the agent may be single-stranded sense oligonucleotide or double-stranded RNA (duplex) structures, such as double-stranded RNA (dsRNA) molecules or may be chemical or synthetic or mimetic forms thereof. A chemically modified form includes branched and hairpin oligonucleotides. The oligomer may be synthetically produced or derived by expression of DNA or an RNA vector system to generate short hairpin loops. In one embodiment, the DNA or RNA system can generate short hairpin RNA that specifically targets the reduction in expression of α-globin.

In the context of the method taught herein, the term "oligonucleotide" refers to an oligomer or polymer of ribonucleic acid (RNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increases stability in the presence of nucleases.

Whilst oligonucleotides are one form of the agents enabled by the present disclosure, other families of compounds are contemplated, including but not limited to oligonucleotide analogs and mimetics including chimeras with peptides referred to as "peptide oligonucleotides". The term "chimeras" also refers to oligonucleotides comprising modified internucleoside linkages between naturally occurring nucleotides.

As described above, an agent in the form of an oligonucleotide generally comprises from about 15 to about 50 nucleobases (i.e. from about 15 to about 50-linked nucleosides).

"Targeting" an oligonucleotide agent to a particular site with α-globin mRNA in the context of the present disclosure is a multi-step process and involves in one aspect base pairing of complementary strands.

The targeting process usually includes determination of at least one target region, segment, or site within the α-globin mRNA which leads to reduced but not zero expression. Within the context of the present disclosure, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites", as used in the present invention, are defined as positions within a target nucleic acid.

Alternative RNA transcripts can be produced from the same genomic region of DNA. These alternative transcripts are generally known as "variants". "Pre-mRNA variants" are transcripts produced from the same genomic DNA that differ from other transcripts produced from the same genomic DNA in either their start or stop position and contain both intronic and exonic sequence. Pre-mRNA variants of the α-globin genetic locus are contemplated herein as a target for sense-mediated gene silencing.

Target segments can include RNA sequences that comprise at least the 15 consecutive nucleobases from the 5'-terminus of the α-globin mRNA transcript. Similarly, target segments include RNA sequences that comprise at least the 15 consecutive nucleobases from the 3'-terminus of one of the α-globin mRNA transcript. The skilled artisan would, without undue experimentation, be able to identify further useful target segments. SEQ ID NO:42 through SEQ ID NO:572 and SEQ ID NO:574 to SEQ ID NO:1179 represent targets of 15 bases (15 mer's) within the α-globin mRNA. In terms of siRNA, the nucleotide sequence of a nucleotide strand of the siRNA may comprise a sequence selected from SEQ ID NO:42 to SEQ ID NO: 572 and SEQ ID NO:574 to SEQ ID NO:1179. This includes hairpin RNAs. In an embodiment, the sequence or targeted sequence is selected from SEQ ID NO:25, 26, 27, 28, 29, 30, 31 and 32.

Once one or more target regions, segments or sites have been identified, sense oligonucleotides are chosen which give the desired effect of reducing translation to α-globin protein. It is not the intention of the method to eliminate all expression of the α-globin genetic locus. It is proposed that α-globin production or gene expression be between 30% and 95% the level in a normal cell (i.e. a cell from a subject who does not have β-thalassemia).

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may, therefore, fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Examples of modified oligonucleotides useful in the present method include oligonucleotides containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone can also be considered to be oligonucleosides.

Useful modified oligonucleotide backbones containing a phosphorus atom therein include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Useful oligonucleotides having inverted polarity comprise a single 3' to 3' linkage at the 3'-most internucleotide linkage, i.e. a single inverted nucleoside residue which may be abasic (the nucleobase is missing or has a hydroxyl group in place thereof). Various salts, mixed salts and free acid forms are also included.

Useful modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulphonamide backbones; amide backbones; and others having mixed N, O, S and $CH_2$ component parts.

In other useful oligonucleotide mimetics, both the sugar and the internucleoside linkage (i.e. the backbone), of the nucleotide units are replaced with novel groups. The nucleobase units are maintained for sequence identity with the region of α-globin transcript. One such compound is referred to as a peptide oligonucleotide. In peptide oligonucleotides, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Teaching of peptide oligonucleotide compounds can be found in Nielsen et al. (1992) *Science* 254:1497-1500.

In an embodiment, oligonucleotides are provided with phosphorothioate backbones and oligonucleosides with heteroatom backbones, and in particular —$CH_2$—NH—O—$CH_2$—, —$CH_2$—N($CH_3$)—O—$CH_2$— [known as a methylene (methlimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$—.

Modified oligonucleotides may also contain one or more substituted sugar moieties. Useful oligonucleotides comprise one of the following at the 2' position: OH; F; O-, S- or N-alkyl; O-, S- or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalators, a group for improving the pharmacokinetic properties of an oligonucleotide, or a group for improving the pharmacodynamic properties of an oligonucleotide, and other substituents having similar properties. One type of modification includes 2'-methoxyethoxy (2'-O—$CH_2$—$CH_2$—$OCH_3$, also known as 2'-O-(2-methoxyethyl) or 2'-MOE) [Martin et al. (1995) *Helv. Chim. Acta*, 78:486-504] i.e. an alkoxyalkoxy group. A further preferred modification includes 2'-dimethylaminooxyethoxy, i.e. a $O(CH_2)_2ON(CH_3)_2$ group, also known as 2'-DMAOE, as described in examples herein below, and 2'-dimethylaminoethoxyethoxy (also known in the art as 2'-O-dimethylamino-ethoxy-ethyl or 2'-DMAEOE), i.e. 2'-O—$CH_2$—O—$CH_2$—N($CH_3$)$_2$.

Other modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'O—$CH_2$—CH=$CH_2$) and 2'-fluoro (2'-F). The 2'-modification may be in the arabino (up) position or ribo (down) position. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

A further useful modification of the sugar includes Locked Nucleic Acids (LNAs) in which the 2'-hydroxyl group is linked to the 3' or 4' carbon atom of the sugar ring, thereby forming a bicyclic sugar moiety. The linkage is generally a methylene (—CH$_2$-)$_n$ group bridging the 2' oxygen atom and the 4' carbon atom wherein n is 1 or 2.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pryimidines such as phenoxazine cytidine (1H-pyrimido[5,4-b] [1,4]benzoxazin-2(3H)-one), phenothiazine cytidine (1H-pyrimido[5,4-b] [1,4]benzothiazin-2(3H)-one), G-clamps such as a substituted phenoxazine cytidine (e.g. 9-(2-aminoethoxy)-H-pyrimido[5,4-b] [1,4]benzoxazin-2(3H)-one), carbazole cytidine (2H-pyrimido[4,5-b]indol-2-one), pyridoindole cytidine (H-pyrido[3',2':4,5]pyrrole[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Certain of these nucleobases are particularly useful for increasing the binding affinity of the agents of the present invention. These include 5-substituted pyrimidines, 6-azapyrimidines and N-2, N-6 and O-6 substituted purines, including 2-aminoprophyladenine, 5-prophynyluracil and 5-propynylcytosine. 5-methylcytosine substitutions have been shown to increase nucleic acid duplex stability.

Another modification of the oligonucleotides enabled herein involves chemically linking to the oligonucleotide one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of the present invention, include groups that improve uptake, distribution, metabolism or excretion of the compounds of the present invention. Conjugate moieties include but are not limited to lipid moieties such as a cholesterol moiety, cholic acid, a thioether, e.g. hexyl-S-tritylthiol, a thiocholesterol, an aliphatic chain, e.g. dodecandiol or undecyl residues, a phospholipid, e.g. di-hexadecyl-rac-glycerol or triethyl-ammonium 1,2-di-O-hexadecyl-rac-glycero-3-H-phosphonate, a polyamine or a polyethylene glycol chain, or adamantine acetic acid, a palmitoyl moiety, or an octadecylamine or hexylamino-carbonyl-oxycholeterol moiety. Oligonucleosides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

It is not necessary for all positions in a given compound to be uniformly modified, and in fact more than one of the aforementioned modifications may be incorporated in a single compound or even at a single nucleoside within an oligonucleotide.

Taught herein is sense oligonucleotides which are chimeric compounds. "Chimeric" sense oligonucleotides or "chimeras", in the context of the present method, are oligonucleotides which contain two or more chemically distinct regions, each made up of at lest one monomer unit, i.e. a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity of the target nucleic acid.

Chimeric oligonucleotides may be formed as composite structures of two or more oligonucleotides, modified oligonucleotides, oligonucleosides and/or oligonucleotide mimetics as described above.

A gene therapy approach may also be used to obtain DNA-derived or RNA-derived siRNA or other RNA species including hairpin RNAs.

A nucleic acid sequence encoding an RNA species such as siRNA may be introduced into a cell in a vector such that the nucleic acid sequence remains extrachromosomal. In such a situation, the nucleic acid sequence will be expressed by the cell from the extrachromosomal location. Alternatively, cells may be engineered by inserting the nucleic acid sequence into the chromosome. Vectors for introduction of nucleic acid sequence both for recombination and for extrachromosomal maintenance are known in the art and any suitable vector may be used. Methods for introducing nucleic acids into cells such as electroporation, calcium phosphate co-precipitation and viral transduction are known in the art.

In particular, a number of viruses have been used as nucleic acid transfer vectors or as the basis for preparing nucleic acid transfer vectors, including papovaviruses (e.g. SV40, Madzak et al. (1992) *J Gen Virol* 73:1533-1536), adenovirus (Berkner (1992) *Curr Top Microbiol Immunol* 158:39-66; Berkner et al. (1988) *BioTechniques* 6:616-629; Gorziglia and Kapikian (1992) *J Virol* 66:4407-4412; Quantin et al. (1992) *Proc Natl Acad Sci USA* 89:2581-2584; Rosenfeld et al. (1992) *Cell* 68:143-155; Wilkinson et al. (1992) *Nucleic Acids Res* 20:233-2239; Stratford-Perricaudet et al. (1990) *Hum Gene Ther* 1:241-256; Schneider et al.

(1998) *Nat Genetics* 18:180-183), vaccinia virus (Moss (1992) *Curr Top Microbiol Immunol* 158:5-38; Moss (1996) *Proc Natl Acad Sci USA* 93:11341-11348), adeno-associated virus (Muzyczka (1992) *Curr Top Microbiol Immunol* 158: 97-129; Ohi et al. (1990) *Gene* 89:279-282; Russell and Hirata (1998) *Nat Genetics* 18:323-328), herpesviruses including HSV and EBV (Margolskee (1992) *Curr Top Microbiol Immunol* 158:67-95; Johnson et al. (1992) *J Virol* 66:2952-2965; Fink et al. (1992) *Hum Gene Ther* 3:1-19; Breakefield and Geller (1987) *Mol Neurobiol* 1:339-371; Freese et al. (1990) *Biochem Pharmaco.* 40:2189-2199; Fink et al. (1996) *Ann Rev Neurosci* 19:265-287), lentiviruses (Naldini et al (1996) *Science* 272:263-267), Sindbis and Semliki Forest virus (Berglund et al. (1993) *Biotechnology* 11:916-920) and retroviruses of avian (Bandyopadhyay and Temin (1984) *Mol Cell Biol* 4:749-754; Petropoulos et al. (1992) *J Virol* 66:3391-3397), murine (Miller (1992) *Curr Top Microbiol Immunol* 158:1-24; Miller et al. (1985) *Mol Cell Biol* 5:431-437; Sorge et al. (1984) *Mol Cell Biol* 4:1730-1737; Mann and Baltimore (1985) *J Virol* 54:401-407; Miller et al. (1988) *J Virol* 62:4337-4345) and human (Shimada et al. (1991) *J Clin Invest* 88:1043-1047; Helseth et al. (1990) *J Virol* 64:2416-2420; Page et al. (1990) *J Virol* 64:5270-5276; Buchschacher and Panganiban (1982) *J Virol* 66:2731-2739) origin. Lentiviral vectors represent a particularly useful vector for gene therapy. In one embodiment, the lentivirus vector comprises a mono-cistronic vector for tissue-specific expression of an siRNA or other RNA species using a erythroid-derived polymerase (pol) II promoter.

In an embodiment, the vector contains the human β-globin gene under the control of the pol II β-globin promoter. Hairpin RNAs targeting sites on the α-globin gene or transcript can be inserted in introns or in the 3'- or 5'-UTR of the β-globin gene.

Taught herein is a vector comprising a nucleic acid molecule encoding human β-globin operably linked to a promoter and one or more nucleic acid molecules inserted in the 5'- and/or 3'-UTR region and/or intronic regions of the β-globin nucleic acid molecule encoding an RNA which targets an mRNA species encoding α-globin at a site selected from the 5' untranslated region (5'-UTR), Exon1, Exon3 and the 3'-UTR or a boundary region inbetween.

In an embodiment, the promoter is the pol II or pol III promoter.

In an embodiment, the second nucleic acid molecule encodes an RNA which targets or comprises α-globin mRNA selected from SEQ ID NO:25, 26, 27, 28, 29, 30, 31 and 32.

In an embodiment, the RNA molecules targeting the α-globin mRNA species are encoded by sequences inserted into β-globin nucleic acid molecule so as to facilitate combination therapy of providing β-globin and reducing α-globin.

Non-viral nucleic acid transfer methods are known in the art such as chemical techniques including calcium phosphate co-precipitation, mechanical techniques, for example, microinjection, membrane fusion-mediated transfer via liposomes and direct DNA uptake and receptor-mediated DNA transfer. Viral-mediated nucleic acid transfer can be combined with direct in vivo nucleic acid transfer using liposome delivery, allowing one to direct the viral vectors to particular cells. Alternatively, the retroviral vector producer cell line can be injected into particular tissue. Injection of producer cells would then provide a continuous source of vector particles.

The agent herein may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption.

The agents contemplated for use herein encompass any pharmaceutically acceptable salts, esters, or salts or such esters, or any other compound which, upon administration to a human, is capable of providing (directly or indirectly) the biologically active metabolite or residue thereof. Accordingly, for example, the disclosure if also drawn to prodrugs and pharmaceutically acceptable salts of the compounds of the invention, pharmaceutically acceptable salts of such prodrugs and other bioequivalents.

The term "prodrug" indicates a therapeutic agent that is prepared in an inactive form that is converted to an active form (i.e. drug) within the body or cells thereof by the action of endogenous enzymes or other chemicals and/or conditions. In an example, prodrug versions of the oligonucleotides described herein are prepared as SATE [(S-acetyl-2-thioethyl) phosphate] derivatives.

The term "pharmaceutically acceptable salts" refers to physiologically and pharmaceutically acceptable salts of the compounds, i.e. salts that retain the desired biological activity of the parent compound and do not impart undesired toxicological effects thereof.

Also taught herein are pharmaceutical compositions and formulations which include the agents herein described. The pharmaceutical compositions may be administered in any number of ways depending upon whether local or systemic treatment is desired and upon the area to be treated. Administration may be topical (including ophthalmic and to mucous membranes including vaginal and rectal delivery), pulmonary, e.g. by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; or intracranial, e.g. intrathecal or intraventricular, administration. Oligonucleotides with at least one 2-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations herein, which may conveniently be presented in unit dosage form, may be prepared according to conventional techniques well known in the pharmaceutical industry. Such techniques include the step of brining into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions herein may be formulated into any of many possible dosage forms such as, but not limited to, tablets, capsules, gel capsules, liquid syrups, soft gels, suppositories and enemas. The compositions herein may also be formulated a suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions include, but are not limited to, solutions, emulsions, foams and liposome-containing formulations. The pharmaceutical compositions and formulations may comprise one or more penetration enhancers, carriers, excipients or other active or inactive ingredients.

Formulations enabled herein include liposomal formulations. The term "liposome" means a vesicle composed of amphililic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged RNA molecules to form a stable complex. Liposomes that are pH-sensitive or negatively-charged are believed to entrap DNA rather than complex with it. Both cationic and non-cationic liposomes have been used to deliver RNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized withy one or more hydrophilic polymers, such as a polyethylene glycol (PEG) moiety.

In one embodiment, various penetration enhancers are employed to effect the efficient delivery of nucleic acids, such as oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e. surfactants, fatty acids, bile salts, chelating agents and non-chelating non-surfactants.

The skilled artisan will recognize that formulations are routinely designed according to their intended uses, i.e. route of administration.

Useful formulations for topical administration include those in which the oligonucleotides are in admixture with a topical delivery agent such as lipids, liposomes, fatty acids, fatty acid esters, steroids, chelating agents and surfactants. Lipids and liposomes include neutral (e.g. dioleoylphosphatidyl DOPE ethanolamine, dimyristoylphophatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, the oligonucleotides may be encapsulated within liposomes or may form complexes thereto, in particular to cationic liposomes. Alternatively, oligonucleotides may be complexed to lipids, in particular to cationic lipids.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Oral formulations include those in which oligonucleotides are administered in conjunction with one or more penetration enhancers surfactants and chelators. Useful surfactants include fatty acids and/or esters or salts thereof, bile acids and/or salts thereof.

The term "subject" as used herein includes a human subject. The human subject may be male or female and any age from infant to elderly. For animal model studies, the subject may be a non-human animal including a laboratory test animal, farm animal or primate.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients. The compositions may also be cell based or viral compositions.

The formulation of therapeutic compositions and their subsequent administration (dosing) is within the skill of those in the art. Dosing is dependent on severity and responsiveness of the β-thalassemic disease state, with the course of treatment lasting from several days to several months or years, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or even every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily, to once every 20 years.

The present disclosure is instructional on the use of an agent which reduces expression of the α-globin genetic locus in a subject in the manufacture of a medicament in the treatment of β-thalassemia or a related hemoglobinopathy.

A related embodiment teaches an agent which reduces expression of the α-globin genetic locus in a method for treating β-thalassemia or a related hemoglobinopathy.

Further enabled herein is a method for treating β-thalassemia or a related hemoglobinopathy in a human subject, the method comprising administering to the subject an siRNA molecule of from 15 to 50 bp in length which targets a region on α-globin mRNA selected from the list consisting of 5'-UTR, 3'-UTR, Exon1, Exon3 and a boundary or intronic region to thereby reduce the level of expression of the α-globin genetic locus to less than levels prior to intervention to above-zero levels, the amount of siRNA administered being effective to reduce α-globin levels to re-balance the levels of α-globin and β-globin. Targets include SEQ ID NO:42 to SEQ ID NO:572 on HBA1 and SEQ ID NO:574 to SEQ ID NO:1179 on HBA2 with the exception of Hs-siα5, CNα2 and CNα3.

Examples of siRNA include SEQ ID NO:25, 26, 27, 28, 29, 30, 31 and 32 as well as hairpin forming thereof. Another aspect enabled herein is directed to a vector comprising a nucleic acid molecule encoding human β-globin operably linked to a promoter and one or more second nucleic acid molecules inserted in the 5'-UTR and/or 3'-UTR region and/or an intron of the β-globin-encoding nucleic acid molecule which second nucleic acid molecule encodes an RNA which targets an mRNA species encoding α-globin at a site selected from the 5' untranslated region (5'-UTR), Exon1, Exon3 and the 3'-UTR or a boundary region inbetween. In an embodiment, the vector provides therapeutic levels of β-globin while reducing α-globin levels.

In an embodiment, the siRNA comprises a nucleotide sequence selected from SEQ ID NO:42 through SEQ ID NO:572 on HBA1 or SEQ ID NO:574 to SEQ ID NO:1179 on HBA2 or targets a nucleotide sequence selected from SEQ ID NO:42 through SEQ ID NO:572 or SEQ ID NO:574 to SEQ ID NO:1179.

EXAMPLES

Aspects disclosed herein are now further described by the following non-limiting Examples.

Materials and Methods

Maintenance of Cell Lines

In these studies, human erythroleukaemic K562 cells were maintained in continuous culture in Dulbecco's Modified Eagle Media (DMEM) (Sigma, Sydney, NSW, Australia) supplemented with 10% v/v fetal calf serum (FCS), 100 U/ml penicillin and 100 μg/ml streptomycin. Cells were incubated at 37° C. and passaged every 3-4 days by adding 2 ml of a confluent culture to 20 ml growth medium in an 80 cm$^2$ flask. Cells were seeded at 1×10$^5$ cells/ml 12 hours prior to transfection.

MEL cells were induced to hemoglobinize by seeding at an initial concentration of 2×10$^5$ cells per ml in DMEM containing 2% w/v DMSO (Sigma) and incubated at 37° C. After five days of hemoglobinization, cells were resuspended at 5×10$^5$ cells per ml in fresh DMEM with 2% w/v DMSO (Scher et al. (1982) *Cancer Res.* 42:1300-1306) and electroporated approximately 16 hours later.

Electroporation of Mammalian Cells

Immediately preceding electroporation, cells were washed three times with equal volumes of Opti-Mem reduced serum media (Invitrogen) and resuspended at a final concentration of 1×10$^7$ K562 cells per ml in Opti-Mem. Electroporations were performed at room temperature in 0.4 cm cuvettes (Bio-Rad, Hercules, Calif.) with 500 μl cell suspension mixed with an appropriate amount of RNA or DNA resuspended at a concentration of 1 μg/μl. Electroporations were performed on the Gene Pulser (Bio-Rad) using the following conditions: 226 Volts, 950 μF and ∞ resistance for K562 cells or 250 Volts. Cells were then cultured in 10 ml DMEM containing 10% v/v FCS.

Flow Cytometry

At various time points following transfection, cells were analysed with an LSR II flow cytometer (Becton Dickson, Franklin Lakes, Calif., USA). Briefly, 0.1-1×10$^6$ cells were washed once in PBS supplemented with 1% v/v FBS and resuspended in a final volume of 0.5 ml PBS. For the detection of eGFP reporter gene expression, analysis was performed only on live cells. Data acquisition and analysis were performed using BD FACsDiva software (Becton Dickson).

RNA Extractions

Cells were collected at appropriate time points after transfections and RNA was extracted using Tri-Reagent (Molecular Research Centre, Cincinnati, Ohio) according to manufacturer's instructions. Briefly, between 2.5-5×10$^6$ cells were collected by centrifugation and lysed in 500 μl Tri-Reagent for 5 minutes. 100 μl of chloroform was added and samples were agitated thoroughly for 30 seconds. Phase separation was achieved by centrifugation at 13,000 g for 20 minutes at 4° C. The aqueous phase was collected and RNA was precipitated by incubation with equal volume isopropanol. RNA was collected by centrifugation at 13,000 g for 10 minutes at 4° C., washed with 1 ml 75% v/v ethanol and resuspended in 50 μl nuclease-free H$_2$O. Quantity and quality of RNA was determined by spectrophotometry.

cDNA Synthesis cDNA was synthesized using SuperScript First-Strand kit (Invitrogen) according to manufacturer's instructions. In brief, 1 μg of RNA was combined with 1 μl of 0.5 μg/μl oligo (dT) primers, 1 μl 10 mM dNTPs and nuclease-free H$_2$O to a final volume of 10 μl 1 and incubated at 65° C. for 5 minutes. Reactions were placed on ice prior to the addition of 2 μl reaction buffer (200 mM Tris-HCl (pH 8.4), 500 mM KCl), 4 μl 25 mM MgCl$_2$, 2 μl 0.1 mM DTT and 1 μl RNAseOut and incubated at 42° C. for 2 minutes. Reverse transcription then proceeded with the addition of 1 μl Superscript II (50 units/μl) enzyme at 42° C. for 50 minutes followed by termination at 70° C. for 15 minutes.

Real-Time PCR

All samples were analyzed using primer sets designed using Primer Express software (Applied Biosystems, Epsom, Surrey). Reactions were performed on a 7300 Real-Time PCR System (Applied Biosystems). 25 ng of template cDNA was combined with 2 pmol of the forward primer and 2 pmol of the reverse primer and 12.5 μl SYBR Green Master Mix (Applied Biosystems) to a final volume of 25 μl. Samples were held at 50° C. for 2 minutes then 95° C. for 10 minutes followed by 40 cycles of 15 seconds at 95° C. and 1 minute at 60° C. with data collection occurring at 60° C. A final dissociation stage was performed consisting of 15 seconds at 95° C., 30 seconds at 60° C. and 15 seconds at 95° C. All reactions were performed in triplicates.

Data Analysis

Triplicate cycle threshold (Ct) values for each sample and primer pair were averaged. The Ct value is the number of cycles required for a label signal to cross the threshold (i.e. exceeds background level). The Ct level is inversely proportional to the amount of target to nucleic acid in a sample. Ct value of the gene of interest (α-globin) was subtracted from the reference gene (β-actin or β-globin) to calculate ΔCt. The formula $2^{\Delta Ct}$ was applied to give fold-difference between α-globin relative to the reference gene. Reductions of α-globin expression were determined by dividing fold-differences in experimental group against fold-differences in mock electroporated MEL cells.

Example 1

Phenotypic Improvements in β-Thalassemic Cells

One of the mechanisms by which excess α-globin chains are believed to damage erythroid progenitor cells is through the increased generation of ROS (Advani et al. (1992) supra; Schrier and Mohandas (1992) *Blood* 79:15896-1592; Schrier et al. (1989) *Blood* 74:2194-2202; Scott et al. (1993) *J Clin Invest* 91:1706-1712). Each improperly paired α-chain also carries an attached heme group and iron molecule which can be oxidized in the highly oxygenated environment of a RBC (Schrier (2002) supra). The increased ROS arising from imbalanced globin synthesis was detected by incubating cultured mouse β-KO cells with 2,7-dichlorofluorescein diacetate (DCFH) [Amer et al. (2003) *Eur J Haematol* 70:84-90; Kong et al. (2004) *J Clin Invest* 114:1457-1466, and Wannasuphaphol et al. (2005) *Ann NY Acad Sci* 1054:407-416] (FIG. 1B(i)). Levels of ROS in cultured erythroid progenitor cells from β-KO and WT mice were similar to levels detected in the peripheral RBCs from these mice, with β-KO cells generating ROS at levels double that of WT mice (FIG. 1B(i)). However, when β-KO cells were treated with siα4, the reduction in α-globin expression resulted in decreased levels of ROS and partial normalization of thalassemic phenotype as measured by DCFH fluorescence. Cells treated with 10 μg and 5 μg of siα4, which showed the greatest decrease in α-globin mRNA, also showed the greatest improvements in ROS levels with reductions of 41%±13% (P<0.05) and 26%±4% (P<0.02), respectively. In contrast, levels of DCFH fluorescence in cells treated with 1 μg and 10 μg siLuc were not significantly different from mock electroporated cells (FIG. 1B(ii)).

Most importantly, the results illustrate that reduced α-globin expression resulted in a detectable phenotypic change in thalassemic erythroid cells, decreasing ROS production to WT levels. This provides clear evidence that the heterozygous β-KO mouse is a suitable in vivo model for testing therapeutic down-regulation of α-globin. In summation, the results provide the basis for an innovative new strategy to treat β-thalassemia.

Example 2 siRNA-Mediated Reductions of Murine α-Globin

In developing a strategy to treat β-thalassemia patients, the susceptibility of human α-globin to siRNA-mediated degradation is tested.

Although α-globin is highly conserved between mouse and humans, it is difficult to isolate regions of perfect homology suitable for effective siRNA targeting in the relatively short (~500 bp) mRNA sequences. Effective siRNA design generally requires a low GC content with a GC bias towards the 5' end to maintain appropriate thermodynamic stability (Patzel (2007) *Drug Discov Today* 12:139-148). However, the α-globin gene is notoriously GC-rich (Higgs et al. (1989) *Blood* 73:1081-1104), making siRNA selection somewhat challenging. In addition, many siRNA selection guidelines recommend specific nucleotides in particular positions (Patzel (2007) supra), further limiting the available targets. Hence, siRNAs demonstrated to be effective against murine α-globin may not necessarily remain so against human sequences. Therefore, in order to maximize efficacy, siRNAs specific to human α-globin are designed and screened in an appropriate system.

The K562 cells are one of the most well characterized human erythroid cell lines. Originally derived from a patient with chronic myelogenous leukaemia (Lozzio and Lozzio (1975) *Blood* 45:321-334), these cells grow continuously in culture and display erythroid characteristics such as the expression of glycophorin A, the major sialoglycoprotein on human red cells (Anderson et al. (1979) *Int J Cancer* 23:143-147). In addition, K562 cells express low levels of hemoglobin, consistent with an early erythroid progenitor phenotype (Miller et al. (1984) *Blood* 63:195-200). The expressed globin chains are predominantly embryonic in nature, with ε β-like chains and ζ α-like chains, but some fetal hemoglobin ($\gamma_2\alpha_2$) is also produced (Rutherford et al. (1981) *Proc Natl Acad Sci USA* 78:348-352). α-Globin, therefore, is expressed at low but detectable levels, sufficient for preliminary screening experiments and previous studies using antisense (Ponnazhagan et al. (1994) *J Exp Med* 179:733-738) or ribozyme (Shen et al. (1999) *Blood Cells Mol ids* 25:361-373) strategies to reduce α-globin have also utilized K562 cells as the model system.

In this example, low doses of siRNA were electroporated into K562 cells and reductions were detected by real-time PCR at 24 and 48 hours. The siRNA's used are shown in Table 3. A total of eight siRNAs targeting human α-globin were tested in this manner and a number of these were found to be effective, generating reductions in α-globin comparable to previously tested strategies. These results identify siRNA sequences which are able to retain a high level of efficacy in primary erythroid progenitor cells.

TABLE 3 siRNA sequences

| Name | Sequence (5' to 3') | SEQ ID NO: |
|---|---|---|
| Murine siRNA sequences | | |
| si-α1 sense | r(GGAGCUGAAGCCCUGGAAA)dTdT | 1 |
| si-α1 antisense | r(UUUCCAGGGCUUCAGCUCC)dAdT | 2 |
| si-α2 sense | r(AGGUCAAGGGUCACGGCAA)dTdT | 3 |
| si-α2 antisense | r(UUGCCGUGACCCUUGACCU)dGdG | 4 |
| si-α3 sense | r(CCGUGCUGACCUCCAAGUA)dTdT | 5 |
| si-α3 antisense | r(UACUUGGAGGUCAGCACGG)dTdG | 6 |
| si-α4 sense | r(CCUCUUGGUCUUUGAAUAA)dTdT | 7 |
| si-α4 antisense | r(UUAUUCAAAGACCAAGAGG)dTdA | 8 |
| Murine shRNA oligonucleotides | | |
| pshα1 oligo FWD | GAT CCC CAT GGA GCT GAA GCC CTG GAA ATT CAA GAG | 9 |
| | ATT TCC AGG GCT TCA GCT CCA TTT TTT A | 10 |
| pshα1 oligo REV | AGC TTA AAA ATG GAG CTG AAG CCT GGA ATC TCT | 11 |
| | TGA ATT TCC AGG GCT TCA GCT CCA TGG G | 12 |

TABLE 3-continued siRNA sequences

| Name | Sequence (5' to 3') | SEQ ID NO: |
|---|---|---|
| pshα2 oligo FWD | GAT CCC CCC AGG TCA AGG GTC ACG GCA ATT CAA GAG | 13 |
| | ATT GCC GTG ACC CTT GAC CTG GTT TTT A | 14 |
| pshα2 oligo REV | AGC TTA AAA ACC AGG TCA AGG GTC ACG GCA ATC TCT | 15 |
| | TGA ATT GCC GTG ACC CTT GAC CTG GGG | 16 |
| pshα3 oligo FWD | GAT CCC CC CCG TGC TGA CCT CCA AGT ATT CAA GAG | 17 |
| | ATA CTT GGA GGT CAG CAC GGT GTT TTT A | 18 |
| pshα3 oligo REV | AGC TTA AAA ACA CCG TGC TGA CCT CCA AGT ATC TCT | 19 |
| | TGA ATA CTT GGA GGT CAG CAC GGT GGG | 20 |
| pshα4 oligo FWD | GAT CCC CTA CCT CTT GGT CTT TGA ATA ATT CAA GAG | 21 |
| | ATT ATT CAA AGA CCA AGA GGT ATT TTT A | 22 |
| pshα4 oligo REV | AGC TTA AAA ATA CCT CTT GGT CTT TGA ATA ATC TCT | 23 |
| | TGA ATT ATT CAA AGA CCA AGA GGT AGG G | 24 |

Human siRNA sequences

| Name | Sequence (5' to 3') | SEQ ID NO: |
|---|---|---|
| Hs_si-α1 sense | r(CAGACUCAGAGAGAACCCA)dTdT | 25 |
| Hs_si-α1 antisense | r(UGGGUUCUCUCUGAGUCUG)dTdG | 26 |
| Hs_si-α2 sense | r(CCGACAAGACCAACGUCAA)dTdT | 27 |
| Hs_si-α2 antisense | r(UUGACGUUGGUCUUGUCGG)dCdA | 28 |
| Hs_si-α3 sense | r(CCGUGCUGACCUCCAAAUA)dTdT | 29 |
| Hs_si-α3 antisense | r(UAUUUGGAGGUCAGCACGG)dTdG | 30 |
| Hs_si-α4 sense | r(GGCCCUUCCUGGUCUUUGA)dTdT | 31 |
| Hs_si-α4 antisense | r(UCAAAGACCAGGAAGGGCC)dGdG | 32 |
| Hs_si-α5 sense | r(GACCUACUUCCCGCACUUC)dTdT | 33 |
| Hs_si-α5 antisense | r(GAAGUGCGGGAAGUAGGUC)dTdT | 34 |
| Stealth si-α1 sense | GCCCUGGAGAGGAUGUUCCUGUCCU | 35 |
| Stealth si-α1 antisense | AGGACAGGAACAUCCUCUCCAGGGC | 36 |
| Stealth si-α2 sense | CCACCAAGACCUACUUCCCGCACUU | 37 |
| Stealth si-α2 antisense | AAGUGCGGGAAGUAGGUCUUGGUGG | 38 |
| Stealth si-α3 sense | CCGUGCUGACCUCCAAAUACCGUUA | 39 |
| Stealth si-α3 antisense | UAACGGUAUUUGGAGGUCAGCACGG | 40 |

Example 3

Human siRNA Sequences

For identifying effective siRNAs targeting human α-globin (see Table 3), a total of eight siRNA sequences were tested in K562 cells. Qiagen design algorithms were utilized to identify four sequences targeting the major α2-globin gene. Two of four siRNAs selected in this fashion were homologous to murine si-α3 and si-α4, sequences previously demonstrated to be effective in MEL cells (see FIGS. 2A and B). However, the si-α4 human homolog binds a region in the 3' UTR which differs between the human α1 and α2 globin genes. The equivalent region in the α1-globin gene was considered unsuitable for siRNA targeting as it failed to meet many of the recommended guidelines so the Hs-siα4 sequence only targets the α2-globin sequence. In addition to these pre-designed sequences, a fifth siRNA was designed against the 5' region of Exon 2. A study (Sarakul et al. (2008) supra) has reported that siRNAs targeting this region reduced α-globin expression substantially in cultured normal erythroid precursor cells so the Hs-siα5 sequence was included for comparison.

Figure 2A:
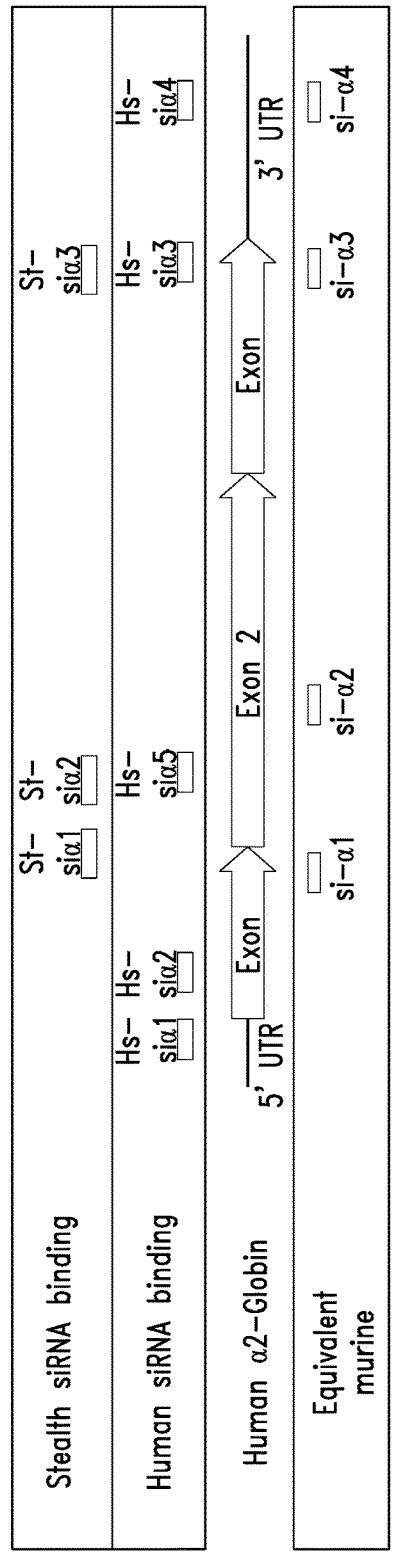
FIG. 2A is a schematic representation of dominant human α2-globin mRNA and siRNA binding sites. The human α2 and α1 globin genes are identical through the coding regions and differ only slightly in the UTRs (untranslated regions) so all siRNA sequences except Hs-siα4 target both α-globin genes. Standard siRNAs designed using Qiagen algorithms are represented in blue and a published sequence, Hs-siα5, is represented in green. The modified, 25-mer Stealth sequences are represented in red. The equivalent human homologs of previously tested murine siRNA sequences have been indicated in grey.
Figure 2B:
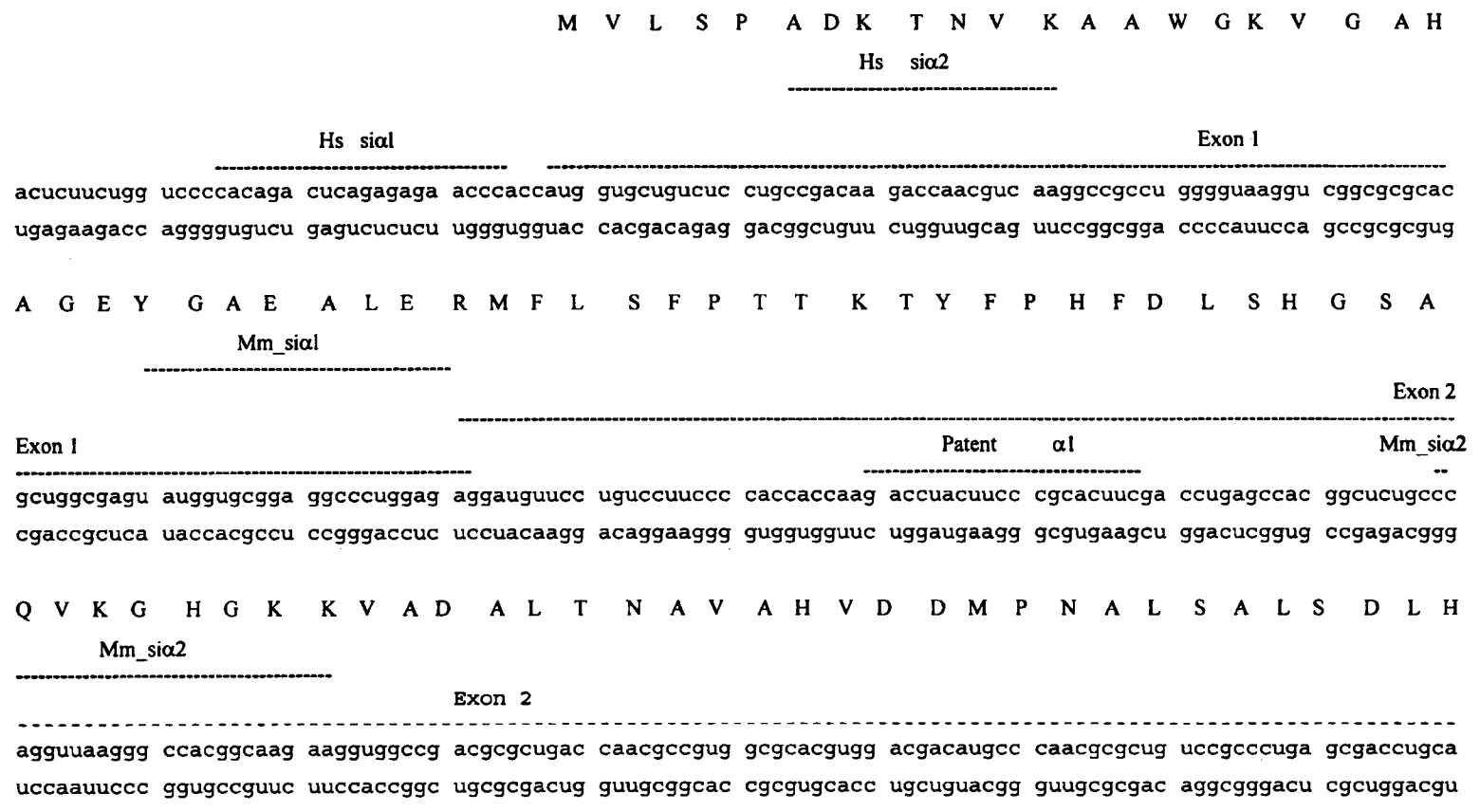

It was also of interest to investigate the effects of varying siRNA composition on silencing ability so, in addition to the five siRNAs synthesized with standard chemistries, three additional Stealth (Trade Mark) siRNAs from Invitrogen were also tested. The Stealth (Trade Mark) siRNAs are blunt-ended 25 bp dsRNA molecules chemically modified to enhance stability and minimize off target effects. As these molecules differ slightly from standard siRNAs, parameters for predicting optimal sequences also varies slightly. Nevertheless, two of the three top Stealth (Trade Mark) sequences recommended by Invitrogen's algorithms matched target sites selected for standard siRNAs (FIGS. 2A and B). The Stealth St-siα3 matched a Qiagen sequence (si-α3) while St-siα2 overlapped with the previously published si-α5 sequence.

Example 4 siRNA-Mediated Reductions of α-Globin in Human Erythroleukemic Cells

α-Globin mRNA in K562s Treated with 1 µg siRNA

As the levels of α-globin expression in K562 cells are relatively low, a small quantity of siRNA was initially utilized in order to identify the most effective sequences. 1 µg of siRNA was electroporated into $5\times10^6$ K562 cells and α-globin mRNA expression was determined at 24 and 48 hours by real-time PCR with β-actin as a loading control.

Three of the siRNA sequences tested (Hs-siα3, Hs-siα4 and Hs-siα5) had no significant effects on α-globin expression at 24 hours. Interestingly, the St-siα2 and St-siα3 Stealth sequences, which overlap with Hs-siα5 and Hs-siα3, respectively, generated significant reductions in α-globin expression compared to mock electroporated K562s. Both St-siα1 and St-siα3 reduced α-globin expression by ~50% (P<0.05) while St-siα2 generated a greater reduction of ~78%±3% (P<0.0005) at the mRNA level. However, the greatest knockdowns were observed in cells treated with 1 µg of Hs-siα1 and Hs-siα2. 1 µg of Hs-siα1 reduced α-globin expression by 90%±4% (P<0.001) while Hs-siα2 generated reductions of 85%±6% (P<0.005) [FIG. 3].

Figure 3:
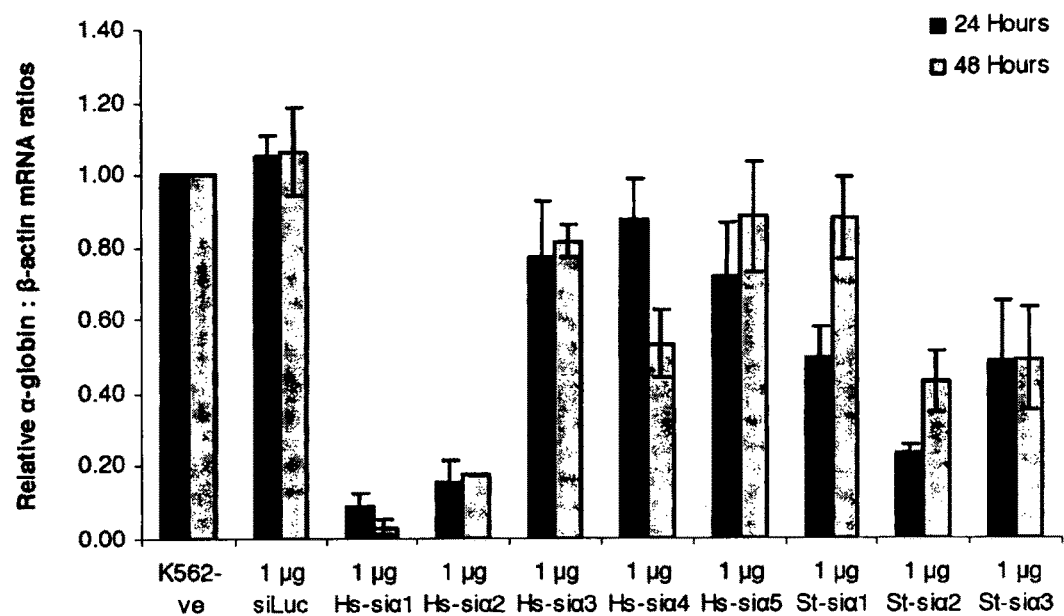
FIG. 3 is a graphical representation showing relative α-globin mRNA expression in K562 cells 24 and 48 hours post electroporation with various siRNAs targeting human α-globin. Relative α-globin RNA expression levels were detected by real-time PCR 24 and 48 hours post electroporation with 1 μg of various siRNA sequences targeted to α-globin. Relative expression of α-globin was calculated by normalizing to expression levels in mock electroporated K562 cells using β-actin expression as an RNA loading control. An siRNA sequence targeting luciferase (siLuc) was included in all experiments as an irrelevant control. Values represent the mean average of at least three independent experiments ±SD.

At 48 hours, cells treated with the Stealth sequences appeared to recover α-globin expression while standard siRNAs either retained or increased reductions. Cells treated with St-siα1 recovered fastest and were no longer significant at 48 hours. St-siα2 was also less active at 48 hours with only 57%±8% (P<0.01) reduction while St-siα3 retained the same degree of efficacy with reductions of 50%±14% (P<0.05). Hs-siα1 and Hs-siα2 both retained efficacies at 48 hours with reductions of 97%±3% (P<0.0005) and 82% (P<0.0001) respectively. Hs-siα4, which only targets α2-globin, was much more effective at 48 hours compared to 24 hours, reducing α-globin by 47%±9% (P<0.05) compared to mock electroporated cells (FIG. 3).

Example 5

α-Globin mRNA in K562s Treated with 500 ng siRNA

Figure 4:
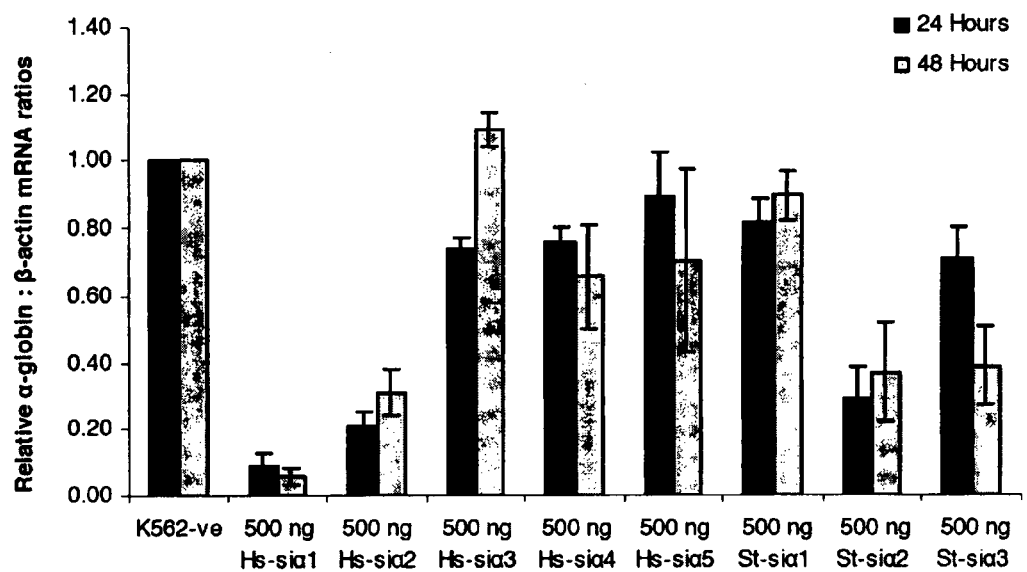
FIG. 4 is a graphical representation showing relative α-globin mRNA expression in K562 cells 24 and 48 hours post electroporation with various siRNAs targeting human α-globin. Relative α-globin RNA expression levels were detected by real-time PCR 24 and 48 hours post electroporation with 500 ng of various siRNA sequences targeted to α-globin. Relative expression of α-globin was calculated by normalizing to expression levels in mock electroporated K562 cells using β-actin expression as an RNA loading control. Values represent the mean average of at least three independent experiments ±SD.

In order to better assess the efficacy of each siRNA sequence, smaller amounts of siRNA were delivered into K562s and effects on α-globin expression was again determined by real-time PCR. At 24 hours, this lower dose of siRNA was able to clearly indicate the most effective targets. While all siRNAs except Hs-siα3 and Hs-siα5 generated significant reductions in α-globin, three of these were relatively modest. An amount of 500 ng of Hs-siα4, St-siα1 and St-siα3 reduced α-globin expression by 25%±5%, 19%±7% and 29%±10% respectively, compared to mock electroporated controls (P<0.05) [FIG. 4]. The Hs-siα1, Hs-siα2 and St-siα2 sequences previously demonstrated to be most effective were markedly more so, compared to other targets, at this lower dose. St-siα2 reduced α-globin expression by 70%±9% (P<0.01) while Hs-siα2 generated reductions of 80%±5% (P<0.005). Hs-siα1 remained most effective, reducing α-globin mRNA by 90%±4% (P<0.001) [FIG. 4]. At 48 hours, reductions mediated by St-siα1 were no longer significant but St-siα3 appeared more effective than at 24 hours, reducing α-globin by 60%±12% (P<0.05) compared to mock electroporated cells. There were no significant changes in all other sequences tested compared to results obtained at 24 hours (FIG. 4).

Example 6

Development of Vector Delivery System

Figure 5:
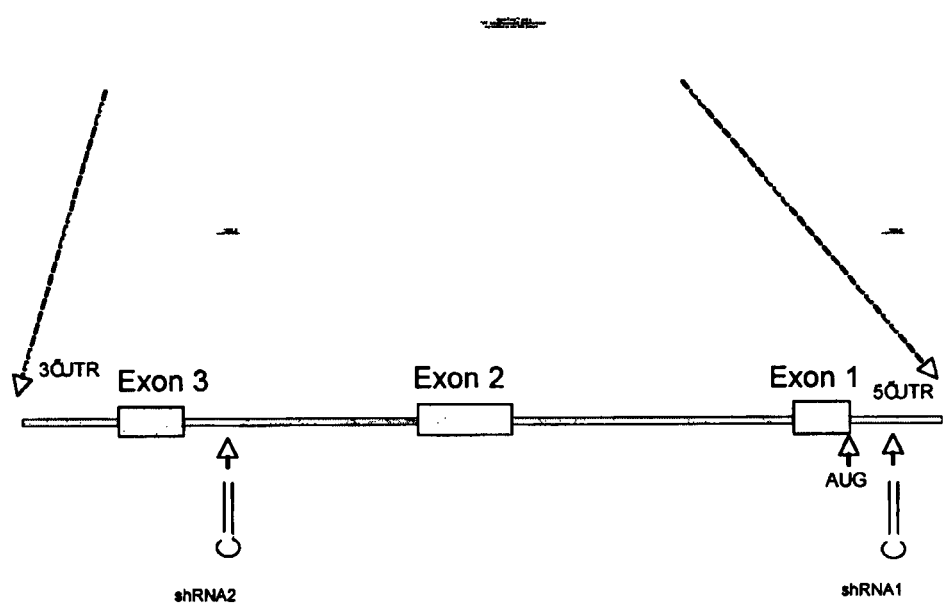
FIG. 5 is a diagrammatic representation of a lentiviral vector (LV) containing the human β0-globin gene under the control of the pol II β-globin promoter. Schematic representation of LV in its proviral form. LTR deleted of 400 bp in the HIV U3 region (LTR), rev-responsive element (RRE), splicing donor (SD) and splicing acceptor (SA) sites, human β-globin gene, β-globin promoter (p), and Dnase I-hypersensitive sites HS2 and HS3 and β-globin LCR are shown. shRNA1 and shRNA2 represent α-globin-specific shRNA insertion sites.

A mono-cistronic vector is developed for the tissue-specific expression of a short hairpin (sh)RNA from an erythroid-derived polymerase (pol) II promoter (FIG. 5). α-Globin-specific shRNAs are generated in erythroid cells. A Lentiviral (LV) β-globin vector (FIG. 5) is modified so that it expresses the shRNA sequence under an erythroid-specific pol II promoter. This means the shRNA sequence will only be produced in erythroid cells. The LV β-globin vector is modified by inserting α-globin-specific shRNA sequences within the 5'UTR or intron 2 of β-globin. This also lowers the concentration shRNA sequences required and, therefore, possible off-target effects. Additional toxicity issues may also be addressed by removing the HS2 and HS3 from β-globin LCR.

Example 7

Clinical and Animal Trials

A Lentiviral (LV) β-globin gene therapy vector (LVβ) is proposed to transfer a therapeutic β-globin transgene with high efficiency and fidelity to hematopoietic stem cells in combination with RNA-mediated silencing to reduce α-globin production. It is proposed that this approach will achieve a normal range of hemoglobin (Hb) A, i.e. 14-17 g/dL. Aspects covering the delivery of therapeutic β-globin are described in Cavazzana-Calvo et al. (2010), *Nature* 467:318-322.

Hence, this trial is based on a complementary approach of limiting α-globin gene expression by RNAi in combination with a therapeutic β-globin gene expression approach.

The LV β-globin gene therapy vector expresses a variant of normal adult $β^A$-globin ($β^{A-T87Q}$) which has a therapeutic efficiency in a β-thalassemic mouse model. The RNAi approach includes targeting α-globin mRNA at a site selected from the 5'-UTR, Exon1, Exon3, the 3'-UTR and a boundary region inbetween. In an embodiment, the RNAi approach targets or comprises a nucleotide sequence selected from SEQ ID NO:25, 26, 27, 28, 29, 30, 31 and 32.

Conveniently, the RNAi in the form of a short hairpin (sh)RNA is delivered by Lentiviral vectors (LV). In an example Lentilox 3.7 (LL3.7) is a third generation self-inactivating (SIN) LV system (Rubinson et al. (2003), *Nat. Genet* 33:401-406). RNAi expression is mediated by type III RNA polymerase (Pol III) or type II (Pol II) transcription in the form of shRNAs.

Erythroid progenitor cells extracted from the bone marrow of β-thalassemic patients are cultured for 5 days in the presence of stem cell factor (SCF), dexamethasone (Dex) and erythropoietin (Epo), a combination of factors which promotes the in vitro expansion of erythroblasts. Following expansion, cells are transduced with viral vectors at a multiplicity of infection (MOI) of 1. Replacing the proliferation factors with high concentrations of Epo and insulin induces synchronous erythroid cell differentiation. Three days post viral transduction, GFP expression is used to monitor transduction efficiency and facilitate the isolation of transduced clones by fluorescent cell sorting. The efficacy of shRNA LV vectors is determined by qRT-PCR. T RNAi LV vectors balance globin synthesis to near wild-type (WT) levels.

Restriction of RNAi delivery in a time and tissue-specific manner is critical to minimize potentially deleterious off target effects. Pol III- or Pol II-directed intronic RNAi expression systems is used. In this strategy, an RNAi is encoded within an intron of a gene that is specifically expressed in the cell type of interest. Following Pol III or Pol II RNA processing, some of the intron-derived dsRNA fragments can form mature miRNAs thereby silencing the target gene, while the exons are ligated together to form mature mRNA for protein synthesis.

For therapy, the synthesis of α- and β-globin proteins must be balanced. The use of RNAi to yield a moderate reduction in α-globin in erythroid cells requires a highly specific and lineage-restricted gene-silencing vector. An erythroid-specific expression system is the LV β-globin gene therapy vector.

An example of a LV system comprises the 5'-LTR, cPPT, RRE, the β-globin gene and one or more nucleic acid molecules encoding chicken globin hypersensitive sites 2, 3 and/or 4 (HS 2, 3, 4, respectively).

It is proposed to modify LVP gene therapy vectors by inserting α-globin-specific RNAi sequences into the intronic region of the β-globin gene. The LVP vector is based on the design detailed above and proven successful for the correction of SCD and β-thalassemic mice but with the incorporation of a number of modifications to reduce the risk of genotoxicity, including i) utilizing a self-inactivating (SIN) LV vector containing deletions in the LTRs, with complete removal of both viral enhancer and promoter region, ii) use of enhancer/promoter specific for the erythroid lineage, and iii) use of chromatin insulators from the chicken globin hypersensitive site 2, 3 and/or 4 (cHS2-4). Such insulator sites are well characterized in mammalian cells. The cHS4 enhancer blocking activity, for example, is most effective as a doublet and this is the configuration used in the LVβ vector currently under evaluation in phase I/II clinical studies.

α-Globin-specific RNAi sequences are inserted within intron II of the β-globin gene, thereby limiting the expression of α-globin in erythroid cells while the β-globin exons are spliced together to form mature mRNA for protein synthesis.

Figure 6:
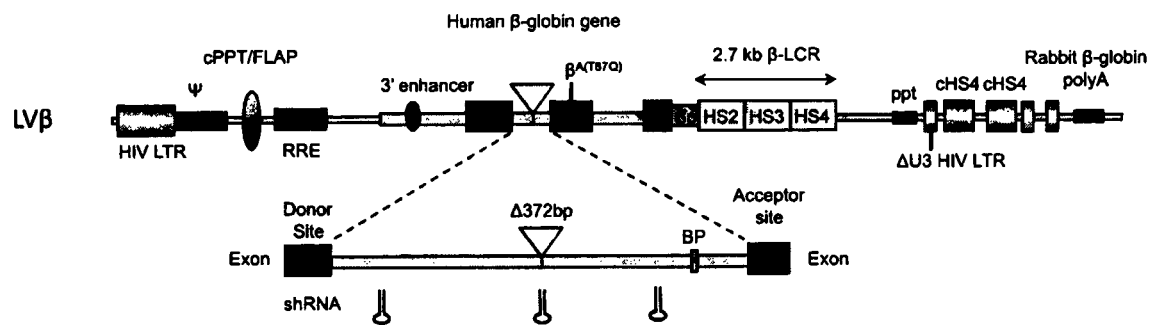
FIG. 6 is a diagrammatic representation of the LVβ vector. (A) LVβ vector encodes an adult β-globin ($β^{A(T87Q)}$) that forms functional Hb distinguishable from normal Hb by HPLC. The β-globin is placed under control of the human β-globin LCR, β-globin promoter (βp), and 3' β-globin enhancer. Intron-II is artificial, containing a 375 bp deletion to remove an A/T rich region that has been shown to reduce viral titre. Safety modifications include 2 stop codons in the Ψ packaging signal, a 400 bp deletion in the U3 of the right HIV LTR and 2×250 bp cHS4 chromatin insulators. Additional features include: central polypurine tract/DNA flap (cPPT/flap); RRE, Rev-responsive element; polypurine tract (ppt).

A clinically approved LVβ vector is modified to enable intronic delivery of α-globin-specific RNAi molecules. The level of silencing produced by the α-globin-specific shRNA is sequence-dependent, which means that sequences of variable activity can be used to fine tune α-globin levels (FIG. 6). RNAi sequences are inserted into one or more of three locations in the second intron of the β-globin gene encoded by the LVβ vector: 1) positioned near the branch point (BP), 2) inserted into the 375 bp deletion breakpoint, and 3) near the splice donor site.

Limited RNAi-mediated reduction of α-globin (by 25-50%) and β-globin transgene expression is proposed to synergise restoration of the α:β globin ratio to equal levels and restore the Hb deficit reported in several β-globin gene therapy studies. The therapeutic potential of LVβ-RNAi vectors is evaluated in two β-thalassemic transplantation models.

Model 1:

LVβ and LVβ-RNAi vectors are evaluated in intermediate β-thalassemic mice (β-KO$^{+/-}$). BM cells are isolated from β-KO$^{+/-}$ mice, transduced and transplanted into lethally irradiated β-thalassemic mice. Model 2: LVβ and LVβ-RNAi vectors are also evaluated in severe β-thalassemic (β-KO$^{-/-}$) mice. Fetal liver (FL) cells are isolated from β-KO$^{-/-}$ mice at E13.5, transduced and transplanted into lethally irradiated β-thalassemic mice.

BM and FL cells are lineage depleted using the Lineage Cell Depletion Kit (Miltenyi). This procedure generally yields lineage negative (Lin) stem cells at purities greater than 80%. Following in vitro stimulation, cells are transferred to retronectin-coated plates and transduced overnight with viral vectors. Cells are then harvested and $1×10^6$ cells injected i.v. into β-KO$^{+/-}$ recipient mice after 1100 cGY of total body irradiation. As transplantation controls, up to 10 mice per control group are transplanted with mock-transduced β-KO$^{+/-}$, β-KO$^{-/-}$ and normal cells. Additional controls include cells transduced with LV vectors with and without an irrelevant shRNA targeting sequence.

Peripheral blood is collected at several time points following BM/FL transplantation and globin synthesis assessed by qRT-PCR, primer extension and HPLC. Phenotypic correction is determined by FBE and ROS measurements. Recipient mice are euthanized 1-6 months following transplantation. BM, spleen, liver, and heart are harvested and subjected to multiple analyses. Recipient mice of mock-transduced β-KO$^{-/-}$ FL cells are anticipated to show moribund features by day 30 due to profound anemia. The degree of phenotypic correction is determined by measuring erythroblast (Ter-119$^+$/CD71$^+$) populations in the BM and spleen of treated mice. Prussian blue staining will be used to assess the level of iron deposition, which is an indirect measure of ineffective erythropoiesis. Experiments employ statistically significant numbers of animals and the two-tailed Student's t test will be used to determine statistical significance.

The effects of LVβ-RNAi vectors containing human α-globin-specific RNAi sequences are evaluated. Peripheral blood samples are drawn from healthy donors and from β-thalassemia patients. CD34+ cells are isolated by immunomagnetic cell separation using CD34 MicroBead kit (Miltenyi). Early erythroid progenitors are expanded, followed by synchronous erythroid differentiation. LVβ-RNAi vectors are introduced into cultured human erythroid progenitors and evaluated on days 1-5 following the induction of differentiation. LVβ and LVβ-RNAi gene therapy in two groups of β-thalassemia patients (HbE and IVS1-110 genotypes). HbE is common in Southeast Asia and causes 40-70% reduction of β-globin synthesis, whereas IVS1-110 is frequently observed in southern Europe resulting in 90% reduction in β-globin synthesis. α/β-Globin synthesis is assessed by qRT-PCR and by [$^3$H] leucine incorporation into globin chains. At least 5 HbE and 5 IVS1-110 patients are examined. As the clinical severity of β-thalassemia is influenced by the presence of α-thalassemia or HbF production, it is necessary to confirm the presence or absence of genetic modifiers of disease. This allows monitoring of balanced α-/non-α-globin synthesis in the β-thalassemia patients.

Those skilled in the art will appreciate that aspects described herein are susceptible to variations and modifications other than those specifically taught. It is to be understood that these aspects includes all such variations and modifications. Aspects disclosed herein include all of the steps, features, compositions and compounds, individually or collectively, and any and all combinations of any two or more of the steps or features.

BIBLIOGRAPHY

Advani et al. (1992) *Blood* 79:1064-1067
Al-Hasani et al. (2004) *Transgenic Res* 13:235-243
Amer et al. (2003) *Eur J Haematol* 70:84-90,
Anderson et al. (1979) *Int J Cancer* 23:143-147
Bandyopadhyay and Temin (1984) *Mol Cell Biol* 4:749-754
Beauchemin et al. (2004) *J Biol chem.* 279:19471-19480
Berglund et al. (1993) *Biotechnology* 11:916-920
Berkner et al. (1988) *BioTechniques* 6:616-629
Berkner (1992) *Curr Top Microbiol Immunol* 158:39-66
Breakefield and Geller (1987) *Mol Neurobiol* 1:339-371
Buchschacher and Panganiban (1982) *J Virol* 66:2731-2739
Camaschella et al. (1995) *Am J Hematol* 48:82-87
Cao et al. (1991) *Am J Pediatr Hematol Oncol.* 13:179-188
Cavazzana-Calvo et al. (2010), *Nature* 467:318-322
Fessas (1963) *Blood* 21:21-32
Fink et al. (1992) *Hum Gene Ther* 3:1-19
Fink et al. (1996) *Ann Rev Neurosci* 19:265-287
Freese et al. (1990) *Biochem Pharmaco.* 40:2189-2199
Gorziglia and Kapikian (1992) *J Virol* 66:4407-4412
Hannon (2002) *Nature* 418:244-251
Helseth et al. (1990) *J Virol* 64:2416-2420
Higgs et al. (1989) *Blood* 73:1081-1104
Johnson et al. (1992) *J Virol* 66:2952-2965
Kanavakis et al. (2004) *Blood Cells Mol Dis* 32:319-324
Kong et al. (2004) *J Clin Invest* 114:1457-1466
Lozzio and Lozzio (1975) *Blood* 45:321-334
Madzak et al. (1992) *J Gen Virol* 73:1533-1536
Mann and Baltimore (1985) *J Virol* 54:401-407
Margolskee (1992) *Curr Top Microbiol Immunol* 158:67-95
Martin et al. (1995) *Helv. Chim. Acta,* 78:486-504
Miller et al. (1984) *Blood* 63:195-200
Miller et al. (1985) *Mol Cell Biol* 5:431-437
Miller et al. (1988) *J Virol* 62:4337-4345
Miller (1992) *Curr Top Microbiol Immunol* 158:1-24
Moss (1992) *Curr Top Microbiol Immunol* 158:5-38
Moss (1996) *Proc Natl Acad Sci USA* 93:11341-11348
Muzyczka (1992) *Curr Top Microbiol Immunol* 158:97-129
Naldini et al. (1996) *Science* 272:263-267
Nielsen et al. (1992) *Science* 254:1497-1500
Ohi et al. (1990) *Gene* 89:279-282
Olivieri (1999) *N Engl J Med* 341:99-109
Page et al. (1990) *J Virol* 64:5270-5276
Paszty et al. (1995) *Nat Genet* 11:33-39
Patzel (2007) *Drug Discov Today* 12:139-148
Petropoulos et al. (1992) *J Virol* 66:3391-3397
Ponnazhagan et al. (1994) *J Exp Med* 179:733-738
Quantin et al. (1992) *Proc Natl Acad Sci USA* 89:2581-2584
Rosenfeld et al. (1992) *Cell* 68:143-155
Rubinson et al. (2003), *Nat. Genet* 33:401-406
Russell and Hirata (1998) *Nat Genetics* 18:323-328
Rutherford et al. (1981) *Proc Natl Acad Sci USA* 78:348-352
Sarakul et al. (2008) *Biochemical and Biosphysical Research Communication* 369:935-938
Scher et al. (1982) *Cancer Res.* 42:1300-1306
Schneider et al. (1998) *Nat Genetics* 18:180-183
Shimada et al. (1991) *J Clin Invest* 88:1043-1047
Schrier et al. (1989) *Blood* 74:2194-2202
Schrier and Mohandas (1992) *Blood* 79:15896-1592
Schrier (1994) *Annu Rev Med* 45:211-218
Schrier (2002) *Curr Opin Hematol* 9:123-126
Schrier et al. (2003) *Redox Rep.* 8:241-245
Scott et al. (1993) *J Clin Invest* 91:1706-1712
Shen et al. (1999) *Blood Cells Mol ids* 25:361-373
Sorge et al. (1984) *Mol Cell Biol* 4:1730-1737
Stratford-Perricaudet et al. (1990) *Hum Gene Ther* 1:241-256
Thein et al. (1984) *Br J Haematol.* 56:333-337
Thein (2005) Hematology (*Am Soc Hematol Educ Program*):31-37
Thein (2005) *Haematologica* 90:649-660
Vadolas et al. (2005) *Biochim Biophys Acta* 1728:150-162
Voon et al. (2008) *Haematologica* 93:1238-1242
Wannasuphaphol et al. (2005) *Ann NY Acad Sci* 1054:407-416
Wilkinson et al. (1992) *Nucleic Acids Res* 20:233-2239
Yang et al (1995) *Proc Natl Acad Sci USA* 92:11608-11612

The invention claimed is:

1. A method for treating a human subject with β-thalassemia or a related hemoglobinopathy, said method comprising administering to said subject an effective amount of an siRNA molecule which targets an mRNA species encoding α-globin at a site selected from the 5' untranslated region (5'-UTR) or Exon1 to thereby reduce the amount of α-globin produced to non-zero levels and ameliorate the effects of an α- and β-globin chain imbalance wherein the RNA which targets the α-globin mRNA is expressed in a 5'-UTR, 3'-UTR or intron of a nucleic acid molecule which encodes a functional β-globin and comprises SEQ ID NO: 26 or 28.

2. The method of claim 1 wherein the siRNA comprises a nucleotide strand of from 15 to 50 bp in length.

3. The method of claim 2 wherein the siRNA is a hairpin RNA or a chemically modified or mimetic form or peptide oligonucleotide form thereof.

4. The method of claim 3 wherein the chemically modified siRNA is a branched oligonucleotide.

5. The method of claim 1 wherein the level of α-globin is reduced to a level of from about 30% to 95% of the level of α-globin in a cell from a subject not suffering from β-thalassemia.

6. The method of claim 1 wherein the related hemoglobinopathy is HbE or sickle cell disease.

7. An isolated siRNA molecule which targets an mRNA species encoding a human α-globin at a site selected from the 5' untranslated region (5'-UTR) and Exon1 and which reduces the amount of α-globin produced, wherein the isolated siRNA molecule comprises SEQ ID NO: 26 or 28.

8. The isolated siRNA of claim 7 wherein the siRNA is a hairpin RNA or a chemically modified or mimetic form or peptide oligonucleotide form thereof.

9. The isolated siRNA of claim 8 wherein the modified siRNA is a branched oligonucleotide.

10. A pharmaceutical composition comprising the isolated siRNA of claim 7 and one or more pharmaceutically acceptable carriers and/or diluents.

11. A vector comprising a nucleic acid molecule encoding human β-globin operably linked to a promoter and a second nucleic acid molecule inserted in the 5'-UTR, 3'-UTR and/or an intron of the β-globin nucleic acid molecule, which second nucleic acid molecule encodes an RNA which targets an mRNA species encoding human α-globin, is from 15 to 50 bases in length and comprises a sequence selected from SEQ ID NO: 1029-1058.

12. The vector of claim 9 wherein the β-globin nucleic acid is operably linked to the pol II or pol III β-globin promoter.

13. The vector of claim 9 wherein the vector is a Lentiviral vector.

14. An isolated siRNA molecule of from 15 to 50 bases in length comprising SEQ ID NO: 26 or 28, expressed in a 5' UTR, 3'UTR or intron of a nucleic acid molecule which encodes a functional β globin.

15. A vector comprising a nucleic acid molecule encoding human β-globin operably linked to a promoter and a second nucleic acid molecule inserted in the 5'-UTR, 3'-UTR and/or an intron of the β-globin nucleic acid molecule, which second nucleic acid molecule encodes an RNA which targets an mRNA species encoding human α-globin at a site selected from the 5'-UTR and Exon 1 and comprises SEQ ID NO: 26 or 28.

16. The vector of claim 15 wherein the β-globin nucleic acid is operably linked to the pol II or pol III β-globin promoter.

17. The vector of claim 15 wherein the vector is a Lentiviral vector.

\* \* \* \* \*

SEQUENCE LISTING

```
<160> NUMBER OF SEQ ID NOS: 1181

<210> SEQ ID NO 1
<211> LENGTH: 19
<212> TYPE: RNA
<213> ORGANISM: artificial sequence
<220> FEATURE:
<223> OTHER INFORMATION: si-alpha1 sense
```

```
<400> SEQUENCE: 1
ggagcugaag cccuggaaa                                               19

<210> SEQ ID NO 2
<211> LENGTH: 19
<212> TYPE: RNA
<213> ORGANISM: artificial sequence
<220> FEATURE:
<223> OTHER INFORMATION: si-alpha1 antisense

<400> SEQUENCE: 2
uuuccagggc uucagcucc                                               19

<210> SEQ ID NO 3
<211> LENGTH: 19
<212> TYPE: RNA
<213> ORGANISM: artificial sequence
<220> FEATURE:
<223> OTHER INFORMATION: si-alpha2 sense

<400> SEQUENCE: 3
aggucaaggg ucacggcaa                                               19

<210> SEQ ID NO 4
<211> LENGTH: 19
<212> TYPE: RNA
<213> ORGANISM: artificial sequence
<220> FEATURE:
<223> OTHER INFORMATION: si-alpha2 antisense

<400> SEQUENCE: 4
uugccgugac ccuugaccu                                               19

<210> SEQ ID NO 5
<211> LENGTH: 19
<212> TYPE: RNA
<213> ORGANISM: artificial sequence
<220> FEATURE:
<223> OTHER INFORMATION: si-alpha3 sense

<400> SEQUENCE: 5
ccgugcugac cuccaagua                                               19

<210> SEQ ID NO 6
<211> LENGTH: 19
<212> TYPE: RNA
<213> ORGANISM: artificial sequence
<220> FEATURE:
<223> OTHER INFORMATION: si-alpha3 antisense

<400> SEQUENCE: 6
uacuuggagg ucagcacgg                                               19

<210> SEQ ID NO 7
<211> LENGTH: 19
<212> TYPE: RNA
<213> ORGANISM: artificial sequence
<220> FEATURE:
<223> OTHER INFORMATION: si-alpha4 sense

<400> SEQUENCE: 7
ccucuugguc uuugaauaa                                               19

<210> SEQ ID NO 8
<211> LENGTH: 19
```

```
<212> TYPE: RNA
<213> ORGANISM: artificial sequence
<220> FEATURE:
<223> OTHER INFORMATION: si-alpha4 antisense

<400> SEQUENCE: 8
uuauucaaag accaagagg                                                    19

<210> SEQ ID NO 9
<211> LENGTH: 36
<212> TYPE: DNA
<213> ORGANISM: artificial sequence
<220> FEATURE:
<223> OTHER INFORMATION: pshalpha1 oligo

<400> SEQUENCE: 9 gatcccatg gagctgaagc cctggaaatt caagag                                  36

<210> SEQ ID NO 10
<211> LENGTH: 28
<212> TYPE: DNA
<213> ORGANISM: artificial sequence
<220> FEATURE:
<223> OTHER INFORMATION: pshalpha1 oligo FWD

<400> SEQUENCE: 10
atttccaggg cttcagctcc attttta                                           28

<210> SEQ ID NO 11
<211> LENGTH: 36
<212> TYPE: DNA
<213> ORGANISM: artificial sequence
<220> FEATURE:
<223> OTHER INFORMATION: phsalpha1 oligo

<400> SEQUENCE: 11
agcttaaaaa atggagctga agccctggaa atctct                                 36

<210> SEQ ID NO 12
<211> LENGTH: 28
<212> TYPE: DNA
<213> ORGANISM: artificial sequence
<220> FEATURE:
<223> OTHER INFORMATION: pshalpha1 oligo REV

<400> SEQUENCE: 12
tgaatttcca gggcttcagc tccatggg                                          28

<210> SEQ ID NO 13
<211> LENGTH: 36
<212> TYPE: DNA
<213> ORGANISM: artificial sequence
<220> FEATURE:
<223> OTHER INFORMATION: pshalpha2 oligo

<400> SEQUENCE: 13 gatccccca ggtcaagggt cacggcaatt caagag                                  36

<210> SEQ ID NO 14
<211> LENGTH: 28
<212> TYPE: DNA
<213> ORGANISM: artificial sequence
<220> FEATURE:
<223> OTHER INFORMATION: pshalpha2 oligo FWD

<400> SEQUENCE: 14
```

```
attgccgtga cccttgacct ggttttta                                          28

<210> SEQ ID NO 15
<211> LENGTH: 36
<212> TYPE: DNA
<213> ORGANISM: artificial sequence
<220> FEATURE:
<223> OTHER INFORMATION: pshalpha2 oligo

<400> SEQUENCE: 15
agcttaaaaa ccaggtcaag ggtcacggca atctct                                 36

<210> SEQ ID NO 16
<211> LENGTH: 28
<212> TYPE: DNA
<213> ORGANISM: artificial sequence
<220> FEATURE:
<223> OTHER INFORMATION: pshalpha2 oligo REV

<400> SEQUENCE: 16
tgaattgccg tgaccctctga cctgggggg                                        28

<210> SEQ ID NO 17
<211> LENGTH: 35
<212> TYPE: DNA
<213> ORGANISM: artificial sequence
<220> FEATURE:
<223> OTHER INFORMATION: pshalpha3 oligo

<400> SEQUENCE: 17
gatccccccc gtgctgacct ccaagtattc aagag                                  35

<210> SEQ ID NO 18
<211> LENGTH: 28
<212> TYPE: DNA
<213> ORGANISM: artificial sequence
<220> FEATURE:
<223> OTHER INFORMATION: pshalpha3 oligo FWD

<400> SEQUENCE: 18
atacttggag gtcagcacgg tgttttta                                          28

<210> SEQ ID NO 19
<211> LENGTH: 36
<212> TYPE: DNA
<213> ORGANISM: artificial sequence
<220> FEATURE:
<223> OTHER INFORMATION: pshalpha3 oligo

<400> SEQUENCE: 19
agcttaaaaa caccgtgctg acctccaagt atctct                                 36

<210> SEQ ID NO 20
<211> LENGTH: 28
<212> TYPE: DNA
<213> ORGANISM: artificial sequence
<220> FEATURE:
<223> OTHER INFORMATION: pshalpha3 oligo REV

<400> SEQUENCE: 20
tgaatacttg gaggtcagca cggtgggg                                          28

<210> SEQ ID NO 21
<211> LENGTH: 36
<212> TYPE: DNA
<213> ORGANISM: artificial sequence
```

```
<220> FEATURE:
<223> OTHER INFORMATION: pshalpha4 oligo

<400> SEQUENCE: 21
gatcccctac ctcttggtct ttgaataatt caagag                           36

<210> SEQ ID NO 22
<211> LENGTH: 28
<212> TYPE: DNA
<213> ORGANISM: artificial sequence
<220> FEATURE:
<223> OTHER INFORMATION: pshalpha4 oligo FWD

<400> SEQUENCE: 22
attattcaaa gaccaagagg tattttta                                    28

<210> SEQ ID NO 23
<211> LENGTH: 36
<212> TYPE: DNA
<213> ORGANISM: artificial sequence
<220> FEATURE:
<223> OTHER INFORMATION: pshalpha4 oligo

<400> SEQUENCE: 23
agcttaaaaa tacctcttgg tctttgaata atctct                           36

<210> SEQ ID NO 24
<211> LENGTH: 28
<212> TYPE: DNA
<213> ORGANISM: artificial sequence
<220> FEATURE:
<223> OTHER INFORMATION: pshalpha4 oligo REV

<400> SEQUENCE: 24
tgaattattc aaagaccaag aggtaggg                                    28

<210> SEQ ID NO 25
<211> LENGTH: 19
<212> TYPE: RNA
<213> ORGANISM: artificial sequence
<220> FEATURE:
<223> OTHER INFORMATION: Hs si-alpha1 sense

<400> SEQUENCE: 25
cagacucaga gagaaccca                                              19

<210> SEQ ID NO 26
<211> LENGTH: 19
<212> TYPE: RNA
<213> ORGANISM: artificial sequence
<220> FEATURE:
<223> OTHER INFORMATION: Hs si-alpha1 antisense

<400> SEQUENCE: 26
uggguucucu cugagucug                                              19

<210> SEQ ID NO 27
<211> LENGTH: 19
<212> TYPE: RNA
<213> ORGANISM: artificial sequence
<220> FEATURE:
<223> OTHER INFORMATION: Hs si-alpha2 sense

<400> SEQUENCE: 27
ccgacaagac caacgucaa                                              19
```

<210> SEQ ID NO 28
<211> LENGTH: 19
<212> TYPE: RNA
<213> ORGANISM: artificial sequence
<220> FEATURE:
<223> OTHER INFORMATION: Hs sialpha2 antisense

<400> SEQUENCE: 28
uugacguugg ucuugucgg                                               19

<210> SEQ ID NO 29
<211> LENGTH: 19
<212> TYPE: RNA
<213> ORGANISM: artificial sequence
<220> FEATURE:
<223> OTHER INFORMATION: Hs si-alpha3 sense

<400> SEQUENCE: 29
ccgugcugac cuccaaaua                                               19

<210> SEQ ID NO 30
<211> LENGTH: 19
<212> TYPE: RNA
<213> ORGANISM: artificial sequence
<220> FEATURE:
<223> OTHER INFORMATION: Hs si-alpha3 antisense

<400> SEQUENCE: 30
uauuuggagg ucagcacgg                                               19

<210> SEQ ID NO 31
<211> LENGTH: 19
<212> TYPE: RNA
<213> ORGANISM: artificial sequence
<220> FEATURE:
<223> OTHER INFORMATION: Hs si-alpha4 sense

<400> SEQUENCE: 31
ggcccuuccu ggucuuuga                                               19

<210> SEQ ID NO 32
<211> LENGTH: 19
<212> TYPE: RNA
<213> ORGANISM: artificial sequence
<220> FEATURE:
<223> OTHER INFORMATION: Hs si-alpha4 antisense

<400> SEQUENCE: 32
ucaaagacca ggaagggcc                                               19

<210> SEQ ID NO 33
<211> LENGTH: 19
<212> TYPE: RNA
<213> ORGANISM: artificial sequence
<220> FEATURE:
<223> OTHER INFORMATION: Hs si-alpha5 sense

<400> SEQUENCE: 33
gaccuacuuc ccgcacuuc                                               19

<210> SEQ ID NO 34
<211> LENGTH: 19
<212> TYPE: RNA
<213> ORGANISM: artificial sequence
<220> FEATURE:
<223> OTHER INFORMATION: Hs si-alpha5 antisense

<400> SEQUENCE: 34
gaagugcggg aaguagguc                                                    19

<210> SEQ ID NO 35
<211> LENGTH: 25
<212> TYPE: RNA
<213> ORGANISM: artificial sequence
<220> FEATURE:
<223> OTHER INFORMATION: Stealth si-alpha1 sense

<400> SEQUENCE: 35
gcccuggaga ggauguuccu guccu                                             25

<210> SEQ ID NO 36
<211> LENGTH: 25
<212> TYPE: RNA
<213> ORGANISM: artificial sequence
<220> FEATURE:
<223> OTHER INFORMATION: Stealth si-alpha1 antisense

<400> SEQUENCE: 36
aggacaggaa cauccucucc agggc                                             25

<210> SEQ ID NO 37
<211> LENGTH: 25
<212> TYPE: RNA
<213> ORGANISM: artificial sequence
<220> FEATURE:
<223> OTHER INFORMATION: Stealth si-alpha2 sense

<400> SEQUENCE: 37
ccaccaagac cuacuucccg cacuu                                             25

<210> SEQ ID NO 38
<211> LENGTH: 25
<212> TYPE: RNA
<213> ORGANISM: artificial sequence
<220> FEATURE:
<223> OTHER INFORMATION: Stealth si-alpha2 antisense

<400> SEQUENCE: 38
aagugcggga aguaggucuu ggugg                                             25

<210> SEQ ID NO 39
<211> LENGTH: 25
<212> TYPE: RNA
<213> ORGANISM: artificial sequence
<220> FEATURE:
<223> OTHER INFORMATION: Stealth si-alpha3 sense

<400> SEQUENCE: 39
ccgugcugac cuccaaauac cguua                                             25

<210> SEQ ID NO 40
<211> LENGTH: 25
<212> TYPE: DNA
<213> ORGANISM: artificial sequence
<220> FEATURE:
<223> OTHER INFORMATION: Stealth si-alpha3 antisense

<400> SEQUENCE: 40
uaacgguauu uggaggucag cacgg                                             25

<210> SEQ ID NO 41

```
<211> LENGTH: 574
<212> TYPE: RNA
<213> ORGANISM: artificial sequence
<220> FEATURE:
<223> OTHER INFORMATION: Nucleotide sequence of hemoglobin alpha1 (HBA1)
      mRNA

<400> SEQUENCE: 41
acucuucugg uccccacaga cucagagaga acccaccaug gugcugucuc cugccgacaa    60
gaccaacguc aaggccgccu gggguaaggu cggcgcgcac gcuggcgagu augguugcgga  120 ggcccuggag aggauguucc uguccuuccc caccaccaag accuacuucc cgcacuucga   180
ccugagccac ggcucugccc agguuaaggg ccacggcaag aagguggccg acgcgcugac   240
caacgccgug gcgcacgugg acgacaugcc caacgcgcug ccgcccuga gcgaccugca    300 cgcgcacaag cuucggguugg acccggucaa cuucaagcuc cuaagccacu gccugcuggu  360
gacccuggcc gcccaccucc ccgccgaguu caccccugcg gugcacgccu cccuggacaa   420 guuccggcu ucugugagca ccgugcugac cuccaaauac cguuaagcug gagccucggu    480
agccguuccu ccugccgcug ggcccuccaa cgggcccucc uccccuccuu gcaccggccc   540
uuccuggucu uugaauaaag ucugaguggg cggc                               574

<210> SEQ ID NO 42
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 42
acucuucugg uccccc                                                    15

<210> SEQ ID NO 43
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 43
cucuucuggu cccca                                                     15

<210> SEQ ID NO 44
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 44
ucuucugguc cccac                                                     15

<210> SEQ ID NO 45
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 45
```
cuucuggucc ccaca                                                    15

<210> SEQ ID NO 46
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 46
uucugguccc cacag                                                    15

<210> SEQ ID NO 47
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 47
ucgguccccc acaga                                                    15

<210> SEQ ID NO 48
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 48
cgguccccca cagac                                                    15

<210> SEQ ID NO 49
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 49
ugguccccac agacu                                                    15

<210> SEQ ID NO 50
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 50
gguccccaca gacuc                                                    15

<210> SEQ ID NO 51
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 51
guccccacag acuca                                                    15

<210> SEQ ID NO 52
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 52
uccccacaga cucag                                                      15

<210> SEQ ID NO 53
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 53
ccccacagac ucaga                                                      15

<210> SEQ ID NO 54
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 54
cccacagacu cagag                                                      15

<210> SEQ ID NO 55
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 55
ccacagacuc agaga                                                      15

<210> SEQ ID NO 56
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 56
cacagacuca gagag                                                      15

<210> SEQ ID NO 57
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 57
acagacucag agaga                                                      15

```
<210> SEQ ID NO 58
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 58
cagacucaga gagaa                                                        15

<210> SEQ ID NO 59
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 59
agacucagag agaac                                                        15

<210> SEQ ID NO 60
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 60
gacucagaga gaacc                                                        15

<210> SEQ ID NO 61
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 61
acucagagag aaccc                                                        15

<210> SEQ ID NO 62
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 62
cucagagaga accca                                                        15

<210> SEQ ID NO 63
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 63
ucagagagaa cccac                                                        15
```

<210> SEQ ID NO 64
<211> LENGTH: 15
<212> TYPE: DNA
<213> ORGANISM: artificial sequence
<220> FEATURE:
<223> OTHER INFORMATION: 15mer sense oligonucelotides which represent targets on HBA1 mRNA

<400> SEQUENCE: 64
cagagagaac ccacc                15

<210> SEQ ID NO 65
<211> LENGTH: 15
<212> TYPE: DNA
<213> ORGANISM: artificial sequence
<220> FEATURE:
<223> OTHER INFORMATION: 15mer sense oligonucelotides which represent targets on HBA1 mRNA

<400> SEQUENCE: 65
agagagaacc cacca                15

<210> SEQ ID NO 66
<211> LENGTH: 15
<212> TYPE: RNA
<213> ORGANISM: artificial sequence
<220> FEATURE:
<223> OTHER INFORMATION: 15mer sense oligonucelotides which represent targets on HBA1 mRNA

<400> SEQUENCE: 66
gagagaaccc accau                15

<210> SEQ ID NO 67
<211> LENGTH: 15
<212> TYPE: RNA
<213> ORGANISM: artificial sequence
<220> FEATURE:
<223> OTHER INFORMATION: 15mer sense oligonucelotides which represent targets on HBA1 mRNA

<400> SEQUENCE: 67
agagaaccca ccaug                15

<210> SEQ ID NO 68
<211> LENGTH: 15
<212> TYPE: RNA
<213> ORGANISM: artificial sequence
<220> FEATURE:
<223> OTHER INFORMATION: 15mer sense oligonucelotides which represent targets on HBA1 mRNA

<400> SEQUENCE: 68
gagaacccac caugg                15

<210> SEQ ID NO 69
<211> LENGTH: 15
<212> TYPE: RNA
<213> ORGANISM: artificial sequence
<220> FEATURE:
<223> OTHER INFORMATION: 15mer sense oligonucelotides which represent targets on HBA1 mRNA

<400> SEQUENCE: 69
agaacccacc auggu                15

<210> SEQ ID NO 70

-continued

```
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 70
gaacccacca uggug                                                      15

<210> SEQ ID NO 71
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 71
aacccaccau ggugc                                                      15

<210> SEQ ID NO 72
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 72
acccaccaug gugcu                                                      15

<210> SEQ ID NO 73
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 73
cccaccaugg ugcug                                                      15

<210> SEQ ID NO 74
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 74
ccaccauggu gcugu                                                      15

<210> SEQ ID NO 75
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 75
caccauggug cuguc                                                      15

<210> SEQ ID NO 76
<211> LENGTH: 15
```

```
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 76
accauggugc ugucu                                                15

<210> SEQ ID NO 77
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 77
ccauggugcu gucuc                                                15

<210> SEQ ID NO 78
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 78
cauggugcug ucucc                                                15

<210> SEQ ID NO 79
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 79
auggugcugu cuccu                                                15

<210> SEQ ID NO 80
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 80
uggugcuguc uccug                                                15

<210> SEQ ID NO 81
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 81
ggugcugucu ccugc                                                15

<210> SEQ ID NO 82
<211> LENGTH: 16
<212> TYPE: RNA
```

```
<213> ORGANISM: artificial sequence
<220> FEATURE:
<223> OTHER INFORMATION: 15mer sense oligonucelotides which represent
      targets on HBA1 mRNA

<400> SEQUENCE: 82
gugcugucuc cugccg                                                     16

<210> SEQ ID NO 83
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 83
ugcugucucc ugccg                                                      15

<210> SEQ ID NO 84
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 84
gcugucuccu gccga                                                      15

<210> SEQ ID NO 85
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 85 cugucccug ccgac                                                       15

<210> SEQ ID NO 86
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 86 ugucccugc cgaca                                                       15

<210> SEQ ID NO 87
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 87 gucccugcc gacaa                                                       15

<210> SEQ ID NO 88
<211> LENGTH: 15
<212> TYPE: RNA
<213> ORGANISM: artificial sequence
```

```
<220> FEATURE:
<223> OTHER INFORMATION: 15mer sense oligonucelotides which represent
      targets on HBA1 mRNA

<400> SEQUENCE: 88
ucuccugccg acaag                                                          15

<210> SEQ ID NO 89
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 89
cuccugccga caaga                                                          15

<210> SEQ ID NO 90
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 90
uccugccgac aagac                                                          15

<210> SEQ ID NO 91
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 91
ccugccgaca agacc                                                          15

<210> SEQ ID NO 92
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 92
cugccgacaa gacca                                                          15

<210> SEQ ID NO 93
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 93
ugccgacaag accaa                                                          15

<210> SEQ ID NO 94
<211> LENGTH: 15
<212> TYPE: RNA
<213> ORGANISM: artificial sequence
<220> FEATURE:
```

```
<223> OTHER INFORMATION: 15mer sense oligonucelotides which represent
      targets on HBA1 mRNA

<400> SEQUENCE: 94
gccgacaaga ccaac                                                         15

<210> SEQ ID NO 95
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 95
ccgacaagac caacg                                                         15

<210> SEQ ID NO 96
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 96
cgacaagacc aacgu                                                         15

<210> SEQ ID NO 97
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 97
gacaagacca acguc                                                         15

<210> SEQ ID NO 98
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 98
acaagaccaa cguca                                                         15

<210> SEQ ID NO 99
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 99
caagaccaac gucaa                                                         15

<210> SEQ ID NO 100
<211> LENGTH: 15
<212> TYPE: RNA
<213> ORGANISM: artificial sequence
<220> FEATURE:
<223> OTHER INFORMATION: 15mer sense oligonucelotides which represent
``` targets on HBA1 mRNA

<400> SEQUENCE: 100
aagaccaacg ucaag                                                       15

<210> SEQ ID NO 101
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 101
agaccaacgu caagg                                                       15

<210> SEQ ID NO 102
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 102
gaccaacguc aaggc                                                       15

<210> SEQ ID NO 103
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 103
accaacguca aggcc                                                       15

<210> SEQ ID NO 104
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 104
ccaacgucaa ggccg                                                       15

<210> SEQ ID NO 105
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 105
caacgucaag gccgc                                                       15

<210> SEQ ID NO 106
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 106
aacgucaagg ccgcc                                                    15

<210> SEQ ID NO 107
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 107
acgucaaggc cgccu                                                    15

<210> SEQ ID NO 108
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 108
cgucaaggcc gccug                                                    15

<210> SEQ ID NO 109
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 109
gucaaggccg ccugg                                                    15

<210> SEQ ID NO 110
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 110
ucaaggccgc cuggg                                                    15

<210> SEQ ID NO 111
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 111
caaggccgcc ugggg                                                    15

<210> SEQ ID NO 112
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 112
aaggccgccu ggggu                                                15

<210> SEQ ID NO 113
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 113
aggccgccug gggua                                                15

<210> SEQ ID NO 114
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 114
ggccgccugg gguaa                                                15

<210> SEQ ID NO 115
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 115
gccgccuggg guaag                                                15

<210> SEQ ID NO 116
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 116
ccgccugggg uaagg                                                15

<210> SEQ ID NO 117
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 117
cgccuggggu aaggu                                                15

<210> SEQ ID NO 118
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 118

```
gccuggggua agguc                                                          15
```

<210> SEQ ID NO 119
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 119

```
ccugggguaa ggucg                                                          15
```

<210> SEQ ID NO 120
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 120

```
cuggggua ag gucgg                                                         15
```

<210> SEQ ID NO 121
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 121

```
uggggua agg ucggc                                                         15
```

<210> SEQ ID NO 122
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 122

```
gggguaaggu cggcg                                                          15
```

<210> SEQ ID NO 123
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 123

```
ggguaagguc ggcgc                                                          15
```

<210> SEQ ID NO 124
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 124
gguaaggucg gcgcg                                                  15

<210> SEQ ID NO 125
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 125
guaaggucgg cgcgc                                                  15

<210> SEQ ID NO 126
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 126
uaaggucggc gcgca                                                  15

<210> SEQ ID NO 127
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 127
aaggucggcg cgcac                                                  15

<210> SEQ ID NO 128
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 128
aggucggcgc gcacg                                                  15

<210> SEQ ID NO 129
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 129
ggucggcgcg cacgc                                                  15

<210> SEQ ID NO 130
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 130
gucggcgcgc acgcu                                                  15

<210> SEQ ID NO 131
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 131
ucggcgcgca cgcug                                                        15

<210> SEQ ID NO 132
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 132
cggcgcgcac gcugg                                                        15

<210> SEQ ID NO 133
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 133
ggcgcgcacg cuggc                                                        15

<210> SEQ ID NO 134
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 134
gcgcgcacgc uggcg                                                        15

<210> SEQ ID NO 135
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 135
cgcgcacgcu ggcga                                                        15

<210> SEQ ID NO 136
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 136
gcgcacgcug gcgag                                                        15

<210> SEQ ID NO 137
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 137
cgcacgcugg cgagu                                                     15

<210> SEQ ID NO 138
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 138
gcacgcuggc gagua                                                     15

<210> SEQ ID NO 139
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 139
cacgcuggcg aguau                                                     15

<210> SEQ ID NO 140
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 140
acgcuggcga guaug                                                     15

<210> SEQ ID NO 141
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 141
cgcuggcgag uaugg                                                     15

<210> SEQ ID NO 142
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 142
gcuggcgagu auggu                                                     15

```
<210> SEQ ID NO 143
<211> LENGTH: 13
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 143
cuggcgagua ugg                                                          13

<210> SEQ ID NO 144
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 144
uggcgaguau ggugc                                                        15

<210> SEQ ID NO 145
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 145
ggcgaguaug gugcg                                                        15

<210> SEQ ID NO 146
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 146
gcgaguaugg ugcgg                                                        15

<210> SEQ ID NO 147
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 147
cgaguauggu gcgga                                                        15

<210> SEQ ID NO 148
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 148
gaguauggug cggag                                                        15

<210> SEQ ID NO 149
```

```
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 149
aguauggugc ggagg                                                       15

<210> SEQ ID NO 150
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 150
guauggugcg gaggc                                                       15

<210> SEQ ID NO 151
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 151
uauggugcgg aggcc                                                       15

<210> SEQ ID NO 152
<211> LENGTH: 16
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 152
auggugcgga ggcccu                                                      16

<210> SEQ ID NO 153
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 153
uggugcggag gcccu                                                       15

<210> SEQ ID NO 154
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 154
ggugcggagg cccug                                                       15

<210> SEQ ID NO 155
<211> LENGTH: 15
```

```
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 155
gugcggaggc ccugg                                                      15

<210> SEQ ID NO 156
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 156
ugcggaggcc cugga                                                      15

<210> SEQ ID NO 157
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 157
gcggaggccc uggag                                                      15

<210> SEQ ID NO 158
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 158
cggaggcccu ggaga                                                      15

<210> SEQ ID NO 159
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 159
ggaggcccug gagag                                                      15

<210> SEQ ID NO 160
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 160
gaggcccugg agagg                                                      15

<210> SEQ ID NO 161
<211> LENGTH: 12
<212> TYPE: RNA
```

```
<213> ORGANISM: artificial sequence
<220> FEATURE:
<223> OTHER INFORMATION: 15mer sense oligonucelotides which represent
      targets on HBA1 mRNA

<400> SEQUENCE: 161
aggcccugga ga                                                          12

<210> SEQ ID NO 162
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 162
ggcccuggag aggau                                                       15

<210> SEQ ID NO 163
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 163
gcccuggaga ggaug                                                       15

<210> SEQ ID NO 164
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 164
cccuggagag gaugu                                                       15

<210> SEQ ID NO 165
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 165
ccuggagagg auguu                                                       15

<210> SEQ ID NO 166
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 166
cuggagagga uguuc                                                       15

<210> SEQ ID NO 167
<211> LENGTH: 15
<212> TYPE: RNA
<213> ORGANISM: artificial sequence
```

```
<220> FEATURE:
<223> OTHER INFORMATION: 15mer sense oligonucelotides which represent
      targets on HBA1 mRNA

<400> SEQUENCE: 167
uggagaggau guucc                                                      15

<210> SEQ ID NO 168
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 168
ggagaggaug uuccu                                                      15

<210> SEQ ID NO 169
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 169
gagaggaugu uccug                                                      15

<210> SEQ ID NO 170
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 170
agaggauguu ccugu                                                      15

<210> SEQ ID NO 171
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 171
gaggauguuc cuguc                                                      15

<210> SEQ ID NO 172
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 172
aggauguucc ugucc                                                      15

<210> SEQ ID NO 173
<211> LENGTH: 15
<212> TYPE: RNA
<213> ORGANISM: artificial sequence
<220> FEATURE:
```

```
<223> OTHER INFORMATION: 15mer sense oligonucelotides which represent
      targets on HBA1 mRNA

<400> SEQUENCE: 173
ggauguuccu guccu                                                    15

<210> SEQ ID NO 174
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 174 gauguccug uccuu                                                     15

<210> SEQ ID NO 175
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 175 auguccugu ccuuc                                                     15

<210> SEQ ID NO 176
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 176 uguccuguc cuucc                                                     15

<210> SEQ ID NO 177
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 177 guccuguc uuccc                                                      15

<210> SEQ ID NO 178
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 178
uuccuguccu ucccc                                                    15

<210> SEQ ID NO 179
<211> LENGTH: 15
<212> TYPE: RNA
<213> ORGANISM: artificial sequence
<220> FEATURE:
<223> OTHER INFORMATION: 15mer sense oligonucelotides which represent
``` targets on HBA1 mRNA

<400> SEQUENCE: 179
uccuguccuu cccca                                                15

<210> SEQ ID NO 180
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 180
cuguccuucc ccacc                                                15

<210> SEQ ID NO 181
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 181
uguccuuccc cacca                                                15

<210> SEQ ID NO 182
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 182
guccuucccc accac                                                15

<210> SEQ ID NO 183
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 183
uccuucccca ccacc                                                15

<210> SEQ ID NO 184
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 184
ccuuccccac cacca                                                15

<210> SEQ ID NO 185
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 185
cuuccccacc accaa                                                      15

<210> SEQ ID NO 186
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 186
uuccccacca ccaag                                                      15

<210> SEQ ID NO 187
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 187
uccccaccac caaga                                                      15

<210> SEQ ID NO 188
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 188
ccccaccacc aagac                                                      15

<210> SEQ ID NO 189
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 189
cccaccacca agacc                                                      15

<210> SEQ ID NO 190
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 190
ccaccaccaa gaccu                                                      15

<210> SEQ ID NO 191
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

```
<400> SEQUENCE: 191
caccaccaag accua                                                    15

<210> SEQ ID NO 192
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 192
accaccaaga ccuac                                                    15

<210> SEQ ID NO 193
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 193
ccaccaagac cuacu                                                    15

<210> SEQ ID NO 194
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 194
caccaagacc uacuu                                                    15

<210> SEQ ID NO 195
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 195
accaagaccu acuuc                                                    15

<210> SEQ ID NO 196
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 196
ccaagaccua cuucc                                                    15

<210> SEQ ID NO 197
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 197
```
caagaccuac uuccc                                                    15

<210> SEQ ID NO 198
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 198
aagaccuacu ucccg                                                    15

<210> SEQ ID NO 199
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 199
agaccuacuu cccgc                                                    15

<210> SEQ ID NO 200
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 200
gaccuacuuc ccgca                                                    15

<210> SEQ ID NO 201
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 201
accuacuucc cgcac                                                    15

<210> SEQ ID NO 202
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 202
ccuacuuccc gcacu                                                    15

<210> SEQ ID NO 203
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 203
cuacuucccg cacuu                                              15

<210> SEQ ID NO 204
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 204
uacuucccgc acuuc                                              15

<210> SEQ ID NO 205
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 205
acuucccgca cuucg                                              15

<210> SEQ ID NO 206
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 206
cuucccgcac uucga                                              15

<210> SEQ ID NO 207
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 207
uucccgcacu ucgac                                              15

<210> SEQ ID NO 208
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 208
ucccgcacuu cgacc                                              15

<210> SEQ ID NO 209
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 209
cccgcacuuc gaccu                                              15

```
<210> SEQ ID NO 210
<211> LENGTH: 16
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 210
ccgcacuucg accuga                                                    16

<210> SEQ ID NO 211
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 211
cgcacuucga ccuga                                                     15

<210> SEQ ID NO 212
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 212
gcacuucgac cugag                                                     15

<210> SEQ ID NO 213
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 213
cacuucgacc ugagc                                                     15

<210> SEQ ID NO 214
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 214
acuucgaccu gagcc                                                     15

<210> SEQ ID NO 215
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 215
cuucgaccug agcca                                                     15
```

```
<210> SEQ ID NO 216
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 216
uucgaccuga gccac                                                      15

<210> SEQ ID NO 217
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 217
ucgaccugag ccacg                                                      15

<210> SEQ ID NO 218
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 218
cgaccugagc cacgg                                                      15

<210> SEQ ID NO 219
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 219
gaccugagcc acggc                                                      15

<210> SEQ ID NO 220
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 220
accugagcca cggcu                                                      15

<210> SEQ ID NO 221
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 221
ccugagccac ggcuc                                                      15
```

```
<210> SEQ ID NO 222
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 222
cugagccacg gcucu                                                    15

<210> SEQ ID NO 223
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 223
ugagccacgg cucug                                                    15

<210> SEQ ID NO 224
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 224
gagccacggc ucugc                                                    15

<210> SEQ ID NO 225
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 225
agccacggcu cugcc                                                    15

<210> SEQ ID NO 226
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 226
gccacggcuc ugccc                                                    15

<210> SEQ ID NO 227
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 227
ccacggcucu gccca                                                    15

<210> SEQ ID NO 228
```

```
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 228
cacggcucug cccag                                                      15

<210> SEQ ID NO 229
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 229
acggcucugc ccagg                                                      15

<210> SEQ ID NO 230
<211> LENGTH: 16
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 230
cggcucugcc cagguu                                                     16

<210> SEQ ID NO 231
<211> LENGTH: 16
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 231
ggcucugccc agguua                                                     16

<210> SEQ ID NO 232
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 232
gcucugccca gguua                                                      15

<210> SEQ ID NO 233
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 233
cucugcccag guuaa                                                      15

<210> SEQ ID NO 234
<211> LENGTH: 15
```

```
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 234
ucugcccagg uuaag                                                          15

<210> SEQ ID NO 235
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 235
cugcccaggu uaagg                                                          15

<210> SEQ ID NO 236
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 236
ugcccagguu aaggg                                                          15

<210> SEQ ID NO 237
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 237
gcccagguua agggc                                                          15

<210> SEQ ID NO 238
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 238
cccagguuaa gggcc                                                          15

<210> SEQ ID NO 239
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 239
ccagguuaag ggcca                                                          15

<210> SEQ ID NO 240
<211> LENGTH: 15
<212> TYPE: RNA
```

```
<213> ORGANISM: artificial sequence
<220> FEATURE:
<223> OTHER INFORMATION: 15mer sense oligonucelotides which represent
      targets on HBA1 mRNA

<400> SEQUENCE: 240
cagguuaagg gccac                                                          15

<210> SEQ ID NO 241
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 241
agguuaaggg ccacg                                                          15

<210> SEQ ID NO 242
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 242
gguuaagggc cacgg                                                          15

<210> SEQ ID NO 243
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 243
guuaagggcc acggc                                                          15

<210> SEQ ID NO 244
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 244
uuaagggcca cggca                                                          15

<210> SEQ ID NO 245
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 245
uaagggccac ggcaa                                                          15

<210> SEQ ID NO 246
<211> LENGTH: 15
<212> TYPE: RNA
<213> ORGANISM: artificial sequence
```

```
<220> FEATURE:
<223> OTHER INFORMATION: 15mer sense oligonucelotides which represent
      targets on HBA1 mRNA

<400> SEQUENCE: 246
aagggccacg gcaag                                                          15

<210> SEQ ID NO 247
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA1 mRNA

<400> SEQUENCE: 247
taagggccac ggcaa                                                          15

<210> SEQ ID NO 248
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 248
agggccacgg caaga                                                          15

<210> SEQ ID NO 249
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 249
gggccacggc aagaa                                                          15

<210> SEQ ID NO 250
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 250
ggccacggca agaag                                                          15

<210> SEQ ID NO 251
<211> LENGTH: 17
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 251
gccacggcaa gaaggug                                                        17

<210> SEQ ID NO 252
<211> LENGTH: 15
<212> TYPE: RNA
<213> ORGANISM: artificial sequence
<220> FEATURE:
```

```
<223> OTHER INFORMATION: 15mer sense oligonucelotides which represent
      targets on HBA1 mRNA

<400> SEQUENCE: 252
ccacggcaag aaggu                                                        15

<210> SEQ ID NO 253
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 253
cacggcaaga aggug                                                        15

<210> SEQ ID NO 254
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 254
acggcaagaa ggugg                                                        15

<210> SEQ ID NO 255
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 255
cggcaagaag guggc                                                        15

<210> SEQ ID NO 256
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 256
ggcaagaagg uggcc                                                        15

<210> SEQ ID NO 257
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 257
gcaagaaggu ggccg                                                        15

<210> SEQ ID NO 258
<211> LENGTH: 15
<212> TYPE: RNA
<213> ORGANISM: artificial sequence
<220> FEATURE:
<223> OTHER INFORMATION: 15mer sense oligonucelotides which represent
``` targets on HBA1 mRNA

<400> SEQUENCE: 258
caagaaggug gccga                                                          15

<210> SEQ ID NO 259
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 259
aagaaggugg ccgac                                                          15

<210> SEQ ID NO 260
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 260
agaagguggc cgacg                                                          15

<210> SEQ ID NO 261
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 261
gaagguggcc gacgc                                                          15

<210> SEQ ID NO 262
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 262
aagguggccg acgcg                                                          15

<210> SEQ ID NO 263
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 263
agguggccga cgcgc                                                          15

<210> SEQ ID NO 264
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

```
<400> SEQUENCE: 264
gguggccgac gcgcu                                                         15

<210> SEQ ID NO 265
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 265
guggccgacg cgcug                                                         15

<210> SEQ ID NO 266
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 266
uggccgacgc gcuga                                                         15

<210> SEQ ID NO 267
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 267
ggccgacgcg cugac                                                         15

<210> SEQ ID NO 268
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 268
gccgacgcgc ugacc                                                         15

<210> SEQ ID NO 269
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 269
ccgacgcgcu gacca                                                         15

<210> SEQ ID NO 270
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA
```

<400> SEQUENCE: 270
cgacgcgcug accaa                                                     15

<210> SEQ ID NO 271
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 271
gacgcgcuga ccaac                                                     15

<210> SEQ ID NO 272
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 272
acgcgcugac caacg                                                     15

<210> SEQ ID NO 273
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 273
cgcgcugacc aacgc                                                     15

<210> SEQ ID NO 274
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 274
gcgcugacca acgcc                                                     15

<210> SEQ ID NO 275
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 275
cgcugaccaa cgccg                                                     15

<210> SEQ ID NO 276
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 276

```
gcugaccaac gccgu                                                   15

<210> SEQ ID NO 277
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 277
cugaccaacg ccgug                                                   15

<210> SEQ ID NO 278
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 278
ugaccaacgc cgugg                                                   15

<210> SEQ ID NO 279
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 279
gaccaacgcc guggc                                                   15

<210> SEQ ID NO 280
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 280
accaacgccg uggcg                                                   15

<210> SEQ ID NO 281
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 281
ccaacgccgu ggcgc                                                   15

<210> SEQ ID NO 282
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 282
```
caacgccgug gcgca                                                           15

<210> SEQ ID NO 283
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 283
aacgccgugg cgcac                                                           15

<210> SEQ ID NO 284
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 284
acgccguggc gcacg                                                           15

<210> SEQ ID NO 285
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 285
cgccguggcg cacgu                                                           15

<210> SEQ ID NO 286
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 286
gccguggcgc acgug                                                           15

<210> SEQ ID NO 287
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 287
ccguggcgca cgugg                                                           15

<210> SEQ ID NO 288
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 288
cguggcgcac gugga                                                           15

-continued

<210> SEQ ID NO 289
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 289
guggcgcacg uggac                                                    15

<210> SEQ ID NO 290
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 290
uggcgcacgu ggacg                                                    15

<210> SEQ ID NO 291
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 291
ggcgcacgug gacga                                                    15

<210> SEQ ID NO 292
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 292
gcgcacgugg acgac                                                    15

<210> SEQ ID NO 293
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 293
cgcacgugga cgaca                                                    15

<210> SEQ ID NO 294
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 294
gcacguggac gacau                                                    15

<210> SEQ ID NO 295
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 295
cacguggacg acaug                                                    15

<210> SEQ ID NO 296
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 296
acguggacga caugc                                                    15

<210> SEQ ID NO 297
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 297
cguggacgac augcc                                                    15

<210> SEQ ID NO 298
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 298
guggacgaca ugccc                                                    15

<210> SEQ ID NO 299
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 299
uggacgacau gccca                                                    15

<210> SEQ ID NO 300
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 300
ggacgacaug cccaa                                                    15

```
<210> SEQ ID NO 301
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 301
gacgacaugc ccaac                                                         15

<210> SEQ ID NO 302
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 302
acgacaugcc caacg                                                         15

<210> SEQ ID NO 303
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 303
cgacaugccc aacgc                                                         15

<210> SEQ ID NO 304
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 304
gacaugccca acgcg                                                         15

<210> SEQ ID NO 305
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 305
acaugcccaa cgcgc                                                         15

<210> SEQ ID NO 306
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 306
caugcccaac gcgcu                                                         15

<210> SEQ ID NO 307
```

```
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 307
augcccaacg cgcug                                                    15

<210> SEQ ID NO 308
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 308
ugcccaacgc gcugu                                                    15

<210> SEQ ID NO 309
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 309
gcccaacgcg cuguc                                                    15

<210> SEQ ID NO 310
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 310
cccaacgcgc ugucc                                                    15

<210> SEQ ID NO 311
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 311
ccaacgcgcu guccg                                                    15

<210> SEQ ID NO 312
<211> LENGTH: 16
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 312
caacgcgcug uccgcc                                                   16

<210> SEQ ID NO 313
<211> LENGTH: 15
```

```
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 313
aacgcgcugu ccgcc                                                       15

<210> SEQ ID NO 314
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 314
acgcgcuguc cgccc                                                       15

<210> SEQ ID NO 315
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 315
cgcgcugucc gcccu                                                       15

<210> SEQ ID NO 316
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 316
gcgcuguccg cccug                                                       15

<210> SEQ ID NO 317
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 317
cgcuguccgc ccuga                                                       15

<210> SEQ ID NO 318
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 318
gcuguccgcc cugag                                                       15

<210> SEQ ID NO 319
<211> LENGTH: 15
<212> TYPE: RNA
```

```
<213> ORGANISM: artificial sequence
<220> FEATURE:
<223> OTHER INFORMATION: 15mer sense oligonucelotides which represent
      targets on HBA1 mRNA

<400> SEQUENCE: 319 cguccgccc ugagc                                                         15

<210> SEQ ID NO 320
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 320
uguccgcccu gagcg                                                        15

<210> SEQ ID NO 321
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 321
guccgcccug agcga                                                        15

<210> SEQ ID NO 322
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 322
uccgcccuga gcgac                                                        15

<210> SEQ ID NO 323
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 323
ccgcccugag cgacc                                                        15

<210> SEQ ID NO 324
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 324
cgcccugagc gaccu                                                        15

<210> SEQ ID NO 325
<211> LENGTH: 15
<212> TYPE: RNA
<213> ORGANISM: artificial sequence
```

```
<220> FEATURE:
<223> OTHER INFORMATION: 15mer sense oligonucelotides which represent
      targets on HBA1 mRNA

<400> SEQUENCE: 325
gcccugagcg accug                                                      15

<210> SEQ ID NO 326
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 326
cccugagcga ccugc                                                      15

<210> SEQ ID NO 327
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 327
ccugagcgac cugca                                                      15

<210> SEQ ID NO 328
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 328
cugagcgacc ugcac                                                      15

<210> SEQ ID NO 329
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 329
ugagcgaccu gcacg                                                      15

<210> SEQ ID NO 330
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 330
gagcgaccug cacgc                                                      15

<210> SEQ ID NO 331
<211> LENGTH: 15
<212> TYPE: RNA
<213> ORGANISM: artificial sequence
<220> FEATURE:
```

```
<223> OTHER INFORMATION: 15mer sense oligonucelotides which represent
      targets on HBA1 mRNA

<400> SEQUENCE: 331
agcgaccugc acgcg                                                    15

<210> SEQ ID NO 332
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 332
gcgaccugca cgcgc                                                    15

<210> SEQ ID NO 333
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 333
cgaccugcac gcgca                                                    15

<210> SEQ ID NO 334
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 334
gaccugcacg cgcac                                                    15

<210> SEQ ID NO 335
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 335
accugcacgc gcaca                                                    15

<210> SEQ ID NO 336
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 336
ccugcacgcg cacaa                                                    15

<210> SEQ ID NO 337
<211> LENGTH: 15
<212> TYPE: RNA
<213> ORGANISM: artificial sequence
<220> FEATURE:
<223> OTHER INFORMATION: 15mer sense oligonucelotides which represent
``` targets on HBA1 mRNA

<400> SEQUENCE: 337
cugcacgcgc acaag                                                      15

<210> SEQ ID NO 338
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 338
ugcacgcgca caagc                                                      15

<210> SEQ ID NO 339
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 339
gcacgcgcac aagcu                                                      15

<210> SEQ ID NO 340
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 340
cacgcgcaca agcuu                                                      15

<210> SEQ ID NO 341
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 341
acgcgcacaa gcuuc                                                      15

<210> SEQ ID NO 342
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 342
cgcgcacaag cuucg                                                      15

<210> SEQ ID NO 343
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA1 mRNA

```
<400> SEQUENCE: 343
cgcgcacaag cttcg                                                      15

<210> SEQ ID NO 344
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 344
gcgcacaagc uucgg                                                      15

<210> SEQ ID NO 345
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 345
cgcacaagcu ucggg                                                      15

<210> SEQ ID NO 346
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 346
gcacaagcuu cgggu                                                      15

<210> SEQ ID NO 347
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 347
cacaagcuuc gggug                                                      15

<210> SEQ ID NO 348
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 348
acaagcuucg ggugg                                                      15

<210> SEQ ID NO 349
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA
```

```
<400> SEQUENCE: 349
caagcuucgg gugga                                                        15

<210> SEQ ID NO 350
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 350
aagcuucggg uggac                                                        15

<210> SEQ ID NO 351
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 351
agcuucgggu ggacc                                                        15

<210> SEQ ID NO 352
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 352
gcuucggguc gaccc                                                        15

<210> SEQ ID NO 353
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 353
cuucgggugg acccg                                                        15

<210> SEQ ID NO 354
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 354
uucgggugga cccgg                                                        15

<210> SEQ ID NO 355
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 355
```
ucggguggac ccggu                                                15

<210> SEQ ID NO 356
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 356
cggguggacc cgguc                                                15

<210> SEQ ID NO 357
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 357
ggguggaccc gguca                                                15

<210> SEQ ID NO 358
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 358
gguggacccg gucaa                                                15

<210> SEQ ID NO 359
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 359
guggacccgg ucaac                                                15

<210> SEQ ID NO 360
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 360
uggacccggu caacu                                                15

<210> SEQ ID NO 361
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 361

```
ggacccgguc aacuu                                                          15

<210> SEQ ID NO 362
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 362
gacccgguca acuuc                                                          15

<210> SEQ ID NO 363
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 363
acccggucaa cuuca                                                          15

<210> SEQ ID NO 364
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 364
cccggucaac uucaa                                                          15

<210> SEQ ID NO 365
<211> LENGTH: 21
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 365
ccggucaacu ucaagcuccu a                                                   21

<210> SEQ ID NO 366
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 366
cggucaacuu caagc                                                          15

<210> SEQ ID NO 367
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 367
ggucaacuuc aagcu                                                          15
```

<210> SEQ ID NO 368
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 368
gucaacuuca agcuc                                                    15

<210> SEQ ID NO 369
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 369
ucaacuucaa gcucc                                                    15

<210> SEQ ID NO 370
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 370
caacuucaag cuccu                                                    15

<210> SEQ ID NO 371
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 371
aacuucaagc uccua                                                    15

<210> SEQ ID NO 372
<211> LENGTH: 17
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 372
acuucaagcu ccuaagc                                                  17

<210> SEQ ID NO 373
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 373
cuucaagcuc cuaag                                                    15

<210> SEQ ID NO 374
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 374
uucaagcucc uaagc                                                     15

<210> SEQ ID NO 375
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 375
ucaagcuccu aagcc                                                     15

<210> SEQ ID NO 376
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 376
caagcuccua agcca                                                     15

<210> SEQ ID NO 377
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 377
aagcuccuaa gccac                                                     15

<210> SEQ ID NO 378
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 378
agcuccuaag ccacu                                                     15

<210> SEQ ID NO 379
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 379
gcuccuaagc cacug                                                     15

-continued

```
<210> SEQ ID NO 380
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 380
cuccuaagcc acugc                                                    15

<210> SEQ ID NO 381
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 381
uccuaagcca cugcc                                                    15

<210> SEQ ID NO 382
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 382
ccuaagccac ugccu                                                    15

<210> SEQ ID NO 383
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 383
cuaagccacu gccug                                                    15

<210> SEQ ID NO 384
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 384
uaagccacug ccugc                                                    15

<210> SEQ ID NO 385
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 385
aagccacugc cugcu                                                    15

<210> SEQ ID NO 386
```

```
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 386
agccacugcc ugcug                                                    15

<210> SEQ ID NO 387
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 387
gccacugccu gcugg                                                    15

<210> SEQ ID NO 388
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 388
ccacugccug cuggu                                                    15

<210> SEQ ID NO 389
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 389
cacugccugc uggug                                                    15

<210> SEQ ID NO 390
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 390
acugccugcu gguga                                                    15

<210> SEQ ID NO 391
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 391
cugccugcug gugac                                                    15

<210> SEQ ID NO 392
<211> LENGTH: 15
```

<212> TYPE: RNA
<213> ORGANISM: artificial sequence
<220> FEATURE:
<223> OTHER INFORMATION: 15mer sense oligonucelotides which represent targets on HBA1 mRNA
<400> SEQUENCE: 392
ugccugcugg ugacc 15

<210> SEQ ID NO 393
<211> LENGTH: 15
<212> TYPE: RNA
<213> ORGANISM: artificial sequence
<220> FEATURE:
<223> OTHER INFORMATION: 15mer sense oligonucelotides which represent targets on HBA1 mRNA
<400> SEQUENCE: 393
gccugcuggu gaccc 15

<210> SEQ ID NO 394
<211> LENGTH: 15
<212> TYPE: RNA
<213> ORGANISM: artificial sequence
<220> FEATURE:
<223> OTHER INFORMATION: 15mer sense oligonucelotides which represent targets on HBA1 mRNA
<400> SEQUENCE: 394
ccugcuggug acccu 15

<210> SEQ ID NO 395
<211> LENGTH: 15
<212> TYPE: RNA
<213> ORGANISM: artificial sequence
<220> FEATURE:
<223> OTHER INFORMATION: 15mer sense oligonucelotides which represent targets on HBA1 mRNA
<400> SEQUENCE: 395
cugcugguga cccug 15

<210> SEQ ID NO 396
<211> LENGTH: 15
<212> TYPE: RNA
<213> ORGANISM: artificial sequence
<220> FEATURE:
<223> OTHER INFORMATION: 15mer sense oligonucelotides which represent targets on HBA1 mRNA
<400> SEQUENCE: 396
ugcuggugac ccugg 15

<210> SEQ ID NO 397
<211> LENGTH: 15
<212> TYPE: RNA
<213> ORGANISM: artificial sequence
<220> FEATURE:
<223> OTHER INFORMATION: 15mer sense oligonucelotides which represent targets on HBA1 mRNA
<400> SEQUENCE: 397
gcuggugacc cuggc 15

<210> SEQ ID NO 398
<211> LENGTH: 15
<212> TYPE: RNA

-continued

<213> ORGANISM: artificial sequence
<220> FEATURE:
<223> OTHER INFORMATION: 15mer sense oligonucelotides which represent
      targets on HBA1 mRNA

<400> SEQUENCE: 398
cuggugaccc uggcc                                                          15

<210> SEQ ID NO 399
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 399
uggugacccu ggccg                                                          15

<210> SEQ ID NO 400
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 400
ggugacccug gccgc                                                          15

<210> SEQ ID NO 401
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 401
gugacccugg ccgcc                                                          15

<210> SEQ ID NO 402
<211> LENGTH: 17
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 402
ugacccuggc cgcccac                                                        17

<210> SEQ ID NO 403
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 403
gacccuggcc gccca                                                          15

<210> SEQ ID NO 404
<211> LENGTH: 15
<212> TYPE: RNA
<213> ORGANISM: artificial sequence

```
<220> FEATURE:
<223> OTHER INFORMATION: 15mer sense oligonucelotides which represent
      targets on HBA1 mRNA

<400> SEQUENCE: 404
acccuggccg cccac                                                       15

<210> SEQ ID NO 405
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 405
cccuggccgc ccacc                                                       15

<210> SEQ ID NO 406
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 406
ccuggccgcc caccu                                                       15

<210> SEQ ID NO 407
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 407
cuggccgccc accuc                                                       15

<210> SEQ ID NO 408
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 408
uggccgccca ccucc                                                       15

<210> SEQ ID NO 409
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 409
ggccgcccac cuccc                                                       15

<210> SEQ ID NO 410
<211> LENGTH: 15
<212> TYPE: RNA
<213> ORGANISM: artificial sequence
<220> FEATURE:
```

```
<223> OTHER INFORMATION: 15mer sense oligonucelotides which represent
      targets on HBA1 mRNA

<400> SEQUENCE: 410
gccgcccacc ucccc                                                     15

<210> SEQ ID NO 411
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 411
ccgcccaccu ccccg                                                     15

<210> SEQ ID NO 412
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 412
cgcccaccuc cccgc                                                     15

<210> SEQ ID NO 413
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 413
gcccaccucc ccgcc                                                     15

<210> SEQ ID NO 414
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 414
cccaccuccc cgccg                                                     15

<210> SEQ ID NO 415
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 415
ccaccucccc gccga                                                     15

<210> SEQ ID NO 416
<211> LENGTH: 15
<212> TYPE: RNA
<213> ORGANISM: artificial sequence
<220> FEATURE:
<223> OTHER INFORMATION: 15mer sense oligonucelotides which represent
``` targets on HBA1 mRNA

<400> SEQUENCE: 416
caccuccccg ccgag                                                    15

<210> SEQ ID NO 417
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 417
accuccccgc cgagu                                                    15

<210> SEQ ID NO 418
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 418
ccuccccgcc gaguu                                                    15

<210> SEQ ID NO 419
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 419
cuccccgccg aguuc                                                    15

<210> SEQ ID NO 420
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 420
uccccgccga guuca                                                    15

<210> SEQ ID NO 421
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 421
ccccgccgag uucac                                                    15

<210> SEQ ID NO 422
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

```
<400> SEQUENCE: 422
cccgccgagu ucacc                                                        15

<210> SEQ ID NO 423
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 423
ccgccgaguu caccc                                                        15

<210> SEQ ID NO 424
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 424
cgccgaguuc acccc                                                        15

<210> SEQ ID NO 425
<211> LENGTH: 11
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 425
gccgaguuca c                                                            11

<210> SEQ ID NO 426
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 426
ccgaguucac cccug                                                        15

<210> SEQ ID NO 427
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 427
cgaguucacc ccugc                                                        15

<210> SEQ ID NO 428
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA
```

```
<400> SEQUENCE: 428
gaguucaccc cugcg                                                        15

<210> SEQ ID NO 429
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 429 aguucaccccc ugcgg                                                       15

<210> SEQ ID NO 430
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 430
guucaccccu gcggu                                                        15

<210> SEQ ID NO 431
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 431
uucaccccug cggug                                                        15

<210> SEQ ID NO 432
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 432
ucaccccugc ggugc                                                        15

<210> SEQ ID NO 433
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 433
caccccugcg gugca                                                        15

<210> SEQ ID NO 434
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 434
```

```
accccugcgg ugcac                                                    15

<210> SEQ ID NO 435
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 435
ccccugcggu gcacg                                                    15

<210> SEQ ID NO 436
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 436
cccugcggug cacgc                                                    15

<210> SEQ ID NO 437
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 437
ccugcggugc acgcc                                                    15

<210> SEQ ID NO 438
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 438
cugcggugca cgccu                                                    15

<210> SEQ ID NO 439
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 439
ugcggugcac gccuc                                                    15

<210> SEQ ID NO 440
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 440
```
gcggugcacg ccucc   15

<210> SEQ ID NO 441
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 441
cggugcacgc cuccc   15

<210> SEQ ID NO 442
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 442
ggugcacgcc ucccu   15

<210> SEQ ID NO 443
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 443
gugcacgccu cccug   15

<210> SEQ ID NO 444
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 444
ugcacgccuc ccugg   15

<210> SEQ ID NO 445
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 445
gcacgccucc cugga   15

<210> SEQ ID NO 446
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 446
cacgccuccc uggac   15

<210> SEQ ID NO 447
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 447
acgccucccu ggaca                                                    15

<210> SEQ ID NO 448
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 448
cgccucccug gacaa                                                    15

<210> SEQ ID NO 449
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 449
gccucccugg acaag                                                    15

<210> SEQ ID NO 450
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 450
ccucccugga caagu                                                    15

<210> SEQ ID NO 451
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 451
cucccuggac aaguu                                                    15

<210> SEQ ID NO 452
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 452
ucccuggaca aguuc                                                    15

<210> SEQ ID NO 453
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 453
cccuggacaa guucc                                                        15

<210> SEQ ID NO 454
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 454
ccuggacaag uuccu                                                        15

<210> SEQ ID NO 455
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 455
cuggacaagu uccug                                                        15

<210> SEQ ID NO 456
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 456
uggacaaguu ccugg                                                        15

<210> SEQ ID NO 457
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 457
ggacaaguuc cuggc                                                        15

<210> SEQ ID NO 458
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 458
gacaaguucc uggcu                                                        15

<210> SEQ ID NO 459
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 459
acaaguuccu ggcuu                                                        15

<210> SEQ ID NO 460
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 460
caaguuccug gcuuc                                                        15

<210> SEQ ID NO 461
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 461
aguuccuggc uucug                                                        15

<210> SEQ ID NO 462
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 462
guuccuggcu ucugu                                                        15

<210> SEQ ID NO 463
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 463
uuccuggcuu cugug                                                        15

<210> SEQ ID NO 464
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 464
uccuggcuuc uguga                                                        15

<210> SEQ ID NO 465

-continued

```
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 465
ccuggcuucu gugag                                                15

<210> SEQ ID NO 466
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 466
uggcuucugu gagca                                                15

<210> SEQ ID NO 467
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 467
cuucugugag caccg                                                15

<210> SEQ ID NO 468
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 468
ucugugagca ccgug                                                15

<210> SEQ ID NO 469
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 469
cugugagcac cgugc                                                15

<210> SEQ ID NO 470
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 470
gugagcaccg ugcug                                                15

<210> SEQ ID NO 471
<211> LENGTH: 15
```

```
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 471
ugagcaccgu gcuga                                                        15

<210> SEQ ID NO 472
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 472
agcaccgugc ugacc                                                        15

<210> SEQ ID NO 473
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 473
gcaccgugcu gaccu                                                        15

<210> SEQ ID NO 474
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 474
caccgugcug accuc                                                        15

<210> SEQ ID NO 475
<211> LENGTH: 17
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 475
accgugcuga ccuccaa                                                      17

<210> SEQ ID NO 476
<211> LENGTH: 16
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 476
ccgugcugac cuccaa                                                       16

<210> SEQ ID NO 477
<211> LENGTH: 15
<212> TYPE: RNA
```

```
<213> ORGANISM: artificial sequence
<220> FEATURE:
<223> OTHER INFORMATION: 15mer sense oligonucelotides which represent
      targets on HBA1 mRNA

<400> SEQUENCE: 477
cgugcugacc uccaa                                                          15

<210> SEQ ID NO 478
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 478
gugcugaccu ccaaa                                                          15

<210> SEQ ID NO 479
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 479
caaauaccgu uaagc                                                          15

<210> SEQ ID NO 480
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 480
aaauaccguu aagcu                                                          15

<210> SEQ ID NO 481
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 481
aauaccguua agcug                                                          15

<210> SEQ ID NO 482
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 482
uaccguuaag cugga                                                          15

<210> SEQ ID NO 483
<211> LENGTH: 15
<212> TYPE: RNA
<213> ORGANISM: artificial sequence
```

```
<220> FEATURE:
<223> OTHER INFORMATION: 15mer sense oligonucelotides which represent
      targets on HBA1 mRNA

<400> SEQUENCE: 483
uaagcuggag ccucg                                              15

<210> SEQ ID NO 484
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 484
cuggagccuc gguag                                              15

<210> SEQ ID NO 485
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 485
uggagccucg guagc                                              15

<210> SEQ ID NO 486
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 486
gagccucggu agccg                                              15

<210> SEQ ID NO 487
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 487
agccucggua gccgu                                              15

<210> SEQ ID NO 488
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 488
gccucgguag ccguu                                              15

<210> SEQ ID NO 489
<211> LENGTH: 15
<212> TYPE: RNA
<213> ORGANISM: artificial sequence
<220> FEATURE:
```

```
<223> OTHER INFORMATION: 15mer sense oligonucelotides which represent
      targets on HBA1 mRNA

<400> SEQUENCE: 489
ccucgguagc cguuc                                                          15

<210> SEQ ID NO 490
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 490
cucgguagcc guucc                                                          15

<210> SEQ ID NO 491
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 491
ucgguagccg uuccu                                                          15

<210> SEQ ID NO 492
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 492
cgguagccgu uccuc                                                          15

<210> SEQ ID NO 493
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 493
gguagccguu ccucc                                                          15

<210> SEQ ID NO 494
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 494
guagccguuc cuccu                                                          15

<210> SEQ ID NO 495
<211> LENGTH: 15
<212> TYPE: RNA
<213> ORGANISM: artificial sequence
<220> FEATURE:
<223> OTHER INFORMATION: 15mer sense oligonucelotides which represent
``` targets on HBA1 mRNA

<400> SEQUENCE: 495
uagccguucc uccug                                                15

<210> SEQ ID NO 496
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 496
agccguuccu ccugc                                                15

<210> SEQ ID NO 497
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 497
gccguuccuc cugcc                                                15

<210> SEQ ID NO 498
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 498
ccguuccucc ugccg                                                15

<210> SEQ ID NO 499
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 499
cguuccuccu gccgc                                                15

<210> SEQ ID NO 500
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 500
guuccuccug ccgcu                                                15

<210> SEQ ID NO 501
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA -continued

<400> SEQUENCE: 501
uuccuccugc cgcug         15

<210> SEQ ID NO 502
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 502
uccuccugcc gcugg         15

<210> SEQ ID NO 503
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 503
ccuccugccg cuggg         15

<210> SEQ ID NO 504
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 504
cuccugccgc ugggc         15

<210> SEQ ID NO 505
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 505
uccugccgcu gggcc         15

<210> SEQ ID NO 506
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 506
ccugccgcug ggccu         15

<210> SEQ ID NO 507
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

```
<400> SEQUENCE: 507
cugccgcugg gccuc                                                    15

<210> SEQ ID NO 508
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 508
ugccgcuggg ccucc                                                    15

<210> SEQ ID NO 509
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 509
gccgcugggc cuccc                                                    15

<210> SEQ ID NO 510
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 510
ccgcugggcc uccca                                                    15

<210> SEQ ID NO 511
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 511
cgcugggccu cccaa                                                    15

<210> SEQ ID NO 512
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 512
gcugggccuc ccaac                                                    15

<210> SEQ ID NO 513
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 513
```
ugggccuccc aacgg 15

<210> SEQ ID NO 514
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 514
gggccuccca acggg 15

<210> SEQ ID NO 515
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 515 ggcucccaa cgggc 15

<210> SEQ ID NO 516
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 516
gccucccaac gggcc 15

<210> SEQ ID NO 517
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 517
ccucccaacg ggccc 15

<210> SEQ ID NO 518
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 518
cucccaacgg gcccu 15

<210> SEQ ID NO 519
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 519
ucccaacggg cccuc                                                      15

<210> SEQ ID NO 520
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 520
cccaacgggc ccucc                                                      15

<210> SEQ ID NO 521
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 521
ccaacgggcc cuccu                                                      15

<210> SEQ ID NO 522
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 522
caacgggccc uccuc                                                      15

<210> SEQ ID NO 523
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 523
aacgggcccu ccucc                                                      15

<210> SEQ ID NO 524
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 524
acgggcccuc cuccc                                                      15

<210> SEQ ID NO 525
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 525
cgggcccucc uccccc                                                     15

```
<210> SEQ ID NO 526
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 526
gggcccuccu ccccu                                                    15

<210> SEQ ID NO 527
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 527
ggcccuccuc ccuc                                                     15

<210> SEQ ID NO 528
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 528
gcccuccucc ccucc                                                    15

<210> SEQ ID NO 529
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 529
cccuccuccc cuccu                                                    15

<210> SEQ ID NO 530
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 530
ccuccucccc uccuu                                                    15

<210> SEQ ID NO 531
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 531
cuccuccccu ccuug                                                    15
```

```
<210> SEQ ID NO 532
<211> LENGTH: 17
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 532
ccuccccucc uugcacc                                                       17

<210> SEQ ID NO 533
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 533
cuccccuccu ugcac                                                         15

<210> SEQ ID NO 534
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 534
uccccuccuu gcacc                                                         15

<210> SEQ ID NO 535
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 535
ccccuccuug caccg                                                         15

<210> SEQ ID NO 536
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 536
cccuccuugc accgg                                                         15

<210> SEQ ID NO 537
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 537
ccuccuugca ccggc                                                         15
```

```
<210> SEQ ID NO 538
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 538
cuccuugcac cggcc                                                          15

<210> SEQ ID NO 539
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 539
uccuugcacc ggccc                                                          15

<210> SEQ ID NO 540
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 540
ccuugcaccg gcccu                                                          15

<210> SEQ ID NO 541
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 541
uugcaccggc ccuuc                                                          15

<210> SEQ ID NO 542
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 542
ugcaccggcc cuucc                                                          15

<210> SEQ ID NO 543
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 543
gcaccggccc uuccu                                                          15

<210> SEQ ID NO 544
```

```
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 544
caccggcccu uccug                                                      15

<210> SEQ ID NO 545
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 545
accggcccuu ccugg                                                      15

<210> SEQ ID NO 546
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 546
ccggcccuuc cuggu                                                      15

<210> SEQ ID NO 547
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 547
cggcccuucc ugguc                                                      15

<210> SEQ ID NO 548
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 548
ggcccuuccu ggucu                                                      15

<210> SEQ ID NO 549
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 549
gcccuuccug gucuu                                                      15

<210> SEQ ID NO 550
<211> LENGTH: 15
```

```
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 550
cccuuccugg ucuuu                                                     15

<210> SEQ ID NO 551
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 551
ccuuccuggu cuuug                                                     15

<210> SEQ ID NO 552
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 552
cuuccugguc uuuga                                                     15

<210> SEQ ID NO 553
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 553
uuccuggucu uugaa                                                     15

<210> SEQ ID NO 554
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 554 uccggucuu ugaau                                                      15

<210> SEQ ID NO 555
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 555 ccggucuuu gaaua                                                      15

<210> SEQ ID NO 556
<211> LENGTH: 14
<212> TYPE: RNA
```

```
<213> ORGANISM: artificial sequence
<220> FEATURE:
<223> OTHER INFORMATION: 15mer sense oligonucelotides which represent
      targets on HBA1 mRNA

<400> SEQUENCE: 556
cuggucuuug aaua                                                          14

<210> SEQ ID NO 557
<211> LENGTH: 14
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 557
uggucuuuga auaa                                                          14

<210> SEQ ID NO 558
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 558
gucuuugaau aaagu                                                         15

<210> SEQ ID NO 559
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 559
ucuuugaaua aaguc                                                         15

<210> SEQ ID NO 560
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 560
cuuugaauaa agucu                                                         15

<210> SEQ ID NO 561
<211> LENGTH: 16
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 561
uuugaauaaa gucuga                                                        16

<210> SEQ ID NO 562
<211> LENGTH: 15
<212> TYPE: RNA
<213> ORGANISM: artificial sequence
```

```
<220> FEATURE:
<223> OTHER INFORMATION: 15mer sense oligonucelotides which represent
      targets on HBA1 mRNA

<400> SEQUENCE: 562
uugaauaaag ucuga                                                           15

<210> SEQ ID NO 563
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 563
ugaauaaagu cugag                                                           15

<210> SEQ ID NO 564
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 564
gaauaaaguc ugagu                                                           15

<210> SEQ ID NO 565
<211> LENGTH: 14
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 565
aauaaagucu gagu                                                            14

<210> SEQ ID NO 566
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 566
auaaagucug agugg                                                           15

<210> SEQ ID NO 567
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA1 mRNA

<400> SEQUENCE: 567
tcctgcaccc gtacc                                                           15

<210> SEQ ID NO 568
<211> LENGTH: 15
<212> TYPE: RNA
<213> ORGANISM: artificial sequence
<220> FEATURE:
```

```
<223> OTHER INFORMATION: 15mer sense oligonucelotides which represent
      targets on HBA1 mRNA

<400> SEQUENCE: 568
uaaagucuga guggg                                                          15

<210> SEQ ID NO 569
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 569
aaagucugag ugggc                                                          15

<210> SEQ ID NO 570
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 570
aagucugagu gggcg                                                          15

<210> SEQ ID NO 571
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 571
agucugagug ggcgg                                                          15

<210> SEQ ID NO 572
<211> LENGTH: 15
<212> TYPE: RNA
<213> ORGANISM: artificial sequence
<220> FEATURE:
<223> OTHER INFORMATION: 15mer sense oligonucelotides which represent
      targets on HBA1 mRNA

<400> SEQUENCE: 572
gucugagugg gcggc                                                          15

<210> SEQ ID NO 573
<211> LENGTH: 622
<212> TYPE: DNA
<213> ORGANISM: artificial sequence
<220> FEATURE:
<223> OTHER INFORMATION: Nucleotide sequence of hemoglobin alpha2 (HBA2)
      mRNA

<400> SEQUENCE: 573
cauaaacccu ggcgcgcucg cgggccggca cucuucuggu ccccacagac ucagagagaa          60
cccaccatgg ugctgcuccc ugccgacaag accaacguca aggccgccug ggguaagguc        120
ggcgcgcacg cuggcgagua uggugcggag gcccuggaga ggauguuccu guccuucccc        180
accaccaaga ccuacuuccc gcacuucgac cugagccacg gcucugccca gguuaagggc        240
cacggcaaga agguggccga cgcgcugacc aacgccgugg cgcacgugga cgacaugccc        300
```

```
aacgcgcugu ccgcccugag cgaccugcac gcgcacaagc uucggcugga cccggucaac    360
uucaagcucc uaagccacug ccugcuggug acccuggccg cccaccuccc cgccgaguuc    420
accccugcgg ugcacgccuc ccuggacaag uuccuggcuu cugugagcac cgugcugacc    480
uccaaauacc guuaagcugg agccucggua gccguuccuc cugcccgcug ggccucccaa    540
cgggcccucc uccccuccuu gcaccggccc uuccuggucu uugaauaaag ucugaguggg    600
cagcaaaaaa aaaaaaaaaa aa                                             622
```

<210> SEQ ID NO 574
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 574
cauaaacccu ggcgc                                                     15

<210> SEQ ID NO 575
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 575
auaaacccug gcgcg                                                     15

<210> SEQ ID NO 576
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 576
uaaacccugg cgcgc                                                     15

<210> SEQ ID NO 577
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 577
aaacccuggc gcgcu                                                     15

<210> SEQ ID NO 578
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 578
aacccuggcg cgcuc                                                     15

-continued

<210> SEQ ID NO 579
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 579
acccuggcgc gcucg                                                        15

<210> SEQ ID NO 580
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 580
cccuggcgcg cucgc                                                        15

<210> SEQ ID NO 581
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 581
ccuggcgcgc ucgcg                                                        15

<210> SEQ ID NO 582
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 582
cuggcgcgcu cgcgg                                                        15

<210> SEQ ID NO 583
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 583
uggcgcgcuc gcggg                                                        15

<210> SEQ ID NO 584
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 584
ggcgcgcucg cgggc                                                        15

<210> SEQ ID NO 585

```
<210> SEQ ID NO 585
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 585
gcgcgcucgc gggcc                                                       15

<210> SEQ ID NO 586
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 586
cgcgcucgcg ggccg                                                       15

<210> SEQ ID NO 587
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 587
gcgcucgcgg gccgg                                                       15

<210> SEQ ID NO 588
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 588
cgcucgcggg ccggc                                                       15

<210> SEQ ID NO 589
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 589
gcucgcgggc cggca                                                       15

<210> SEQ ID NO 590
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 590
cucgcgggcc ggcac                                                       15

<210> SEQ ID NO 591
<211> LENGTH: 15
```

```
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 591
ucgcgggccg gcacu                                                        15

<210> SEQ ID NO 592
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 592
cgcgggccgg cacuc                                                        15

<210> SEQ ID NO 593
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 593
gcgggccggc acucu                                                        15

<210> SEQ ID NO 594
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 594
cgggccggca cucuu                                                        15

<210> SEQ ID NO 595
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 595
gggccggcac ucuuc                                                        15

<210> SEQ ID NO 596
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 596
ggccggcacu cuucu                                                        15

<210> SEQ ID NO 597
<211> LENGTH: 15
<212> TYPE: DNA
```

```
<213> ORGANISM: artificial sequence
<220> FEATURE:
<223> OTHER INFORMATION: 15mer sense oligonucelotides which represent
      targets on HBA2 mRNA

<400> SEQUENCE: 597
gccggcacuc uucug                                                      15

<210> SEQ ID NO 598
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 598
ccggcacucu ucugg                                                      15

<210> SEQ ID NO 599
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 599
cggcacucuu cuggu                                                      15

<210> SEQ ID NO 600
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 600
ggcacucuuc ugguc                                                      15

<210> SEQ ID NO 601
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 601
gcacucuucu ggucc                                                      15

<210> SEQ ID NO 602
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 602
cacucuucug guccc                                                      15

<210> SEQ ID NO 603
<211> LENGTH: 15
<212> TYPE: DNA
<213> ORGANISM: artificial sequence
```

```
<220> FEATURE:
<223> OTHER INFORMATION: 15mer sense oligonucelotides which represent
      targets on HBA2 mRNA

<400> SEQUENCE: 603
acucuucugg ucccc                                              15

<210> SEQ ID NO 604
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 604
cucuucuggu cccca                                              15

<210> SEQ ID NO 605
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 605
ucuucugguc cccac                                              15

<210> SEQ ID NO 606
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 606
cuucuggucc ccaca                                              15

<210> SEQ ID NO 607
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 607
uucugguccc cacag                                              15

<210> SEQ ID NO 608
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 608
ucuggucccc acaga                                              15

<210> SEQ ID NO 609
<211> LENGTH: 15
<212> TYPE: DNA
<213> ORGANISM: artificial sequence
<220> FEATURE:
```

```
<223> OTHER INFORMATION: 15mer sense oligonucelotides which represent
      targets on HBA2 mRNA

<400> SEQUENCE: 609
cuggucccca cagac                                                          15

<210> SEQ ID NO 610
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 610
ugguccccac agacu                                                          15

<210> SEQ ID NO 611
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 611
gguccccaca gacuc                                                          15

<210> SEQ ID NO 612
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 612
guccccacag acuca                                                          15

<210> SEQ ID NO 613
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 613
uccccacaga cucag                                                          15

<210> SEQ ID NO 614
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 614
ccccacagac ucaga                                                          15

<210> SEQ ID NO 615
<211> LENGTH: 15
<212> TYPE: DNA
<213> ORGANISM: artificial sequence
<220> FEATURE:
<223> OTHER INFORMATION: 15mer sense oligonucelotides which represent
``` targets on HBA2 mRNA

<400> SEQUENCE: 615
cccacagacu cagag				15

<210> SEQ ID NO 616
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 616
ccacagacuc agaga				15

<210> SEQ ID NO 617
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 617
cacagacuca gagag				15

<210> SEQ ID NO 618
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 618
acagacucag agaga				15

<210> SEQ ID NO 619
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 619
cagacucaga gagaa				15

<210> SEQ ID NO 620
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 620
agacucagag agaac				15

<210> SEQ ID NO 621
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

```
<400> SEQUENCE: 621
gacucagaga gaacc                                                    15

<210> SEQ ID NO 622
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 622
acucagagag aaccc                                                    15

<210> SEQ ID NO 623
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 623
cucagagaga accca                                                    15

<210> SEQ ID NO 624
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 624
ucagagagaa cccac                                                    15

<210> SEQ ID NO 625
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 625
cagagagaac ccacc                                                    15

<210> SEQ ID NO 626
<211> LENGTH: 15
<212> TYPE: DNA
<213> ORGANISM: aruificial sequence
<220> FEATURE:
<223> OTHER INFORMATION: 15mer sense oligonucelotides which represent
      targets on HBA2 mRNA

<400> SEQUENCE: 626
agagagaacc cacca                                                    15

<210> SEQ ID NO 627
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA
```

```
<400> SEQUENCE: 627
gagagaaccc accau                                                    15

<210> SEQ ID NO 628
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 628
agagaaccca ccaug                                                    15

<210> SEQ ID NO 629
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 629
gagaacccac caugg                                                    15

<210> SEQ ID NO 630
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 630
agaacccacc auggu                                                    15

<210> SEQ ID NO 631
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 631
gaacccacca uggug                                                    15

<210> SEQ ID NO 632
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 632
aacccaccau ggugc                                                    15

<210> SEQ ID NO 633
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 633
```
acccaccaug gugcu                                                15

<210> SEQ ID NO 634
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 634
cccaccaugg ugcug                                                15

<210> SEQ ID NO 635
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 635
ccaccauggu gcugu                                                15

<210> SEQ ID NO 636
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 636
caccauggug cuguc                                                15

<210> SEQ ID NO 637
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 637
accauggugc ugucu                                                15

<210> SEQ ID NO 638
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 638
ccauggugcu gucuc                                                15

<210> SEQ ID NO 639
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 639
cauggugcug ucucc					15

<210> SEQ ID NO 640
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 640
auggugcugu cuccu					15

<210> SEQ ID NO 641
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 641
uggugcuguc uccug					15

<210> SEQ ID NO 642
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 642
ggugcugucu ccugc					15

<210> SEQ ID NO 643
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 643
gugcugucuc cugcc					15

<210> SEQ ID NO 644
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 644
ugcugucucc ugccg					15

<210> SEQ ID NO 645
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 645
gcugucuccu gccga					15

```
<210> SEQ ID NO 646
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 646
cugucuccug ccgac                                                    15

<210> SEQ ID NO 647
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 647 ugucccugc cgaca                                                     15

<210> SEQ ID NO 648
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 648
gucuccugcc gacaa                                                    15

<210> SEQ ID NO 649
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 649
ucuccugccg acaag                                                    15

<210> SEQ ID NO 650
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 650
cuccugccga caaga                                                    15

<210> SEQ ID NO 651
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 651
uccugccgac aagac                                                    15
```

<210> SEQ ID NO 652
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 652
ccugccgaca agacc                                                     15

<210> SEQ ID NO 653
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 653
cugccgacaa gacca                                                     15

<210> SEQ ID NO 654
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 654
ugccgacaag accaa                                                     15

<210> SEQ ID NO 655
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 655
gccgacaaga ccaac                                                     15

<210> SEQ ID NO 656
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 656
ccgacaagac caacg                                                     15

<210> SEQ ID NO 657
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 657
cgacaagacc aacgu                                                     15

```
<210> SEQ ID NO 658
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 658
gacaagacca acguc                                                      15

<210> SEQ ID NO 659
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 659
acaagaccaa cguca                                                      15

<210> SEQ ID NO 660
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 660
caagaccaac gucaa                                                      15

<210> SEQ ID NO 661
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 661
aagaccaacg ucaag                                                      15

<210> SEQ ID NO 662
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 662
agaccaacgu caagg                                                      15

<210> SEQ ID NO 663
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 663
gaccaacguc aaggc                                                      15

<210> SEQ ID NO 664
```

```
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 664
accaacguca aggcc                                                     15

<210> SEQ ID NO 665
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 665
ccaacgucaa ggccg                                                     15

<210> SEQ ID NO 666
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 666
caacgucaag gccgc                                                     15

<210> SEQ ID NO 667
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 667
aacgucaagg ccgcc                                                     15

<210> SEQ ID NO 668
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 668
acgucaaggc cgccu                                                     15

<210> SEQ ID NO 669
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 669
cgucaaggcc gccug                                                     15

<210> SEQ ID NO 670
<211> LENGTH: 15
```

```
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 670
gucaaggccg ccugg                                                        15

<210> SEQ ID NO 671
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 671
ucaaggccgc cuggg                                                        15

<210> SEQ ID NO 672
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 672
caaggccgcc ugggg                                                        15

<210> SEQ ID NO 673
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 673
aaggccgccu ggggu                                                        15

<210> SEQ ID NO 674
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 674
aggccgccug gggua                                                        15

<210> SEQ ID NO 675
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 675
ggccgccugg gguaa                                                        15

<210> SEQ ID NO 676
<211> LENGTH: 15
<212> TYPE: DNA
```

```
<213> ORGANISM: artificial sequence
<220> FEATURE:
<223> OTHER INFORMATION: 15mer sense oligonucelotides which represent
      targets on HBA2 mRNA

<400> SEQUENCE: 676
gccgccuggg guaag                                                          15

<210> SEQ ID NO 677
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 677
ccgccugggg uaagg                                                          15

<210> SEQ ID NO 678
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 678
cgccuggggu aaggu                                                          15

<210> SEQ ID NO 679
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 679
gccuggggua agguc                                                          15

<210> SEQ ID NO 680
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 680
ccugggguaa ggucg                                                          15

<210> SEQ ID NO 681
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 681
cugggguaag gucgg                                                          15

<210> SEQ ID NO 682
<211> LENGTH: 15
<212> TYPE: DNA
<213> ORGANISM: artificial sequence
```

```
<220> FEATURE:
<223> OTHER INFORMATION: 15mer sense oligonucelotides which represent
      targets on HBA2 mRNA

<400> SEQUENCE: 682 uggggulaagg ucggc                                                    15

<210> SEQ ID NO 683
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 683
gggguaaggu cggcg                                                     15

<210> SEQ ID NO 684
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 684
ggguaagguc ggcgc                                                     15

<210> SEQ ID NO 685
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 685
gguaaggucg gcgcg                                                     15

<210> SEQ ID NO 686
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 686
guaaggucgg cgcgc                                                     15

<210> SEQ ID NO 687
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 687
uaaggucggc gcgca                                                     15

<210> SEQ ID NO 688
<211> LENGTH: 15
<212> TYPE: DNA
<213> ORGANISM: artificial sequence
<220> FEATURE:
```

-continued

<223> OTHER INFORMATION: 15mer sense oligonucelotides which represent
      targets on HBA2 mRNA

<400> SEQUENCE: 688
aaggucggcg cgcac                                                        15

<210> SEQ ID NO 689
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 689
aggucggcgc gcacg                                                        15

<210> SEQ ID NO 690
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 690
ggucggcgcg cacgc                                                        15

<210> SEQ ID NO 691
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 691
gucggcgcgc acgcu                                                        15

<210> SEQ ID NO 692
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 692
ucggcgcgca cgcug                                                        15

<210> SEQ ID NO 693
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 693
cggcgcgcac gcugg                                                        15

<210> SEQ ID NO 694
<211> LENGTH: 15
<212> TYPE: DNA
<213> ORGANISM: artificial sequence
<220> FEATURE:
<223> OTHER INFORMATION: 15mer sense oligonucelotides which represent targets on HBA2 mRNA

<400> SEQUENCE: 694
ggcgcgcacg cuggc                                              15

<210> SEQ ID NO 695
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 695
gcgcgcacgc uggcg                                              15

<210> SEQ ID NO 696
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 696
cgcgcacgcu ggcga                                              15

<210> SEQ ID NO 697
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 697
gcgcacgcug gcgag                                              15

<210> SEQ ID NO 698
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 698
cgcacgcugg cgagu                                              15

<210> SEQ ID NO 699
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 699
gcacgcuggc gagua                                              15

<210> SEQ ID NO 700
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

```
<400> SEQUENCE: 700
cacgcuggcg aguau                                                    15

<210> SEQ ID NO 701
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 701
acgcuggcga guaug                                                    15

<210> SEQ ID NO 702
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 702
cgcuggcgag uaugg                                                    15

<210> SEQ ID NO 703
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 703
gcuggcgagu auggu                                                    15

<210> SEQ ID NO 704
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 704
cuggcgagua uggug                                                    15

<210> SEQ ID NO 705
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 705
uggcgaguau ggugc                                                    15

<210> SEQ ID NO 706
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA
```

<400> SEQUENCE: 706
ggcgaguaug gugcg                                          15

<210> SEQ ID NO 707
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 707
gcgaguaugg ugcgg                                          15

<210> SEQ ID NO 708
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 708
cgaguauggu gcgga                                          15

<210> SEQ ID NO 709
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 709
gaguauggug cggag                                          15

<210> SEQ ID NO 710
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 710
aguauggugc ggagg                                          15

<210> SEQ ID NO 711
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 711
guauggugcg gaggc                                          15

<210> SEQ ID NO 712
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 712

-continued uauggugcgg aggcc                                               15

<210> SEQ ID NO 713
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 713
auggugcgga ggccc                                               15

<210> SEQ ID NO 714
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 714
uggugcggag gcccu                                               15

<210> SEQ ID NO 715
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 715
ggugcggagg cccug                                               15

<210> SEQ ID NO 716
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 716
gugcggaggc ccugg                                               15

<210> SEQ ID NO 717
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 717
ugcggaggcc cugga                                               15

<210> SEQ ID NO 718
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 718
gcggaggccc uggag                                                15

<210> SEQ ID NO 719
<211> LENGTH: 15
<212> TYPE: DNA
<213> ORGANISM: artificial sequences
<220> FEATURE:
<223> OTHER INFORMATION: 15mer sense oligonucelotides which represent
      targets on HBA2 mRNA

<400> SEQUENCE: 719
cggaggcccu ggaga                                                15

<210> SEQ ID NO 720
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 720
ggaggcccug gagag                                                15

<210> SEQ ID NO 721
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 721
gaggcccugg agagg                                                15

<210> SEQ ID NO 722
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 722
aggcccugga gagga                                                15

<210> SEQ ID NO 723
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 723
ggcccuggag aggau                                                15

<210> SEQ ID NO 724
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 724
gcccuggaga ggaug                                                15

<210> SEQ ID NO 725
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 725
cccuggagag gaugu                                                  15

<210> SEQ ID NO 726
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 726
ccuggagagg auguu                                                  15

<210> SEQ ID NO 727
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 727
cuggagagga uguuc                                                  15

<210> SEQ ID NO 728
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 728
uggagaggau guucc                                                  15

<210> SEQ ID NO 729
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 729
ggagaggaug uuccu                                                  15

<210> SEQ ID NO 730
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 730
gagaggaugu uccug                                                  15

<210> SEQ ID NO 731
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 731
agaggauguu ccugu                                                      15

<210> SEQ ID NO 732
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 732
gaggauguuc cuguc                                                      15

<210> SEQ ID NO 733
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 733
aggauguucc ugucc                                                      15

<210> SEQ ID NO 734
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 734
ggauguuccu guccu                                                      15

<210> SEQ ID NO 735
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 735 gauguccug uccuu                                                       15

<210> SEQ ID NO 736
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 736 auguccugu ccuuc                                                       15

```
<210> SEQ ID NO 737
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 737
uguuccuguc cuucc                                                          15

<210> SEQ ID NO 738
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 738
guuccugucc uuccc                                                          15

<210> SEQ ID NO 739
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 739
uuccuguccu ucccc                                                          15

<210> SEQ ID NO 740
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 740
uccuguccuu cccca                                                          15

<210> SEQ ID NO 741
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 741
ccuguccuuc cccac                                                          15

<210> SEQ ID NO 742
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 742
cuguccuucc ccacc                                                          15

<210> SEQ ID NO 743
```

```
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 743
uguccuuccc cacca                                                          15

<210> SEQ ID NO 744
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 744
guccuucccc accac                                                          15

<210> SEQ ID NO 745
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 745
uccuucccca ccacc                                                          15

<210> SEQ ID NO 746
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 746
ccuuccccac cacca                                                          15

<210> SEQ ID NO 747
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 747
cuuccccacc accaa                                                          15

<210> SEQ ID NO 748
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 748
uuccccacca ccaag                                                          15

<210> SEQ ID NO 749
<211> LENGTH: 15
```

```
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 749
tccccaccac caaga                                                      15

<210> SEQ ID NO 750
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 750
ccccaccacc aagac                                                      15

<210> SEQ ID NO 751
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 751
cccaccacca agacc                                                      15

<210> SEQ ID NO 752
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 752
ccaccaccaa gaccu                                                      15

<210> SEQ ID NO 753
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 753
caccaccaag accua                                                      15

<210> SEQ ID NO 754
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 754
accaccaaga ccuac                                                      15

<210> SEQ ID NO 755
<211> LENGTH: 15
<212> TYPE: DNA
```

```
<213> ORGANISM: artificial sequence
<220> FEATURE:
<223> OTHER INFORMATION: 15mer sense oligonucelotides which represent
      targets on HBA2 mRNA

<400> SEQUENCE: 755
ccaccaagac cuacu                                                        15

<210> SEQ ID NO 756
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 756
caccaagacc uacuu                                                        15

<210> SEQ ID NO 757
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 757
accaagaccu acuuc                                                        15

<210> SEQ ID NO 758
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 758
ccaagaccua cuucc                                                        15

<210> SEQ ID NO 759
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 759
caagaccuac uuccc                                                        15

<210> SEQ ID NO 760
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 760 aagaccuacuucccg                                                         15

<210> SEQ ID NO 761
<211> LENGTH: 15
<212> TYPE: DNA
<213> ORGANISM: artificial sequence
```

```
<220> FEATURE:
<223> OTHER INFORMATION: 15mer sense oligonucelotides which represent
      targets on HBA2 mRNA

<400> SEQUENCE: 761
agaccuacuu cccgc                                                          15

<210> SEQ ID NO 762
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 762
gaccuacuuc ccgca                                                          15

<210> SEQ ID NO 763
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 763
accuacuucc cgcac                                                          15

<210> SEQ ID NO 764
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 764
ccuacuuccc gcacu                                                          15

<210> SEQ ID NO 765
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 765
cuacuucccg cacuu                                                          15

<210> SEQ ID NO 766
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 766
uacuucccgc acuuc                                                          15

<210> SEQ ID NO 767
<211> LENGTH: 15
<212> TYPE: DNA
<213> ORGANISM: artificial sequence
<220> FEATURE:
```

```
<223> OTHER INFORMATION: 15mer sense oligonucelotides which represent
      targets on HBA2 mRNA

<400> SEQUENCE: 767
acuucccgca cuucg                                                          15

<210> SEQ ID NO 768
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 768
cuucccgcac uucga                                                          15

<210> SEQ ID NO 769
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 769
uucccgcacu ucgac                                                          15

<210> SEQ ID NO 770
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 770
ucccgcacuu cgacc                                                          15

<210> SEQ ID NO 771
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 771
cccgcacuuc gaccu                                                          15

<210> SEQ ID NO 772
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 772
ccgcacuucg accug                                                          15

<210> SEQ ID NO 773
<211> LENGTH: 15
<212> TYPE: DNA
<213> ORGANISM: artificial sequence
<220> FEATURE:
<223> OTHER INFORMATION: 15mer sense oligonucelotides which represent
``` targets on HBA2 mRNA

<400> SEQUENCE: 773
cgcacuucga ccuga                                                 15

<210> SEQ ID NO 774
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 774
gcacuucgac cugag                                                 15

<210> SEQ ID NO 775
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 775
cacuucgacc ugagc                                                 15

<210> SEQ ID NO 776
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 776
acuucgaccu gagcc                                                 15

<210> SEQ ID NO 777
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 777
cuucgaccug agcca                                                 15

<210> SEQ ID NO 778
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 778
uucgaccuga gccac                                                 15

<210> SEQ ID NO 779
<211> LENGTH: 14
<212> TYPE: DNA
<213> ORGANISM: artificial sequence
<220> FEATURE:
<223> OTHER INFORMATION: 15mer sense oligonucelotides which represent
      targets on HBA2 mRNA

```
<400> SEQUENCE: 779
ucgaccugag ccac                                                     14

<210> SEQ ID NO 780
<211> LENGTH: 14
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 780
cgaccugagc cacg                                                     14

<210> SEQ ID NO 781
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 781
gaccugagcc acggc                                                    15

<210> SEQ ID NO 782
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 782
accugagcca cggcu                                                    15

<210> SEQ ID NO 783
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 783
ccugagccac ggcuc                                                    15

<210> SEQ ID NO 784
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 784
cugagccacg gcucu                                                    15

<210> SEQ ID NO 785
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA
```

```
<400> SEQUENCE: 785
ugagccacgg cucug                                              15

<210> SEQ ID NO 786
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 786
gagccacggc ucugc                                              15

<210> SEQ ID NO 787
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 787
agccacggcu cugcc                                              15

<210> SEQ ID NO 788
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 788
gccacggcuc ugccc                                              15

<210> SEQ ID NO 789
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 789
ccacggcucu gccca                                              15

<210> SEQ ID NO 790
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 790
cacggcucug cccag                                              15

<210> SEQ ID NO 791
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 791
```

```
acggcucugc ccagg                                                  15
```

<210> SEQ ID NO 792
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 792

```
cggcucugcc caggu                                                  15
```

<210> SEQ ID NO 793
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 793

```
ggcucugccc agguu                                                  15
```

<210> SEQ ID NO 794
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 794

```
gcucugccca gguua                                                  15
```

<210> SEQ ID NO 795
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 795

```
cucugcccag guuaa                                                  15
```

<210> SEQ ID NO 796
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 796

```
ucugcccagg uuaag                                                  15
```

<210> SEQ ID NO 797
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 797
cugcccaggu uaagg					15

<210> SEQ ID NO 798
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 798
ugcccagguu aaggg					15

<210> SEQ ID NO 799
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 799
gcccagguua agggc					15

<210> SEQ ID NO 800
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 800
cccagguuaa gggcc					15

<210> SEQ ID NO 801
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 801
ccagguuaag ggcca					15

<210> SEQ ID NO 802
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 802
cagguuaagg gccac					15

<210> SEQ ID NO 803
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 803
agguuaaggg ccacg					15

<210> SEQ ID NO 804
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 804
gguuaagggc cacgg                                                15

<210> SEQ ID NO 805
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 805
guuaagggcc acggc                                                15

<210> SEQ ID NO 806
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 806
uuaagggcca cggca                                                15

<210> SEQ ID NO 807
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 807
uaagggccac ggcaa                                                15

<210> SEQ ID NO 808
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 808
aagggccacg gcaag                                                15

<210> SEQ ID NO 809
<211> LENGTH: 15
<212> TYPE: DNA
<213> ORGANISM: aruificial sequence
<220> FEATURE:
<223> OTHER INFORMATION: 15mer sense oligonucelotides which represent
      targets on HBA2 mRNA

<400> SEQUENCE: 809
agggccacgg caaga                                                15

<210> SEQ ID NO 810
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 810
gggccacggc aagaa                                              15

<210> SEQ ID NO 811
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 811
ggccacggca agaag                                              15

<210> SEQ ID NO 812
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 812
gccacggcaa gaagg                                              15

<210> SEQ ID NO 813
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 813
ccacggcaag aaggu                                              15

<210> SEQ ID NO 814
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 814
cacggcaaga aggug                                              15

<210> SEQ ID NO 815
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 815
acggcaagaa ggugg                                              15

-continued

<210> SEQ ID NO 816
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 816
cggcaagaag guggc                                                    15

<210> SEQ ID NO 817
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 817
ggcaagaagg uggcc                                                    15

<210> SEQ ID NO 818
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 818
gcaagaaggu ggccg                                                    15

<210> SEQ ID NO 819
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 819
caagaaggug gccga                                                    15

<210> SEQ ID NO 820
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 820
aagaaggugg ccgac                                                    15

<210> SEQ ID NO 821
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 821 agaaggugge cgacg                                                    15

<210> SEQ ID NO 822

```
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 822
gaagguggcc gacgc                                                          15

<210> SEQ ID NO 823
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 823
aagguggccg acgcg                                                          15

<210> SEQ ID NO 824
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 824
agguggccga cgcgc                                                          15

<210> SEQ ID NO 825
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 825
gguggccgac gcgcu                                                          15

<210> SEQ ID NO 826
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 826
guggccgacg cgcug                                                          15

<210> SEQ ID NO 827
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 827
uggccgacgc gcuga                                                          15

<210> SEQ ID NO 828
<211> LENGTH: 15
```

```
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 828
ggccgacgcg cugac                                                      15

<210> SEQ ID NO 829
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 829
gccgacgcgc ugacc                                                      15

<210> SEQ ID NO 830
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 830
ccgacgcgcu gacca                                                      15

<210> SEQ ID NO 831
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 831
cgacgcgcug accaa                                                      15

<210> SEQ ID NO 832
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 832
gacgcgcuga ccaac                                                      15

<210> SEQ ID NO 833
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 833
acgcgcugac caacg                                                      15

<210> SEQ ID NO 834
<211> LENGTH: 15
<212> TYPE: DNA
```

```
<213> ORGANISM: artificial sequence
<220> FEATURE:
<223> OTHER INFORMATION: 15mer sense oligonucelotides which represent
      targets on HBA2 mRNA

<400> SEQUENCE: 834
cgcgcugacc aacgc                                                         15

<210> SEQ ID NO 835
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 835
gcgcugacca acgcc                                                         15

<210> SEQ ID NO 836
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 836
cgcugaccaa cgccg                                                         15

<210> SEQ ID NO 837
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 837
gcugaccaac gccgu                                                         15

<210> SEQ ID NO 838
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 838
cugaccaacg ccgug                                                         15

<210> SEQ ID NO 839
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 839
ugaccaacgc cgugg                                                         15

<210> SEQ ID NO 840
<211> LENGTH: 15
<212> TYPE: DNA
<213> ORGANISM: artificial sequence
```

```
<220> FEATURE:
<223> OTHER INFORMATION: 15mer sense oligonucelotides which represent
      targets on HBA2 mRNA

<400> SEQUENCE: 840
gaccaacgcc guggc                                                       15

<210> SEQ ID NO 841
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 841
accaacgccg uggcg                                                       15

<210> SEQ ID NO 842
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 842
ccaacgccgu ggcgc                                                       15

<210> SEQ ID NO 843
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 843
caacgccgug gcgca                                                       15

<210> SEQ ID NO 844
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 844
aacgccgugg cgcac                                                       15

<210> SEQ ID NO 845
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 845
acgccguggc gcacg                                                       15

<210> SEQ ID NO 846
<211> LENGTH: 15
<212> TYPE: DNA
<213> ORGANISM: artificial sequence
<220> FEATURE:
```

```
<223> OTHER INFORMATION: 15mer sense oligonucelotides which represent
      targets on HBA2 mRNA

<400> SEQUENCE: 846
cgccguggcg cacgu                                                     15

<210> SEQ ID NO 847
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 847
gccguggcgc acgug                                                     15

<210> SEQ ID NO 848
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 848
ccguggcgca cgugg                                                     15

<210> SEQ ID NO 849
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 849
cguggcgcac gugga                                                     15

<210> SEQ ID NO 850
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 850
guggcgcacg uggac                                                     15

<210> SEQ ID NO 851
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 851
uggcgcacgu ggacg                                                     15

<210> SEQ ID NO 852
<211> LENGTH: 15
<212> TYPE: DNA
<213> ORGANISM: artificial sequence
<220> FEATURE:
<223> OTHER INFORMATION: 15mer sense oligonucelotides which represent
``` targets on HBA2 mRNA

<400> SEQUENCE: 852
ggcgcacgug gacga                                                    15

<210> SEQ ID NO 853
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 853
gcgcacgugg acgac                                                    15

<210> SEQ ID NO 854
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 854
cgcacgugga cgaca                                                    15

<210> SEQ ID NO 855
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 855
gcacguggac gacau                                                    15

<210> SEQ ID NO 856
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 856
cacguggacg acaug                                                    15

<210> SEQ ID NO 857
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 857
acguggacga caugc                                                    15

<210> SEQ ID NO 858
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA -continued

<400> SEQUENCE: 858
cguggacgac augcc                                                    15

<210> SEQ ID NO 859
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 859
guggacgaca ugccc                                                    15

<210> SEQ ID NO 860
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 860
uggacgacau gccca                                                    15

<210> SEQ ID NO 861
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 861
ggacgacaug cccaa                                                    15

<210> SEQ ID NO 862
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 862
gacgacaugc ccaac                                                    15

<210> SEQ ID NO 863
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 863
acgacaugcc caacg                                                    15

<210> SEQ ID NO 864
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

```
<400> SEQUENCE: 864
cgacaugccc aacgc                                                    15

<210> SEQ ID NO 865
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 865
gacaugccca acgcg                                                    15

<210> SEQ ID NO 866
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 866
acaugcccaa cgcgc                                                    15

<210> SEQ ID NO 867
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 867
caugcccaac gcgcu                                                    15

<210> SEQ ID NO 868
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 868
augcccaacg cgcug                                                    15

<210> SEQ ID NO 869
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 869
ugcccaacgc gcugu                                                    15

<210> SEQ ID NO 870
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 870
```
gcccaacgcg cuguc    15

<210> SEQ ID NO 871
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 871
cccaacgcgc ugucc    15

<210> SEQ ID NO 872
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 872
ccaacgcgcu guccg    15

<210> SEQ ID NO 873
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 873
caacgcgcug uccgc    15

<210> SEQ ID NO 874
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 874
aacgcgcugu ccgcc    15

<210> SEQ ID NO 875
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA1 mRNA

<400> SEQUENCE: 875
acgcgcuguc cgccc    15

<210> SEQ ID NO 876
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 876
cgcgcugucc gcccu 15

<210> SEQ ID NO 877
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 877
gcgcuguccg cccug 15

<210> SEQ ID NO 878
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 878
cgcuguccgc ccuga 15

<210> SEQ ID NO 879
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 879
gcuguccgcc cugag 15

<210> SEQ ID NO 880
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 880
cuguccgccc ugagc 15

<210> SEQ ID NO 881
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 881
uguccgcccu gagcg 15

<210> SEQ ID NO 882
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 882
guccgcccug agcga 15

<210> SEQ ID NO 883
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 883
uccgcccuga gcgac                                                     15

<210> SEQ ID NO 884
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 884
ccgcccugag cgacc                                                     15

<210> SEQ ID NO 885
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 885
cgcccugagc gaccu                                                     15

<210> SEQ ID NO 886
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 886
gcccugagcg accug                                                     15

<210> SEQ ID NO 887
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 887
cccugagcga ccugc                                                     15

<210> SEQ ID NO 888
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 888
ccugagcgac cugca                                                     15

<210> SEQ ID NO 889
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 889
cugagcgacc ugcac                                                        15

<210> SEQ ID NO 890
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 890
ugagcgaccu gcacg                                                        15

<210> SEQ ID NO 891
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA1 mRNA

<400> SEQUENCE: 891
gagcgaccug cacgc                                                        15

<210> SEQ ID NO 892
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 892
agcgaccugc acgcg                                                        15

<210> SEQ ID NO 893
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 893
gcgaccugca cgcgc                                                        15

<210> SEQ ID NO 894
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 894
cgaccugcac gcgca                                                        15

```
<210> SEQ ID NO 895
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 895
gaccugcacg cgcac                                                        15

<210> SEQ ID NO 896
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 896
accugcacgc gcaca                                                        15

<210> SEQ ID NO 897
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 897
ccugcacgcg cacaa                                                        15

<210> SEQ ID NO 898
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 898
cugcacgcgc acaag                                                        15

<210> SEQ ID NO 899
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 899
ugcacgcgca caagc                                                        15

<210> SEQ ID NO 900
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 900
gcacgcgcac aagcu                                                        15

<210> SEQ ID NO 901
```

<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 901
cacgcgcaca agcuu                                                         15

<210> SEQ ID NO 902
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 902
acgcgcacaa gcuuc                                                         15

<210> SEQ ID NO 903
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 903
cgcgcacaag cuucg                                                         15

<210> SEQ ID NO 904
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 904
gcgcacaagc uucgg                                                         15

<210> SEQ ID NO 905
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 905
cgcacaagcu ucggg                                                         15

<210> SEQ ID NO 906
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 906
gcacaagcuu cgggu                                                         15

<210> SEQ ID NO 907
<211> LENGTH: 15

```
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 907
cacaagcuuc gggug                                                      15

<210> SEQ ID NO 908
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 908
acaagcuucg ggugg                                                      15

<210> SEQ ID NO 909
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 909
caagcuucgg gugga                                                      15

<210> SEQ ID NO 910
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 910
aagcuucggg uggac                                                      15

<210> SEQ ID NO 911
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 911
agcuucgggu ggacc                                                      15

<210> SEQ ID NO 912
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 912
gcuucgggug gaccc                                                      15

<210> SEQ ID NO 913
<211> LENGTH: 15
<212> TYPE: DNA
```

```
<213> ORGANISM: artificial sequence
<220> FEATURE:
<223> OTHER INFORMATION: 15mer sense oligonucelotides which represent
      targets on HBA2 mRNA

<400> SEQUENCE: 913
cuucgggugg acccg                                                          15

<210> SEQ ID NO 914
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 914
uucgggugga cccgg                                                          15

<210> SEQ ID NO 915
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 915
ucggguggac ccggu                                                          15

<210> SEQ ID NO 916
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 916
cggguggacc cgguc                                                          15

<210> SEQ ID NO 917
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 917
ggguggaccc gguca                                                          15

<210> SEQ ID NO 918
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 918
gguggacccg gucaa                                                          15

<210> SEQ ID NO 919
<211> LENGTH: 15
<212> TYPE: DNA
<213> ORGANISM: artificial sequence
```

```
<220> FEATURE:
<223> OTHER INFORMATION: 15mer sense oligonucelotides which represent
      targets on HBA2 mRNA

<400> SEQUENCE: 919
guggacccgg ucaac                                                      15

<210> SEQ ID NO 920
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 920
uggacccggu caacu                                                      15

<210> SEQ ID NO 921
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 921
ggacccgguc aacuu                                                      15

<210> SEQ ID NO 922
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 922
gacccgguca acuuc                                                      15

<210> SEQ ID NO 923
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 923
acccggucaa cuuca                                                      15

<210> SEQ ID NO 924
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 924
cccggucaac uucaa                                                      15

<210> SEQ ID NO 925
<211> LENGTH: 15
<212> TYPE: DNA
<213> ORGANISM: artificial sequence
<220> FEATURE:
```

-continued

<223> OTHER INFORMATION: 15mer sense oligonucelotides which represent
     targets on HBA2 mRNA

<400> SEQUENCE: 925
ccggucaacu ucaag                                                    15

<210> SEQ ID NO 926
<211> LENGTH: 15
<212> TYPE: DNA
<213> ORGANISM: artificial sequence
<220> FEATURE:
<223> OTHER INFORMATION: 15mer sense oligonucelotides which represent
     targets on HBA2 mRNA

<400> SEQUENCE: 926
cggucaacuu caagc                                                    15

<210> SEQ ID NO 927
<211> LENGTH: 15
<212> TYPE: DNA
<213> ORGANISM: artificial sequence
<220> FEATURE:
<223> OTHER INFORMATION: 15mer sense oligonucelotides which represent
     targets on HBA2 mRNA

<400> SEQUENCE: 927
ggucaacuuc aagcu                                                    15

<210> SEQ ID NO 928
<211> LENGTH: 15
<212> TYPE: DNA
<213> ORGANISM: artificial sequence
<220> FEATURE:
<223> OTHER INFORMATION: 15mer sense oligonucelotides which represent
     targets on HBA2 mRNA

<400> SEQUENCE: 928
gucaacuuca agcuc                                                    15

<210> SEQ ID NO 929
<211> LENGTH: 15
<212> TYPE: DNA
<213> ORGANISM: artificial sequence
<220> FEATURE:
<223> OTHER INFORMATION: 15mer sense oligonucelotides which represent
     targets on HBA1 mRNA

<400> SEQUENCE: 929
ucaacuucaa gcucc                                                    15

<210> SEQ ID NO 930
<211> LENGTH: 15
<212> TYPE: DNA
<213> ORGANISM: artificial sequence
<220> FEATURE:
<223> OTHER INFORMATION: 15mer sense oligonucelotides which represent
     targets on HBA2 mRNA

<400> SEQUENCE: 930
caacuucaag cuccu                                                    15

<210> SEQ ID NO 931
<211> LENGTH: 15
<212> TYPE: DNA
<213> ORGANISM: artificial sequence
<220> FEATURE:
<223> OTHER INFORMATION: 15mer sense oligonucelotides which represent -continued

```
        targets on HBA2 mRNA

<400> SEQUENCE: 931
aacuucaagc uccua                                                   15

<210> SEQ ID NO 932
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 932
acuucaagcu ccuaa                                                   15

<210> SEQ ID NO 933
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 933
cuucaagcuc cuaag                                                   15

<210> SEQ ID NO 934
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 934
uucaagcucc uaagc                                                   15

<210> SEQ ID NO 935
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 935
ucaagcuccu aagcc                                                   15

<210> SEQ ID NO 936
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 936
caagcuccua agcca                                                   15

<210> SEQ ID NO 937
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA
```

```
<400> SEQUENCE: 937
aagcuccuaa gccac                                                    15

<210> SEQ ID NO 938
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 938
agcuccuaag ccacu                                                    15

<210> SEQ ID NO 939
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 939
gcuccuaagc cacug                                                    15

<210> SEQ ID NO 940
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 940
cuccuaagcc acugc                                                    15

<210> SEQ ID NO 941
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 941
uccuaagcca cugcc                                                    15

<210> SEQ ID NO 942
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 942
ccuaagccac ugccu                                                    15

<210> SEQ ID NO 943
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA
```

```
<400> SEQUENCE: 943
cuaagccacu gccug                                                    15

<210> SEQ ID NO 944
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 944
uaagccacug ccugc                                                    15

<210> SEQ ID NO 945
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 945
aagccacugc cugcu                                                    15

<210> SEQ ID NO 946
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 946
agccacugcc ugcug                                                    15

<210> SEQ ID NO 947
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 947
gccacugccu gcugg                                                    15

<210> SEQ ID NO 948
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 948
ccacugccug cuggu                                                    15

<210> SEQ ID NO 949
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 949
```
cacugccugc uggug                                               15

<210> SEQ ID NO 950
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 950
acugccugcu gguga                                               15

<210> SEQ ID NO 951
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 951
cugccugcug gugac                                               15

<210> SEQ ID NO 952
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 952
ugccugcugg ugacc                                               15

<210> SEQ ID NO 953
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 953
gccugcuggu gaccc                                               15

<210> SEQ ID NO 954
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 954
ccugcuggug acccu                                               15

<210> SEQ ID NO 955
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 955
cugcugguga cccug                                                15

<210> SEQ ID NO 956
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 956
ugcuggugac ccugg                                                15

<210> SEQ ID NO 957
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 957
gcuggugacc cuggc                                                15

<210> SEQ ID NO 958
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 958
cuggugaccc uggcc                                                15

<210> SEQ ID NO 959
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 959
uggugacccu ggccg                                                15

<210> SEQ ID NO 960
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 960
ggugacccug gccgc                                                15

<210> SEQ ID NO 961
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 961
gugacccugg ccgcc                                                15

<210> SEQ ID NO 962
<211> LENGTH: 15
<212> TYPE: DNA
<213> ORGANISM: artificial sequence
<220> FEATURE:
<223> OTHER INFORMATION: 15mer sense oligonucelotides which represent
     targets on HBA2 mRNA

<400> SEQUENCE: 962
ugacccuggc cgccc                                                15

<210> SEQ ID NO 963
<211> LENGTH: 15
<212> TYPE: DNA
<213> ORGANISM: artificial sequence
<220> FEATURE:
<223> OTHER INFORMATION: 15mer sense oligonucelotides which represent
     targets on HBA2 mRNA

<400> SEQUENCE: 963
gacccuggcc gccca                                                15

<210> SEQ ID NO 964
<211> LENGTH: 15
<212> TYPE: DNA
<213> ORGANISM: artificial sequence
<220> FEATURE:
<223> OTHER INFORMATION: 15mer sense oligonucelotides which represent
     targets on HBA2 mRNA

<400> SEQUENCE: 964
acccuggccg cccac                                                15

<210> SEQ ID NO 965
<211> LENGTH: 15
<212> TYPE: DNA
<213> ORGANISM: artificial sequence
<220> FEATURE:
<223> OTHER INFORMATION: 15mer sense oligonucelotides which represent
     targets on HBA2 mRNA

<400> SEQUENCE: 965
cccuggccgc ccacc                                                15

<210> SEQ ID NO 966
<211> LENGTH: 15
<212> TYPE: DNA
<213> ORGANISM: artificial sequence
<220> FEATURE:
<223> OTHER INFORMATION: 15mer sense oligonucelotides which represent
     targets on HBA2 mRNA

<400> SEQUENCE: 966
ccuggccgcc cacct                                                15

<210> SEQ ID NO 967
<211> LENGTH: 15
<212> TYPE: DNA
<213> ORGANISM: artificial sequence
<220> FEATURE:
<223> OTHER INFORMATION: 15mer sense oligonucelotides which represent
     targets on HBA2 mRNA

<400> SEQUENCE: 967
cuggccgccc accuc                                                15

```
<210> SEQ ID NO 968
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 968
uggccgccca ccucc                                                    15

<210> SEQ ID NO 969
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 969
ggccgcccac cuccc                                                    15

<210> SEQ ID NO 970
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 970
gccgcccacc ucccc                                                    15

<210> SEQ ID NO 971
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 971
ccgcccaccu ccccg                                                    15

<210> SEQ ID NO 972
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 972
cgcccaccuc cccgc                                                    15

<210> SEQ ID NO 973
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 973
gcccaccucc ccgcc                                                    15
```

```
<210> SEQ ID NO 974
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 974
cccaccuccc cgccg                                                        15

<210> SEQ ID NO 975
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 975
ccaccucccc gccga                                                        15

<210> SEQ ID NO 976
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 976
caccuccccg ccgag                                                        15

<210> SEQ ID NO 977
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 977
accuccccgc cgagu                                                        15

<210> SEQ ID NO 978
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 978
ccuccccgcc gaguu                                                        15

<210> SEQ ID NO 979
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 979
cuccccgccg aguuc                                                        15

<210> SEQ ID NO 980
```

```
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 980
uccccgccga guuca                                                    15

<210> SEQ ID NO 981
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 981
ccccgccgag uucac                                                    15

<210> SEQ ID NO 982
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 982
cccgccgagu ucacc                                                    15

<210> SEQ ID NO 983
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 983
ccgccgaguu caccc                                                    15

<210> SEQ ID NO 984
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 984
cgccgaguuc acccc                                                    15

<210> SEQ ID NO 985
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 985
gccgaguuca ccccu                                                    15

<210> SEQ ID NO 986
<211> LENGTH: 15
```

```
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 986
ccgaguucac cccug                                                       15

<210> SEQ ID NO 987
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 987
cgaguucacc ccugc                                                       15

<210> SEQ ID NO 988
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 988
gaguucaccc cugcg                                                       15

<210> SEQ ID NO 989
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 989
aguucacccc ugcgg                                                       15

<210> SEQ ID NO 990
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 990
guucaccccu gcggu                                                       15

<210> SEQ ID NO 991
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 991
uucaccccug cggug                                                       15

<210> SEQ ID NO 992
<211> LENGTH: 15
<212> TYPE: DNA
```

```
<213> ORGANISM: artificial sequence
<220> FEATURE:
<223> OTHER INFORMATION: 15mer sense oligonucelotides which represent
      targets on HBA2 mRNA

<400> SEQUENCE: 992
ucaccccugc ggugc                                                      15

<210> SEQ ID NO 993
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 993
caccccugcg gugca                                                      15

<210> SEQ ID NO 994
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 994
accccugcgg ugcac                                                      15

<210> SEQ ID NO 995
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 995
ccccugcggu gcacg                                                      15

<210> SEQ ID NO 996
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 996
cccugcggug cacgc                                                      15

<210> SEQ ID NO 997
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 997
ccugcggugc acgcc                                                      15

<210> SEQ ID NO 998
<211> LENGTH: 15
<212> TYPE: DNA
<213> ORGANISM: artificial sequence
```

```
<220> FEATURE:
<223> OTHER INFORMATION: 15mer sense oligonucelotides which represent
      targets on HBA2 mRNA

<400> SEQUENCE: 998
cugcggugca cgccu                                                      15

<210> SEQ ID NO 999
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 999
ugcggugcac gccuc                                                      15

<210> SEQ ID NO 1000
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1000
gcggugcacg ccucc                                                      15

<210> SEQ ID NO 1001
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1001
cggugcacgc cuccc                                                      15

<210> SEQ ID NO 1002
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1002
ggugcacgcc ucccu                                                      15

<210> SEQ ID NO 1003
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1003
gugcacgccu cccug                                                      15

<210> SEQ ID NO 1004
<211> LENGTH: 15
<212> TYPE: DNA
<213> ORGANISM: artificial sequence
<220> FEATURE:
```

```
<223> OTHER INFORMATION: 15mer sense oligonucelotides which represent
      targets on HBA2 mRNA

<400> SEQUENCE: 1004
ugcacgccuc ccugg                                                          15

<210> SEQ ID NO 1005
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1005
gcacgccucc cugga                                                          15

<210> SEQ ID NO 1006
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1006
cacgccuccc uggac                                                          15

<210> SEQ ID NO 1007
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1007
acgccucccu ggaca                                                          15

<210> SEQ ID NO 1008
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1008
cgccucccug gacaa                                                          15

<210> SEQ ID NO 1009
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1009
gccucccugg acaag                                                          15

<210> SEQ ID NO 1010
<211> LENGTH: 15
<212> TYPE: DNA
<213> ORGANISM: artificial sequence
<220> FEATURE:
<223> OTHER INFORMATION: 15mer sense oligonucelotides which represent
``` targets on HBA2 mRNA

<400> SEQUENCE: 1010
ccucccugga caagu                                                    15

<210> SEQ ID NO 1011
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1011
cucccuggac aaguu                                                    15

<210> SEQ ID NO 1012
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1012
ucccuggaca aguuc                                                    15

<210> SEQ ID NO 1013
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1013
cccuggacaa guucc                                                    15

<210> SEQ ID NO 1014
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA1 mRNA

<400> SEQUENCE: 1014
ccuggacaag uuccu                                                    15

<210> SEQ ID NO 1015
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1015
cuggacaagu uccug                                                    15

<210> SEQ ID NO 1016
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

```
<400> SEQUENCE: 1016
uggacaaguu ccugg                                                    15

<210> SEQ ID NO 1017
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1017
ggacaaguuc cuggc                                                    15

<210> SEQ ID NO 1018
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1018
gacaaguucc uggcu                                                    15

<210> SEQ ID NO 1019
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1019
acaaguuccu ggcuu                                                    15

<210> SEQ ID NO 1020
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1020
caaguuccug gcuuc                                                    15

<210> SEQ ID NO 1021
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1021
aaguuccugg cuucu                                                    15

<210> SEQ ID NO 1022
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA
```

```
<400> SEQUENCE: 1022
aguuccuggc uucug                                              15

<210> SEQ ID NO 1023
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1023
guuccuggcu ucugu                                              15

<210> SEQ ID NO 1024
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1024
uuccuggcuu cugug                                              15

<210> SEQ ID NO 1025
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1025
uccuggcuuc uguga                                              15

<210> SEQ ID NO 1026
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1026
ccuggcuucu gugag                                              15

<210> SEQ ID NO 1027
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1027
cuggcuucug ugagc                                              15

<210> SEQ ID NO 1028
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1028
```
uggcuucugu gagca 15

<210> SEQ ID NO 1029
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1029
ggcuucugug agcac 15

<210> SEQ ID NO 1030
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1030
gcuucuguga gcacc 15

<210> SEQ ID NO 1031
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1031
cuucugugag caccg 15

<210> SEQ ID NO 1032
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1032
uucugugagc accgu 15

<210> SEQ ID NO 1033
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1033
ucugugagca ccgug 15

<210> SEQ ID NO 1034
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1034
cugugagcac cgugc                                                15

<210> SEQ ID NO 1035
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1035
ugugagcacc gugcu                                                15

<210> SEQ ID NO 1036
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1036
gugagcaccg ugcug                                                15

<210> SEQ ID NO 1037
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1037
ugagcaccgu gcuga                                                15

<210> SEQ ID NO 1038
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1038
gagcaccgug cugac                                                15

<210> SEQ ID NO 1039
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1039
agcaccgugc ugacc                                                15

<210> SEQ ID NO 1040
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1040
gcaccgugcu gaccu                                                15

<210> SEQ ID NO 1041
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1041
caccgugcug accuc                                                      15

<210> SEQ ID NO 1042
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1042
accgugcuga ccucc                                                      15

<210> SEQ ID NO 1043
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1043
ccgugcugac cucca                                                      15

<210> SEQ ID NO 1044
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1044
cgugcugacc uccaa                                                      15

<210> SEQ ID NO 1045
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1045
gugcugaccu ccaaa                                                      15

<210> SEQ ID NO 1046
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1046
ugcugaccuc caaau                                                      15

<210> SEQ ID NO 1047
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1047
gcugaccucc aaaua                                                          15

<210> SEQ ID NO 1048
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1048
cugaccucca aauac                                                          15

<210> SEQ ID NO 1049
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1049
ugaccuccaa auacc                                                          15

<210> SEQ ID NO 1050
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1050
gaccuccaaa uaccg                                                          15

<210> SEQ ID NO 1051
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1051
accuccaaau accgu                                                          15

<210> SEQ ID NO 1052
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1052
ccuccaaaua ccguu                                                          15

```
<210> SEQ ID NO 1053
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1053
cuccaaauac cguua                                                          15

<210> SEQ ID NO 1054
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1054
uccaaauacc guuaa                                                          15

<210> SEQ ID NO 1055
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1055
ccaaauaccg uuaag                                                          15

<210> SEQ ID NO 1056
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1056
caaauaccgu uaagc                                                          15

<210> SEQ ID NO 1057
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1057
aaauaccguu aagcu                                                          15

<210> SEQ ID NO 1058
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1058
aauaccguua agcug                                                          15

<210> SEQ ID NO 1059
```

```
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1059
auaccguuaa gcugg                                                          15

<210> SEQ ID NO 1060
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1060
uaccguuaag cugga                                                          15

<210> SEQ ID NO 1061
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1061
accguuaagc uggag                                                          15

<210> SEQ ID NO 1062
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1062
ccguuaagcu ggagc                                                          15

<210> SEQ ID NO 1063
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1063
cguuaagcug gagcc                                                          15

<210> SEQ ID NO 1064
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1064
guuaagcugg agccu                                                          15

<210> SEQ ID NO 1065
<211> LENGTH: 15
```

```
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1065
uuaagcugga gccuc                                                   15

<210> SEQ ID NO 1066
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1066
uaagcuggag ccucg                                                   15

<210> SEQ ID NO 1067
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1067
aagcuggagc cucgg                                                   15

<210> SEQ ID NO 1068
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1068
agcuggagcc ucggu                                                   15

<210> SEQ ID NO 1069
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1069
gcuggagccu cggua                                                   15

<210> SEQ ID NO 1070
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1070
cuggagccuc gguag                                                   15

<210> SEQ ID NO 1071
<211> LENGTH: 15
<212> TYPE: DNA
```

```
<213> ORGANISM: artificial sequence
<220> FEATURE:
<223> OTHER INFORMATION: 15mer sense oligonucelotides which represent
      targets on HBA2 mRNA

<400> SEQUENCE: 1071
uggagccucg guagc                                                         15

<210> SEQ ID NO 1072
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1072
ggagccucgg uagcc                                                         15

<210> SEQ ID NO 1073
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1073
gagccucggu agccg                                                         15

<210> SEQ ID NO 1074
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1074
agccucggua gccgu                                                         15

<210> SEQ ID NO 1075
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1075
gccucgguag ccguu                                                         15

<210> SEQ ID NO 1076
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1076
ccucgguagc cguuc                                                         15

<210> SEQ ID NO 1077
<211> LENGTH: 15
<212> TYPE: DNA
<213> ORGANISM: artificial sequence
```

```
<220> FEATURE:
<223> OTHER INFORMATION: 15mer sense oligonucelotides which represent
      targets on HBA2 mRNA

<400> SEQUENCE: 1077
cucgguagcc guucc                                                          15

<210> SEQ ID NO 1078
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1078
ucgguagccg uuccu                                                          15

<210> SEQ ID NO 1079
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1079
cgguagccgu uccuc                                                          15

<210> SEQ ID NO 1080
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1080
gguagccguu ccucc                                                          15

<210> SEQ ID NO 1081
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1081
guagccguuc cuccu                                                          15

<210> SEQ ID NO 1082
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1082
uagccguucc uccug                                                          15

<210> SEQ ID NO 1083
<211> LENGTH: 15
<212> TYPE: DNA
<213> ORGANISM: artificial sequence
<220> FEATURE:
```

```
<223> OTHER INFORMATION: 15mer sense oligonucelotides which represent
      targets on HBA2 mRNA

<400> SEQUENCE: 1083
agccguuccu ccugc                                                      15

<210> SEQ ID NO 1084
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1084
gccguuccuc cugcc                                                      15

<210> SEQ ID NO 1085
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1085
ccguuccucc ugccc                                                      15

<210> SEQ ID NO 1086
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1086
cguuccuccu gcccg                                                      15

<210> SEQ ID NO 1087
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1087
guuccuccug cccgc                                                      15

<210> SEQ ID NO 1088
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1088
uuccuccugc ccgcu                                                      15

<210> SEQ ID NO 1089
<211> LENGTH: 15
<212> TYPE: DNA
<213> ORGANISM: artificial sequence
<220> FEATURE:
<223> OTHER INFORMATION: 15mer sense oligonucelotides which represent
``` targets on HBA2 mRNA

<400> SEQUENCE: 1089
uccuccugcc cgcug                    15

<210> SEQ ID NO 1090
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1090
ccuccugccc gcugg                    15

<210> SEQ ID NO 1091
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1091
cuccugcccg cuggg                    15

<210> SEQ ID NO 1092
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1092
uccugcccgc ugggc                    15

<210> SEQ ID NO 1093
<211> LENGTH: 15
<212> TYPE: DNA
<213> ORGANISM: artificial sequebnce
<220> FEATURE:
<223> OTHER INFORMATION: 15mer sense oligonucelotides which represent
      targets on HBA2 mRNA

<400> SEQUENCE: 1093
ccugcccgcu gggcc                    15

<210> SEQ ID NO 1094
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1094
cugcccgcug ggccu                    15

<210> SEQ ID NO 1095
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1095
ugcccgcugg gccuc					15

<210> SEQ ID NO 1096
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1096
gcccgcuggg ccucc					15

<210> SEQ ID NO 1097
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1097
cccgcugggc cuccc					15

<210> SEQ ID NO 1098
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1098
ccgcugggcc uccca					15

<210> SEQ ID NO 1099
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1099
cgcugggccu cccaa					15

<210> SEQ ID NO 1100
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1100
gcugggccuc ccaac					15

<210> SEQ ID NO 1101
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

```
-continued

<400> SEQUENCE: 1101
cugggccucc caacg                                                     15

<210> SEQ ID NO 1102
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1102
ugggccuccc aacgg                                                     15

<210> SEQ ID NO 1103
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1103
gggccuccca acggg                                                     15

<210> SEQ ID NO 1104
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1104
ggccucccaa cgggc                                                     15

<210> SEQ ID NO 1105
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1105
gccucccaac gggcc                                                     15

<210> SEQ ID NO 1106
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1106
ccucccaacg ggccc                                                     15

<210> SEQ ID NO 1107
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1107
```
cucccaacgg gcccu                                                     15

<210> SEQ ID NO 1108
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1108
ucccaacggg cccuc                                                     15

<210> SEQ ID NO 1109
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1109
cccaacgggc ccucc                                                     15

<210> SEQ ID NO 1110
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1110
ccaacgggcc cuccu                                                     15

<210> SEQ ID NO 1111
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1111
caacgggccc uccuc                                                     15

<210> SEQ ID NO 1112
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1112
aacgggcccu ccucc                                                     15

<210> SEQ ID NO 1113
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1113 acgggccuc cuccc                                                  15

<210> SEQ ID NO 1114
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1114
cgggcccucc uccc                                                  15

<210> SEQ ID NO 1115
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1115
gggcccuccu cccu                                                  15

<210> SEQ ID NO 1116
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1116
ggcccuccuc cccuc                                                 15

<210> SEQ ID NO 1117
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1117
gcccuccucc ccucc                                                 15

<210> SEQ ID NO 1118
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1118
cccuccuccc cuccu                                                 15

<210> SEQ ID NO 1119
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1119
ccuccucccc uccuu                                                 15

<210> SEQ ID NO 1120
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1120
cuccuccccu ccuug                                                  15

<210> SEQ ID NO 1121
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1121
uccuccccuc cuugc                                                  15

<210> SEQ ID NO 1122
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1122
ccuccccucc uugca                                                  15

<210> SEQ ID NO 1123
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1123
cuccccuccu ugcac                                                  15

<210> SEQ ID NO 1124
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1124
uccccuccuu gcacc                                                  15

<210> SEQ ID NO 1125
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1125
ccccuccuug caccg                                                  15

<210> SEQ ID NO 1126
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1126
cccuccuugc accgg                                                    15

<210> SEQ ID NO 1127
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1127
ccuccuugca ccggc                                                    15

<210> SEQ ID NO 1128
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1128
cuccuugcac cggcc                                                    15

<210> SEQ ID NO 1129
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1129
uccuugcacc ggccc                                                    15

<210> SEQ ID NO 1130
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1130
ccuugcaccg gcccu                                                    15

<210> SEQ ID NO 1131
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1131
cuugcaccgg cccuu                                                    15

-continued

```
<210> SEQ ID NO 1132
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1132
uugcaccggc ccuuc                                                      15

<210> SEQ ID NO 1133
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1133
ugcaccggcc cuucc                                                      15

<210> SEQ ID NO 1134
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1134
gcaccggccc uuccu                                                      15

<210> SEQ ID NO 1135
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1135
caccggcccu uccug                                                      15

<210> SEQ ID NO 1136
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1136
accggcccuu ccugg                                                      15

<210> SEQ ID NO 1137
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1137
ccggcccuuc cuggu                                                      15

<210> SEQ ID NO 1138
```

```
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1138
cggcccuucc ugguc                                                   15

<210> SEQ ID NO 1139
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1139
ggcccuuccu ggucu                                                   15

<210> SEQ ID NO 1140
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1140
gcccuuccug gucuu                                                   15

<210> SEQ ID NO 1141
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1141
cccuuccugg ucuuu                                                   15

<210> SEQ ID NO 1142
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1142
ccuuccuggu cuuug                                                   15

<210> SEQ ID NO 1143
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1143
cuuccugguc uuuga                                                   15

<210> SEQ ID NO 1144
<211> LENGTH: 15
```

```
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1144
uuccuggucu uugaa                                                        15

<210> SEQ ID NO 1145
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1145
uccuggucuu ugaau                                                        15

<210> SEQ ID NO 1146
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1146
ccuggucuuu gaaua                                                        15

<210> SEQ ID NO 1147
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1147
cuggucuuug aauaa                                                        15

<210> SEQ ID NO 1148
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1148
uggucuuuga auaaa                                                        15

<210> SEQ ID NO 1149
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1149
ggucuuugaa uaaag                                                        15

<210> SEQ ID NO 1150
<211> LENGTH: 15
<212> TYPE: DNA
```

```
<213> ORGANISM: artificial sequence
<220> FEATURE:
<223> OTHER INFORMATION: 15mer sense oligonucelotides which represent
      targets on HBA2 mRNA

<400> SEQUENCE: 1150
gucuuugaau aaagu                                                         15

<210> SEQ ID NO 1151
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1151
ucuuugaaua aaguc                                                         15

<210> SEQ ID NO 1152
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1152
cuuugaauaa agucu                                                         15

<210> SEQ ID NO 1153
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1153
uuugaauaaa gucug                                                         15

<210> SEQ ID NO 1154
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1154
uugaauaaag ucuga                                                         15

<210> SEQ ID NO 1155
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1155
ugaauaaagu cugag                                                         15

<210> SEQ ID NO 1156
<211> LENGTH: 15
<212> TYPE: DNA
<213> ORGANISM: artificial sequence
```

<220> FEATURE:
<223> OTHER INFORMATION: 15mer sense oligonucelotides which represent
     targets on HBA2 mRNA

<400> SEQUENCE: 1156
gaauaaaguc ugagu                                                    15

<210> SEQ ID NO 1157
<211> LENGTH: 15
<212> TYPE: DNA
<213> ORGANISM: artificial sequence
<220> FEATURE:
<223> OTHER INFORMATION: 15mer sense oligonucelotides which represent
     targets on HBA2 mRNA

<400> SEQUENCE: 1157
aauaaagucu gagug                                                    15

<210> SEQ ID NO 1158
<211> LENGTH: 15
<212> TYPE: DNA
<213> ORGANISM: artificial sequence
<220> FEATURE:
<223> OTHER INFORMATION: 15mer sense oligonucelotides which represent
     targets on HBA2 mRNA

<400> SEQUENCE: 1158
auaaagucug agugg                                                    15

<210> SEQ ID NO 1159
<211> LENGTH: 15
<212> TYPE: DNA
<213> ORGANISM: artificial sequence
<220> FEATURE:
<223> OTHER INFORMATION: 15mer sense oligonucelotides which represent
     targets on HBA2 mRNA

<400> SEQUENCE: 1159
uaaagucuga guggg                                                    15

<210> SEQ ID NO 1160
<211> LENGTH: 15
<212> TYPE: DNA
<213> ORGANISM: artificial sequence
<220> FEATURE:
<223> OTHER INFORMATION: 15mer sense oligonucelotides which represent
     targets on HBA2 mRNA

<400> SEQUENCE: 1160
aaagucugag ugggc                                                    15

<210> SEQ ID NO 1161
<211> LENGTH: 15
<212> TYPE: DNA
<213> ORGANISM: artificial sequence
<220> FEATURE:
<223> OTHER INFORMATION: 15mer sense oligonucelotides which represent
     targets on HBA2 mRNA

<400> SEQUENCE: 1161
aagucugagu gggca                                                    15

<210> SEQ ID NO 1162
<211> LENGTH: 15
<212> TYPE: DNA
<213> ORGANISM: artificial sequence
<220> FEATURE:

```
<223> OTHER INFORMATION: 15mer sense oligonucelotides which represent
      targets on HBA2 mRNA

<400> SEQUENCE: 1162
agucugagug ggcag                                                    15

<210> SEQ ID NO 1163
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1163
gucugagugg gcagc                                                    15

<210> SEQ ID NO 1164
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1164 ucugagugggg cagca                                                   15

<210> SEQ ID NO 1165
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1165
cugagugggc agcaa                                                    15

<210> SEQ ID NO 1166
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1166
ugagugggca gcaaa                                                    15

<210> SEQ ID NO 1167
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1167
gagugggcag caaaa                                                    15

<210> SEQ ID NO 1168
<211> LENGTH: 15
<212> TYPE: DNA
<213> ORGANISM: artificial sequence
<220> FEATURE:
<223> OTHER INFORMATION: 15mer sense oligonucelotides which represent
```

-continued targets on HBA2 mRNA

<400> SEQUENCE: 1168
agugggcagc aaaaa                                                          15

<210> SEQ ID NO 1169
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1169
gugggcagca aaaa                                                           15

<210> SEQ ID NO 1170
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1170
ugggcagcaa aaaaa                                                          15

<210> SEQ ID NO 1171
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1171
gggcagcaaa aaaaa                                                          15

<210> SEQ ID NO 1172
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1172
ggcagcaaaa aaaaa                                                          15

<210> SEQ ID NO 1173
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1173
gcagcaaaaa aaaaa                                                          15

<210> SEQ ID NO 1174
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1174
cagcaaaaaa aaaaa                                                          15

<210> SEQ ID NO 1175
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1175
agcaaaaaaa aaaaa                                                          15

<210> SEQ ID NO 1176
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1176
gcaaaaaaaa aaaaa                                                          15

<210> SEQ ID NO 1177
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1177
caaaaaaaaa aaaaa                                                          15

<210> SEQ ID NO 1178
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1178
aaaaaaaaaa aaaaa                                                          15

<210> SEQ ID NO 1179
<211> LENGTH: 15
<212> TYPE: DNA
<213> ORGANISM: artificial sequence
<220> FEATURE:
<223> OTHER INFORMATION: 15mer sense oligonucelotides which represent
      targets on HBA2 mRNA

<400> SEQUENCE: 1179
aaaaaaaaaa aaaaa                                                          15

<210> SEQ ID NO 1180
<211> LENGTH: 574
<212> TYPE: RNA
<213> ORGANISM: artificial sequence
<220> FEATURE:
<223> OTHER INFORMATION: Complement in same direction after U to T
      conversion - HBA1

```
<400> SEQUENCE: 1180
ugagaagacc aggggugucu gagucucucu ugggugguac cacgacagag gacggcuguu      60
cugguugcag uuccggcgga ccccauucca gccgcgcgug cgaccgcuca uaccacgccu     120 ccggaccuc  uccuacaagg acaggaaggg guggugguuc uggaugaagg gcgugaagcu     180
ggacucggug ccgagacggg uccaauuccc ggugccguuc uuccaccggc ugcgcgacug     240
guugcggcac cgcgugcacc ugcuguacgg guugcgcgac aggcgggacu cgcuggacgu     300
gcgcguguuc gaagcccacc ugggccaguu gaaguucgag gauucggguga cggacgacca    360 cuggaccgg  cggguggagg ggcggcucaa gugggacgc  cacgugcgga gggaccuguu     420
caaggaccga agacacucgu ggcacgacug gagguuuaug gcaauucgac cucggagcca    480
ucggcaagga ggacggcgac ccggaggguu gcccgggagg agggggaggaa cguggccggg    540 aaccaccaga aacuuauuuc agacucaccc gccg                                 574

<210> SEQ ID NO 1181
<211> LENGTH: 142
<212> TYPE: PRT
<213> ORGANISM: artificial
<220> FEATURE:
<223> OTHER INFORMATION: Amino acid sequence of HBA1

<400> SEQUENCE: 1181

Met Val Leu Ser Pro Ala Asp Lys Thr Asn Val Lys Ala Ala Trp Gly
1               5                   10                  15

Lys Val Gly Ala His Ala Gly Glu Tyr Gly Ala Glu Ala Leu Glu Arg
                20                  25                  30

Met Phe Leu Ser Phe Pro Thr Thr Lys Thr Tyr Phe Pro His Phe Asp
            35                  40                  45

Leu Ser His Gly Ser Ala Gln Val Lys Gly His Gly Lys Lys Val Ala
        50                  55                  60

Asp Ala Leu Thr Asn Ala Val Ala His Val Asp Asp Met Pro Asn Ala
65                  70                  75                  80

Leu Ser Ala Leu Ser Asp Leu His Ala His Lys Leu Arg Val Asp Pro
                85                  90                  95

Val Asn Phe Lys Leu Leu Ser His Cys Leu Leu Val Thr Leu Ala Ala
                100                 105                 110

His Leu Pro Ala Glu Phe Thr Pro Ala Val His Ala Ser Leu Asp Lys
            115                 120                 125

Phe Leu Ala Ser Val Ser Thr Val Leu Thr Ser Lys Tyr Arg
        130                 135                 140
```